(12) United States Patent
Hatakeyama et al.

(10) Patent No.: US 9,017,918 B2
(45) Date of Patent: *Apr. 28, 2015

(54) MONOMER, POLYMER, CHEMICALLY AMPLIFIED POSITIVE RESIST COMPOSITION, AND PATTERNING PROCESS

(75) Inventors: Jun Hatakeyama, Joetsu (JP); Seiichiro Tachibana, Joetsu (JP); Koji Hasegawa, Joetsu (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 237 days.

This patent is subject to a terminal disclaimer.

(21) Appl. No.: 13/150,698

(22) Filed: Jun. 1, 2011

(65) Prior Publication Data

US 2011/0294070 A1 Dec. 1, 2011

(30) Foreign Application Priority Data

Jun. 1, 2010 (JP) ................................ 2010-125889

(51) Int. Cl.
G03F 7/039 (2006.01)
G03F 7/20 (2006.01)
G03F 7/30 (2006.01)
C08F 218/10 (2006.01)
C07C 69/54 (2006.01)
C07C 69/96 (2006.01)
C08F 20/26 (2006.01)
C08F 214/18 (2006.01)
G03F 7/004 (2006.01)

(52) U.S. Cl.
CPC ............... *C08F 214/18* (2013.01); *C07C 69/54* (2013.01); *C07C 69/96* (2013.01); *C07C 2101/08* (2013.01); *C07C 2101/14* (2013.01); *C07C 2103/74* (2013.01); *C08F 20/26* (2013.01); *G03F 7/0045* (2013.01); *G03F 7/0392* (2013.01); *G03F 7/0395* (2013.01); *G03F 7/0397* (2013.01); *Y10S 430/111* (2013.01)

(58) Field of Classification Search
None
See application file for complete search history.

(56) References Cited

U.S. PATENT DOCUMENTS

| | | | |
|---|---|---|---|
| 5,415,749 A | 5/1995 | Hamilton | |
| 5,879,851 A | 3/1999 | Takahashi et al. | |
| 5,989,776 A | 11/1999 | Felter et al. | |
| 6,312,867 B1 | 11/2001 | Kinsho et al. | |
| 6,448,420 B1 | 9/2002 | Kinsho et al. | |
| 6,485,883 B2 | 11/2002 | Kodama et al. | |
| 6,746,817 B2 | 6/2004 | Takeda et al. | |
| 7,449,277 B2 | 11/2008 | Hatakeyama et al. | |
| 7,482,108 B2 | 1/2009 | Matsumaru et al. | |
| 7,501,223 B2 | 3/2009 | Takeda et al. | |
| 7,537,880 B2 | 5/2009 | Harada et al. | |
| 7,569,326 B2 | 8/2009 | Ohsawa et al. | |
| 7,598,016 B2 | 10/2009 | Kobayashi et al. | |
| 7,771,914 B2 | 8/2010 | Hatakeyama et al. | |
| 8,288,076 B2* | 10/2012 | Masunaga et al. | 430/270.1 |
| 8,361,693 B2* | 1/2013 | Masunaga et al. | 430/270.1 |
| 8,426,108 B2* | 4/2013 | Masunaga et al. | 430/270.1 |
| 2004/0260031 A1 | 12/2004 | Takeda et al. | |
| 2005/0014090 A1* | 1/2005 | Hirayama et al. | 430/270.1 |
| 2007/0111140 A1* | 5/2007 | Hatakeyama et al. | 430/270.1 |
| 2007/0231738 A1 | 10/2007 | Kaneko et al. | |
| 2008/0090172 A1 | 4/2008 | Hatakeyama et al. | |
| 2008/0096128 A1 | 4/2008 | Takeda et al. | |
| 2008/0096131 A1* | 4/2008 | Hatakeyama et al. | 430/281.1 |
| 2008/0214011 A1 | 9/2008 | Colburn et al. | |
| 2008/0241736 A1 | 10/2008 | Kobayashi et al. | |
| 2008/0311507 A1 | 12/2008 | Isono et al. | |
| 2009/0233223 A1 | 9/2009 | Tachibana et al. | |
| 2009/0269696 A1 | 10/2009 | Ohsawa et al. | |

(Continued)

FOREIGN PATENT DOCUMENTS

EP 0473547 A1 3/1992
EP 2090931 A1 8/2009

(Continued)

OTHER PUBLICATIONS

Chae et al ("Preparation of Chemically Amplified Photoresists with N-hydroxyphthalimide Styrenesulfonate groups and their properties", Journal of Photopolymer Science and Technology, vol. 7(1), p. 183-186 (1994)).*

Machine-assisted English translation for JP 2009-274260 provided by JPO (2009).*

European Search Report dated May 30, 2011, issued in European Patent Application No. 11001592.2 (7 pages).

Guerrero, Douglas et al., "A New Generation of Bottom Anti-Reflective Coatings (BARCs): Photodefinable BARCs", Proceedings of SPIE, 2003, p. 129-135, vol. 5039.

(Continued)

*Primary Examiner* — Sin J. Lee

(74) *Attorney, Agent, or Firm* — Westerman, Hattori, Daniels & Adrian, LLP

(57) ABSTRACT

A polymer is obtained from a hydroxyphenyl methacrylate monomer having an acid labile group substituted thereon. A positive resist composition comprising the polymer as a base resin has a very high contrast of alkaline dissolution rate before and after exposure, a high resolution, a good profile and minimal line edge roughness of a pattern after exposure, a retarded acid diffusion rate, and good etching resistance.

(1)

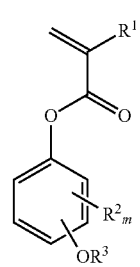

9 Claims, No Drawings

(56) References Cited

U.S. PATENT DOCUMENTS

| | | |
|---|---|---|
| 2009/0274978 A1 | 11/2009 | Ohashi et al. |
| 2009/0317742 A1 | 12/2009 | Toriumi et al. |
| 2010/0035185 A1 | 2/2010 | Hagiwara et al. |
| 2010/0159392 A1 | 6/2010 | Hatakeyama et al. |
| 2010/0304302 A1* | 12/2010 | Masunaga et al. ......... 430/285.1 |
| 2010/0316955 A1 | 12/2010 | Masunaga et al. |
| 2011/0212391 A1 | 9/2011 | Masunaga et al. |
| 2012/0108043 A1 | 5/2012 | Hatakeyama et al. |
| 2012/0135349 A1 | 5/2012 | Hatakeyama et al. |
| 2012/0202153 A1 | 8/2012 | Hatakeyama |
| 2013/0029270 A1 | 1/2013 | Hatakeyama |

FOREIGN PATENT DOCUMENTS

| | | |
|---|---|---|
| EP | 2112554 A2 | 10/2009 |
| JP | 4-230645 A | 8/1992 |
| JP | 9-309874 A | 12/1997 |
| JP | 2000-327633 A | 11/2000 |
| JP | 2000-336121 A | 12/2000 |
| JP | 2001-281849 A | 10/2001 |
| JP | 2001329228 A | 11/2001 |
| JP | 3429592 B2 | 5/2003 |
| JP | 2004-115630 A | 4/2004 |
| JP | 2004-175755 A | 6/2004 |
| JP | 2005-008766 A | 1/2005 |
| JP | 2005-084365 A | 3/2005 |
| JP | 2006-045311 A | 2/2006 |
| JP | 2006-169302 A | 6/2006 |
| JP | 2006-178317 A | 7/2006 |
| JP | 3865048 B2 | 1/2007 |
| JP | 2007-114728 A | 5/2007 |
| JP | 2007-297590 A | 11/2007 |
| JP | 2008-095009 A | 4/2008 |
| JP | 2008-111103 A | 5/2008 |
| JP | 2008-122932 A | 5/2008 |
| JP | 2008102383 A | 5/2008 |
| JP | 2008-133448 A | 6/2008 |
| JP | 2008-239918 A | 10/2008 |
| JP | 2009-007327 A | 1/2009 |
| JP | 2009-019199 A | 1/2009 |
| JP | 2009-145714 A | 7/2009 |
| JP | 2009-169406 A | 7/2009 |
| JP | 2009237150 A | 10/2009 |
| JP | 2009-269953 A | 11/2009 |
| JP | 2009-274260 * | 11/2009 |
| JP | 2010-152136 A | 7/2010 |
| JP | 2010-197618 A | 9/2010 |
| WO | WO 2010/026973 A1 * | 3/2010 |
| WO | 2010-119910 A1 | 10/2010 |
| WO | WO 2010/150917 A1 * | 12/2010 |

OTHER PUBLICATIONS

Meador, Jim et al., "Development of 193-nm wet BARCs for implant applications", Proceedings of SPIE, 2006, p. 61532P, vol. 6153.

Brainard, Robert et al., "Shot Noise, LER and Quantam Efficiency of EUV Photoresists", Proc. of SPIE, 2004, pp. 74-85, vol. 5374.

Kishikawa, Yasuhiro et al., "Assessment of trade-off between resist resolution and sensitivity for optimization of hyper-NA immersion lithography", Proc. of SPIE, 2007, pp. 65203L1-L9, vol. 6520.

Kozawa, Takahiro et al., "Basic aspects of acid generation processes in chemically amplified resists for electron beam lithography", Proc. of SPIE, 2005, pp. 361-367, vol. 5753.

Nakano, Atsuro et al., "Deprotonation mechanism of poly(4-hydroxystyrene) and its derivative", Proc. of SPIE, 2005, pp. 1034-1039, vol. 5753.

Hutchinson, John M., "The Shot Noise Impact on Resist Roughness in EUV Lithography", Proc. of SPIE, 1998, pp. 531-536, vol. 3331.

Hinsberg et al., "Extendibility of Chemically Amplified Resists : Another Brick wall?", Proc. of SPIE, 2003, pp. 1-14, vol. 5039.

Wang, Mingxing et al., "Novel Anionic Photoacid Generator (PAGs) and Photoresist for sub-50 nm Patterning by EUVL and EBL", Proc. of SPIE, 2007, pp. 6519F1-F6, vol. 6519.

Japanese Office Action dated Oct. 1, 2013, issued in corresponding Japanese Patent Application No. 2011-116721.

* cited by examiner

MONOMER, POLYMER, CHEMICALLY AMPLIFIED POSITIVE RESIST COMPOSITION, AND PATTERNING PROCESS

CROSS-REFERENCE TO RELATED APPLICATION

This non-provisional application claims priority under 35 U.S.C. §119(a) on Patent Application No. 2010-125889 filed in Japan on Jun. 1, 2010, the entire contents of which are hereby incorporated by reference.

TECHNICAL FIELD

This invention relates to a monomer, a polymer, a chemically amplified positive resist composition comprising the polymer as a base resin, and a patterning process using the composition.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, extreme ultraviolet (EUV) lithography of 13.5 nm wavelength, and double patterning version of the ArF lithography, on which active research efforts have been made.

With respect to high-energy radiation of very short wavelength such as electron beam (EB) or x-ray, hydrocarbons and similar light elements used in resist materials have little absorption. Then polyhydroxystyrene base resist materials are under consideration.

Resist materials for EB lithography are practically used in the mask image writing application. Recently, the mask manufacturing technology becomes of greater interest. Reduction projection exposure systems or steppers have been used since the time when the exposure light was g-line. While their demagnification factor was 1/5, a factor of 1/4 is now used as a result of chip size enlargement and projection lens diameter increase. It becomes of concern that a dimensional error of a mask has an impact on the dimensional variation of a pattern on wafer. It is pointed out that as the pattern feature is reduced, the value of a dimensional variation on the wafer becomes greater than the value of a dimensional error of the mask. This is evaluated by a mask error enhancement factor (MEEF) which is a dimensional variation on wafer divided by a dimensional error of mask. Patterns on the order of 45 nm often show an MEEF in excess of 4. In a situation including a demagnification factor of 1/4 and a MEEF of 4, the mask manufacture needs an accuracy substantially equivalent to that for equi-magnification masks.

The exposure system for mask manufacturing made a transition from the laser beam exposure system to the EB exposure system to increase the accuracy of line width. Since a further size reduction becomes possible by increasing the accelerating voltage of the electron gun in the EB exposure system, the accelerating voltage increased from 10 kV to 30 kV and reached 50 kV in the current mainstream system, with a voltage of 100 kV being under investigation.

As the accelerating voltage increases, a lowering of sensitivity of resist film becomes of concern. As the accelerating voltage increases, the influence of forward scattering in a resist film becomes so reduced that the contrast of electron image writing energy is improved to ameliorate resolution and dimensional control whereas electrons can pass straightforward through the resist film so that the resist film becomes less sensitive. Since the mask exposure tool is designed for exposure by direct continuous writing, a lowering of sensitivity of resist film leads to an undesirably reduced throughput. Due to a need for higher sensitivity, chemically amplified resist compositions are contemplated.

Thinning of resist film is in progress to facilitate reduction of pattern feature in the EB lithography for mask manufacturing and to prevent the pattern from collapsing due to a higher aspect ratio during development. In the case of photolithography, a thinning of resist film greatly contributes to resolution improvement. This is because introduction of chemical mechanical polishing (CMP) or the like has driven forward device planarization. In the case of mask manufacture, substrates are flat, and the thickness of processable substrates (e.g., Cr, MoSi or $SiO_2$) is predetermined by a percent light shield or phase shift control. The dry etch resistance of resist film must be improved before the film can be reduced in thickness.

It is generally believed that there is a correlation between the carbon density and the dry etching resistance of resist film. As the carbon density increases, the etching resistance improves.

Indene copolymers described in JP 3865048 and acenaphthylene copolymers described in JP-A 2006-169302 are expected to have improved etching resistance due to a high carbon density and a robust main chain structure based on cycloolefin structure.

Also, with respect to the soft x-ray (EUV) lithography of wavelength 5-20 nm, the reduced absorption of carbon atoms was reported. Increasing the carbon density is effective not only for improving dry etching resistance, but also for increasing the transmittance in the soft x-ray wavelength region.

As the feature size reduces, image blurs due to acid diffusion become a problem. To insure resolution for fine patterns with a size of 45 nm et seq., not only an improvement in dissolution contrast is important as previously reported, but control of acid diffusion is also important as recently reported. Since chemically amplified resist compositions are designed such that sensitivity and contrast are enhanced by acid diffusion, an attempt to minimize acid diffusion by reducing the temperature and/or time of post-exposure baking (PEB) fails, resulting in drastic reductions of sensitivity and contrast. Since the distance of acid diffusion is closely correlated to the type of acid labile group, it is desired to have an acid labile group capable of undergoing deprotection reaction within a very short distance of acid diffusion.

It is pointed out that an ArF resist material comprising a carboxylic acid such as methacrylic acid whose carboxyl group is substituted with an acid labile group swells in an alkaline developer. On the other hand, a KrF resist material comprising hydroxystyrene whose phenol group is substituted with an acid labile group little swells. However, the hydroxystyrene allows for substantial acid diffusion, leaving concern about a decline of resolution. It is desired to have a resist material featuring reduced acid diffusion and minimal swell in alkaline developer.

JP-A 2007-114728 describes hydroxyphenyl methacrylate as the adhesive group. It is effective for reducing swell like hydroxystyrene and more effective in suppressing acid diffusion than hydroxystyrene. In this patent document, a methacrylate having an acid labile group-substituted naphthol is also disclosed.

Addition of an acid generator capable of generating a bulky acid is effective for suppressing acid diffusion. It is then proposed to copolymerize a polymer with an acid generator in the form of a polymerizable olefin-containing onium salt. JP-A H04-230645, JP-A 2005-084365, and JP-A 2006-045311 disclose polymerizable olefin-containing sulfonium salts capable of generating a specific sulfonic acid and similar iodonium salts.

CITATION LIST

Patent Document 1: JP 3865048
Patent Document 2: JP-A 2006-169302
Patent Document 3: JP-A 2007-114728
Patent Document 4: JP-A H04-230645
Patent Document 5: JP-A 2005-084365
Patent Document 6: JP-A 2006-045311

DISCLOSURE OF INVENTION

An object of the present invention is to provide a positive resist composition, typically chemically amplified positive resist composition, comprising a specific polymer, which exhibits a high resolution surpassing prior art positive resist compositions, and forms a resist film having a minimal line edge roughness (LER), a good pattern profile after exposure, and improved etching resistance. Another object is to provide a polymer suited for use as a base resin in the resist composition, and a polymerizable monomer for forming the polymer. A further object is to provide a pattern forming process using the composition.

The inventors made efforts to develop the desired positive resist composition which exhibits a high resolution, a minimal LER, a good pattern profile for etching, and improved etching resistance. Methacrylic acid polymers are effective in suppressing acid diffusion whereas the phenolic hydroxyl group is characterized by a lower swell in alkaline aqueous solution than the carboxyl group. A resist material comprising hydroxyphenyl methacrylate as the adhesive group is effective in reducing swell while suppressing acid diffusion. Also, a resist material comprising a copolymer of a methacrylate having an acid labile group-substituted naphthol experiences little swell in alkaline solution, but has a low dissolution contrast since the naphthol from which the acid labile group has been deprotected has a low alkaline dissolution rate. Better results are thus obtained from a positive resist composition, typically chemically amplified positive resist composition, in which a polymer comprising recurring units derived from a polymerizable monomer having the structure that the hydroxyl group of hydroxyphenyl methacrylate is substituted with an acid labile group as represented by the general formula (1) is used as the base resin.

The relevant polymer is used as the base resin in a positive resist composition, typically chemically amplified positive resist composition, for the purpose of improving dissolution contrast and etching resistance while suppressing acid diffusion. The resulting positive resist composition, typically chemically amplified positive resist composition is effective for suppressing swell during development in alkaline aqueous solution, suppressing acid diffusion, and preventing pattern collapse. The composition also exhibits high resolution, good pattern profile after exposure, reduced edge roughness, and improved etch resistance. The composition is thus suited as micropatterning material for the fabrication of VLSIs and photomasks.

The positive resist composition comprising the relevant polymer as the base resin forms a resist film which has a high dissolution contrast, is effective in suppressing acid diffusion, and exhibits a high resolution, a satisfactory exposure latitude, process adaptability, a good pattern profile after exposure, and excellent etch resistance. Because of these advantages, the resist composition is fully practical in the lithography and very effective as the VLSI-forming resist material and mask pattern-forming material.

In one aspect, the invention provides a polymerizable monomer having the general formula (1):

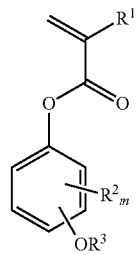

wherein $R^1$ is hydrogen or methyl, $R^2$ is hydrogen or $C_1$-$C_4$ alkyl, $R^3$ is an acid labile group, and m is an integer of 1 to 4.

In a second aspect, the invention provides a polymer comprising recurring units (a) having the general formula (2):

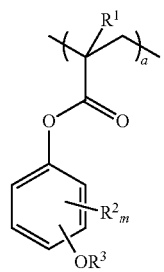

wherein $R^1$ is hydrogen or methyl, $R^2$ is hydrogen or $C_1$-$C_4$ alkyl, $R^3$ is an acid labile group, m is an integer of 1 to 4, and a is a positive number from more than 0 to 1.0, the polymer having a weight average molecular weight of 1,000 to 500,000.

In formulae (1) and (2), the acid labile group $R^3$ is typically t-butyl, t-amyl, methylcyclopentyl, ethylcyclopentyl, methylcyclohexyl, ethylcyclohexyl, methyladamantyl, ethyladamantyl, t-butoxycarbonyl, t-amyloxycarbonyl, or —$CR^4R^5$—O—$R^6$ wherein $R^4$ and $R^5$ are each independently hydrogen or $C_1$-$C_4$ straight or branched alkyl, and $R^6$ is $C_1$-$C_{12}$ straight, branched or cyclic alkyl or $C_2$-$C_{12}$ alkenyl.

The polymer may further comprise recurring units (b) having an adhesive group selected from the group consisting of hydroxyl, lactone ring, ether, ester, carbonyl, cyano, cyclic —O—C(=O)—S— and cyclic —O—C(=O)—NH— wherein fractions "a" and "b" of the respective units are numbers in the range: 0<a<1.0, 0<b<1.0, and 0.05≤a+b≤1.0.

Preferably the recurring units (b) are recurring units having a phenolic hydroxyl group. More preferably, the recurring units having a phenolic hydroxyl group are units of at least one type selected from recurring units (b1) to (b8) having the general formula (3):

(3)

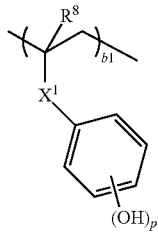 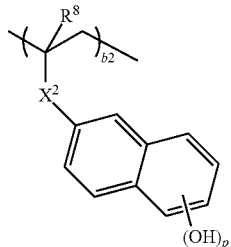

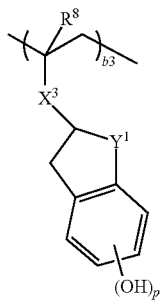 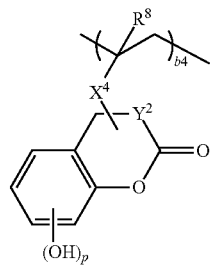

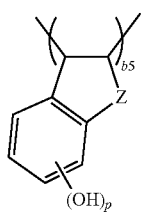 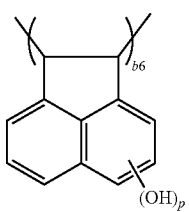

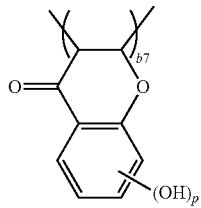 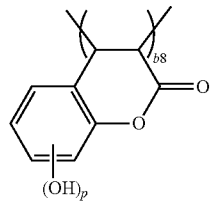

wherein $R^8$ is hydrogen or methyl, $X^1$ and $X^2$ are a single bond or a group —C(=O)—O—$R^9$—, $X^3$ and $X^4$ are a group —C(=O)—O—$R^9$—, $R^9$ is a single bond or $C_1$-$C_{10}$ straight, branched or cyclic alkylene, $Y^1$ and $Y^2$ are methylene or ethylene, Z is methylene, oxygen or sulfur atom, p is 1 or 2, b1 to b8 are positive numbers in the range: $0 \leq b1 < 1.0$, $0 \leq b2 < 1.0$, $0 \leq b3 < 1.0$, $0 \leq b4 < 1.0$, $0 \leq b5 < 1.0$, $0 \leq b6 < 1.0$, $0 \leq b7 < 1.0$, $0 \leq b8 < 1.0$, and $0 < b1+b2+b3+b4+b5+b6+b7+b8 < 1.0$.

The polymer may further comprise recurring units (c) of at least one type selected from recurring units (c1) to (c5) of indene, acenaphthylene, chromone, coumarin, and norbornadiene, or derivatives thereof, represented by the general formula (4):

(4)

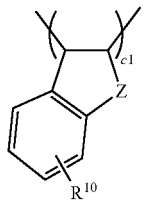 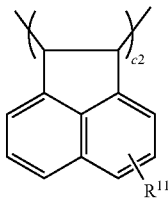

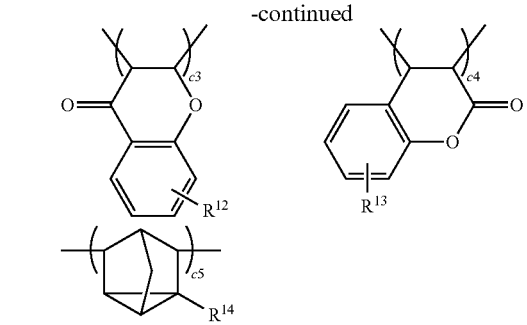

wherein $R^{10}$ to $R^{14}$ are each independently selected from the group consisting of hydrogen, $C_1$-$C_{30}$ alkyl, $C_1$-$C_{30}$ alkyl wherein some or all carbon-bonded hydrogen atoms are substituted by halogen atoms, $C_1$-$C_8$ alkoxy, $C_1$-$C_8$ alkanoyl, $C_2$-$C_8$ alkoxycarbonyl, $C_6$-$C_{10}$ aryl, halogen, and 1,1,1,3,3,3-hexafluoro-2-propanol group, and Z is methylene, oxygen or sulfur, c1 to c5 are positive numbers in the range: $0 \leq c1 < 1.0$, $0 \leq c2 < 1.0$, $0 \leq c3 < 1.0$, $0 \leq c4 < 1.0$, $0 \leq c5 < 1.0$, and $0 < c1+c2+c3+c4+c5 < 1.0$.

The polymer may further comprise recurring units (d) of a polymerizable olefin-containing onium salt having serving as an acid generator selected from sulfonium salt-derived recurring units (d1) to (d3) represented by the general formula (5):

(5)

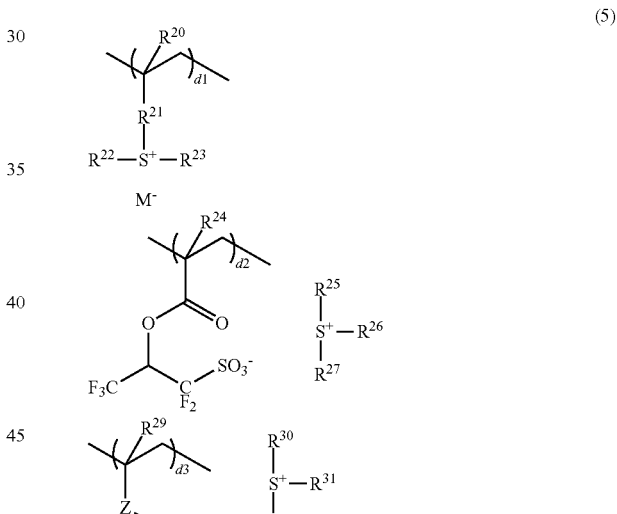

wherein $R^{20}$, $R^{24}$ and $R^{29}$ each are hydrogen or methyl, $R^{21}$ is a single bond, phenylene, —O—$R^{28}$—, or —C(=O)—Y—$R^{28}$—, Y is oxygen or NH, $R^{28}$ is a straight, branched or cyclic $C_1$-$C_6$ alkylene group, alkenylene group or phenylene group, which may contain a carbonyl, ester, ether or hydroxyl group, $R^{22}$, $R^{23}$, $R^{25}$, $R^{26}$, $R^{27}$, $R^{30}$, $R^{31}$, and $R^{32}$ are each independently a straight, branched or cyclic $C_1$-$C_{12}$ alkyl group which may contain a carbonyl, ester or ether group, or $C_6$-$C_{12}$ aryl group, $C_7$-$C_{20}$ aralkyl group, or thiophenyl group, Z is a single bond, methylene, ethylene, phenylene, fluorinated phenylene, —O—$R^{33}$—, or —C(=O)—$Z^1$—$R^{33}$—, $Z^1$ is oxygen or NH, $R^{33}$ is a straight, branched or cyclic $C_1$-$C_6$ alkylene group, alkenylene group or phenylene group, which may contain a carbonyl, ester, ether or hydroxyl group, $M^-$ is a non-nucleophilic counter ion, and d1 to d3 are numbers in the range: $0 \leq d1 \leq 0.5$, $0 \leq d2 \leq 0.5$, $0 \leq d3 \leq 0.5$, and $0 < d1+d2+d3 \leq 0.5$.

In a third aspect, the invention provides a chemically amplified positive resist composition comprising the polymer defined above and an organic solvent.

In a preferred embodiment, the resist composition may further comprise a dissolution regulator and optionally, at least one additive selected from an acid generator, basic compound and surfactant.

In a fourth aspect, the invention provides a pattern forming process comprising the steps of applying the positive resist composition defined above onto a substrate to form a coating, heat treating and exposing the coating to high-energy radiation, and developing the exposed coating with a developer.

ADVANTAGEOUS EFFECTS OF INVENTION

The positive resist composition comprising a polymer obtained from (co)polymerization of a polymerizable monomer as the base resin has a very high contrast of alkaline dissolution rate before and after exposure, a high resolution, a good profile and minimal line edge roughness of a pattern after exposure, a retarded acid diffusion rate, and good etching resistance. Accordingly, the positive resist composition, especially chemically amplified positive resist composition is useful as a micropatterning material for the fabrication of VLSI and photomasks and a pattern-forming material for the EUV lithography.

The positive resist composition, especially chemically amplified positive resist composition is useful not only in the lithography for forming semiconductor circuits, but also in the lithography for forming mask circuit patterns, micromachines, thin-film magnetic head circuits, and the like.

DESCRIPTION OF EMBODIMENTS

The singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not.

As used herein, the terminology "(meth)acrylate" refers collectively to acrylate and methacrylate. The terminology "$C_x$-$C_y$", as applied to a particular unit, such as, for example, a chemical compound or a chemical substituent group, means having a carbon atom content of from "x" carbon atoms to "y" carbon atoms per such unit.

The acronyms LER and LWR are line edge roughness and line width roughness, respectively, and PEB stands for post-exposure baking.

Monomer

One embodiment of the invention is a polymerizable monomer having the general formula (1).

(1)

Herein $R^1$ is hydrogen or methyl, $R^2$ is hydrogen or $C_1$-$C_4$ alkyl, $R^3$ is an acid labile group, and m is an integer of 1 to 4.

Examples of the $C_1$-$C_4$ alkyl group of $R^2$ include methyl, ethyl, propyl and butyl.

In formula (1), $R^3$ is an acid labile group, examples of which will be described later. Preferably, $R^3$ is selected from among t-butyl, t-amyl, methylcyclopentyl, ethylcyclopentyl, methylcyclohexyl, ethylcyclohexyl, methyladamantyl, ethyladamantyl, t-butoxycarbonyl, t-amyloxycarbonyl, and —$CR^4R^5$—O—$R^6$ wherein $R^4$ and $R^5$ are each independently hydrogen or $C_1$-$C_4$ straight or branched alkyl, and $R^6$ is $C_1$-$C_{12}$ straight, branched or cyclic alkyl or $C_2$-$C_{12}$ alkenyl.

The monomer of formula (1) may be prepared through step (i), (ii)-(iii) or (iv)-(v)-(iii) as shown by the following reaction scheme although the preparation method is not limited thereto.

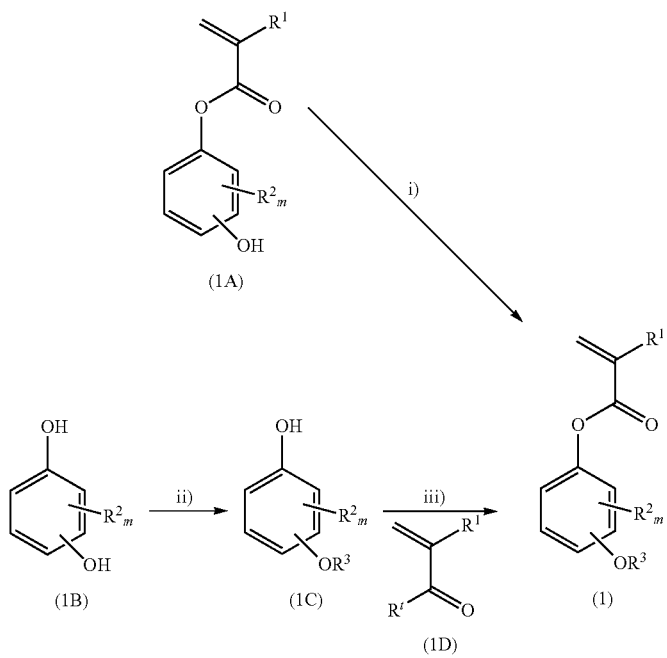

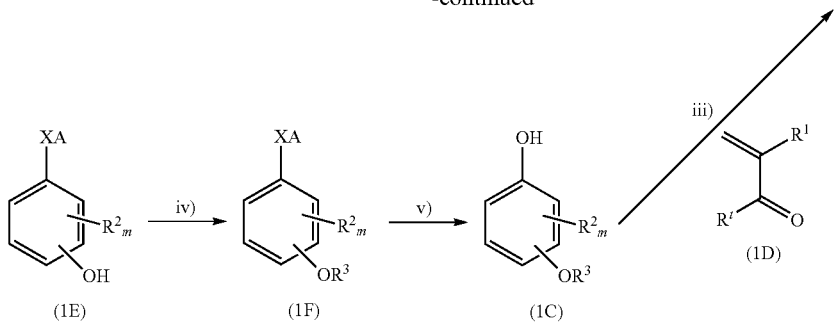

Herein $R^1$, $R^2$ and m are as defined above, XA is halogen, and $R^t$ is halogen or —$OR^7$. $R^7$ is hydrogen, methyl, ethyl or a group of the formula (1G):

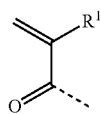

wherein $R^1$ is as defined above and the broken line denotes a valence bond.

Step (i) is to convert a monomer having a phenolic hydroxyl group (1A) into the desired monomer (1) by protection.

The reaction of step (i) readily takes place under well-known conditions. In an example wherein $R^3$ is a tertiary alkyl group such as t-butyl, t-amyl, methylcyclopentyl, ethylcyclopentyl, methylcyclohexyl, ethylcyclohexyl, methyladamantyl, or ethyladamantyl, a monomer (1A) and an olefin corresponding to $R^3$ such as isobutene or isoamylene are reacted in a solventless system or in a solvent such as toluene or hexane in the presence of an acid catalyst at a temperature of −20° C. to 50° C. Examples of the acid catalyst used herein include mineral acids such as hydrochloric acid, sulfuric acid, nitric acid and perchloric acid and organic acids such as methanesulfonic acid, trifluoromethanesulfonic acid, p-toluenesulfonic acid, and benzenesulfonic acid.

Step (ii) is to convert a hydroquinone derivative (1B) into an intermediate phenol compound (1C) by protection. The reaction used herein may be the same as described for step (i).

Step (iii) is reaction of intermediate phenol compound (1C) with an esterifying agent (1D) to form the desired monomer (1).

The reaction of step (iii) readily takes place under well-known conditions. The preferred esterifying agent (1D) is an acid chloride (formula (1D) wherein $R^t$ is chlorine) or carboxylic acid (formula (1D) wherein $R^t$ is hydroxyl). When an acid chloride is used, the reaction may be conducted in a solventless system or in a solvent (e.g., methylene chloride, toluene, hexane, diethyl ether, tetrahydrofuran or acetonitrile) by adding intermediate phenol compound (1C), a corresponding acid chloride (e.g., acrylic acid chloride or methacrylic acid chloride) and a base (e.g., triethylamine, pyridine or 4-dimethylaminopyridine) in sequence or at the same time, and optional cooling or heating. When a carboxylic acid is used, the reaction may be conducted in a solvent (e.g., toluene or hexane) by heating intermediate phenol compound (1C) and a corresponding carboxylic acid (e.g., acrylic acid or methacrylic acid) in the presence of an acid catalyst, and optionally removing the resulting water from the system. Examples of the acid catalyst used herein include mineral acids such as hydrochloric acid, sulfuric acid, nitric acid and perchloric acid and organic acids such as p-toluenesulfonic acid and benzenesulfonic acid.

Step (iv) is to convert a halogenated phenol compound (1E) to an intermediate halogenated aryl compound (1F) by protection. The reaction used herein may be conducted by the same procedure as described for step (i).

Step (v) is to oxidize intermediate halogenated aryl compound (1F) into intermediate phenol compound (1C). The reaction may be conducted in a standard way, for example, according to the following scheme.

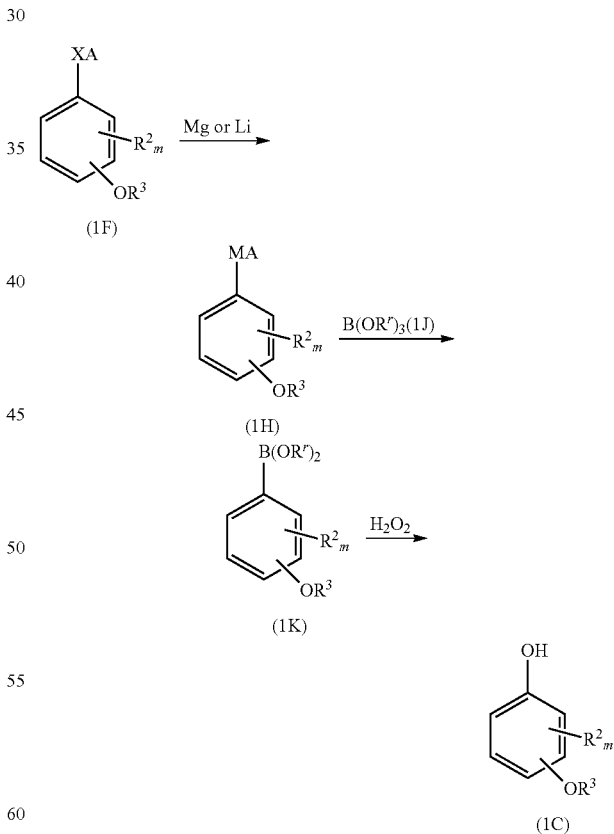

Herein $R^2$, $R^3$, m and XA are as defined above, MA is Li, MgCl, MgBr or MgI, and $R^r$ is a straight, branched or cyclic monovalent hydrocarbon group of 1 to 6 carbon atoms.

First, an organometallic reagent (1H) is prepared from halogenated aryl compound (1F) and Li or Mg in a solvent such as tetrahydrofuran or diethyl ether. Then the reagent (1H) is reacted with a boric acid ester (1J) to form an aryl boric acid derivative (1K), which is in turn reacted with an oxidizing agent (e.g., hydrogen peroxide, performic acid, peracetic acid or m-chloroperbenzoic acid), yielding intermediate phenol compound (1C). This process typically allows the reaction to run in one pot without any intermediate purifying step.

Illustrative examples of the polymerizable monomer having formula (1) are given below.

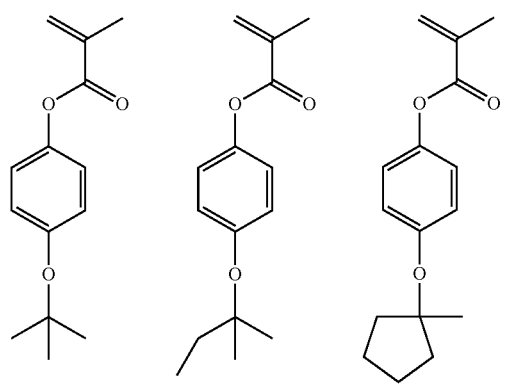

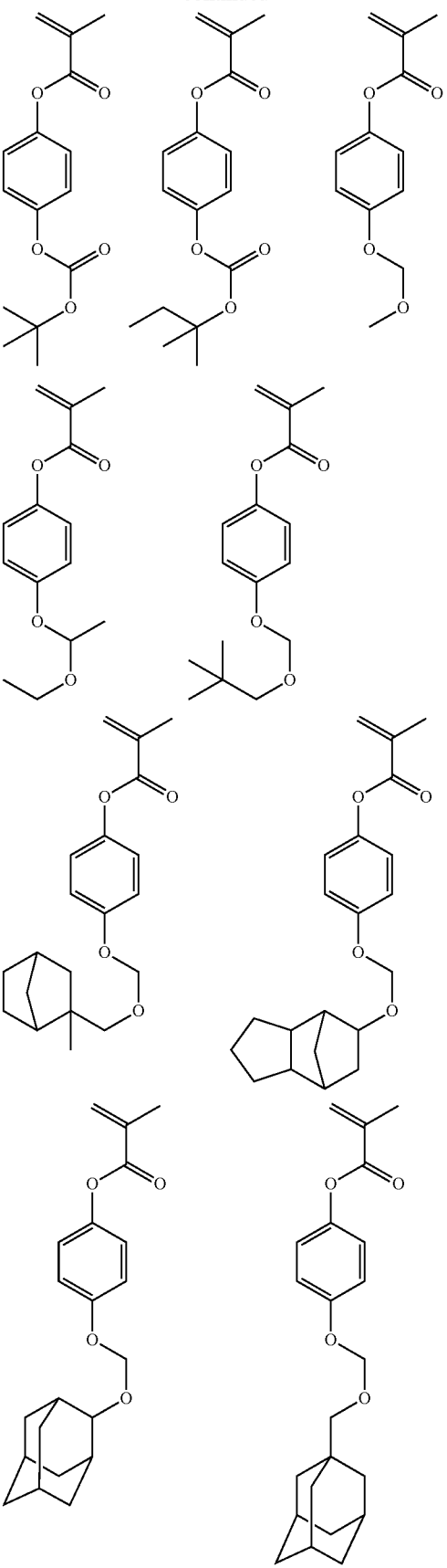

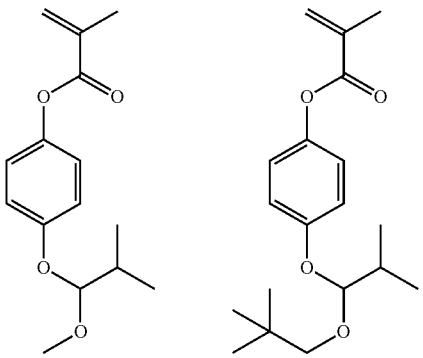
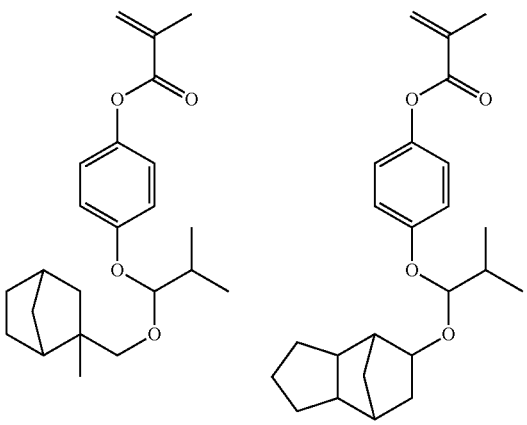
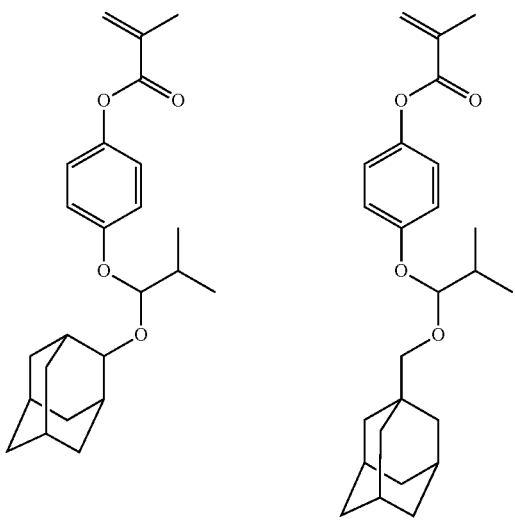

Polymer

A polymer having a weight average molecular weight (Mw) of 1,000 to 500,000 is obtained from (co)polymerization of the monomer having formula (1). Specifically, the polymer comprises recurring units (a) having the general formula (2).

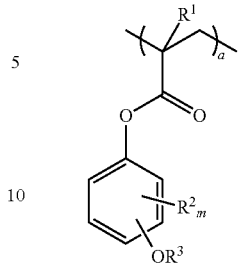

(2)

Herein $R^1$, $R^2$, $R^3$ and m are as defined above, and a is a positive number from more than 0 to 1.0 (0<a≤1.0).

The recurring units of formula (2) included in the polymer may be of one type or a mixture of two or more types having different acid labile groups.

In formulae (1) and (2), the acid labile group represented by $R^3$ may be selected from a variety of such groups. Suitable acid labile groups include groups of the following formulae (A-1) to (A-3).

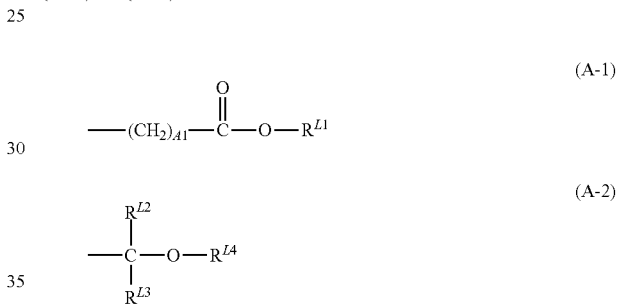

(A-1)

(A-2)

(A-3)

In formula (A-1), $R^{L1}$ is a tertiary alkyl group of 4 to 20 carbon atoms, preferably 4 to 15 carbon atoms, trialkylsilyl group of 1 to 6 carbon atoms, oxoalkyl group of 4 to 20 carbon atoms, or a group of formula (A-3). Suitable tertiary alkyl groups include tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, and 2-methyl-2-adamantyl. Suitable trialkylsilyl groups include trimethylsilyl, triethylsilyl, and dimethyl-tert-butylsilyl. Suitable oxoalkyl groups include 3-oxocyclohexyl, 4-methyl-2-oxooxan-4-yl, and 5-methyl-2-oxooxolan-5-yl. Al is an integer of 0 to 6.

Examples of the acid labile group having formula (A-1) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Also preferred are those groups having the following formulae (A-1)-1 to (A-1)-10.

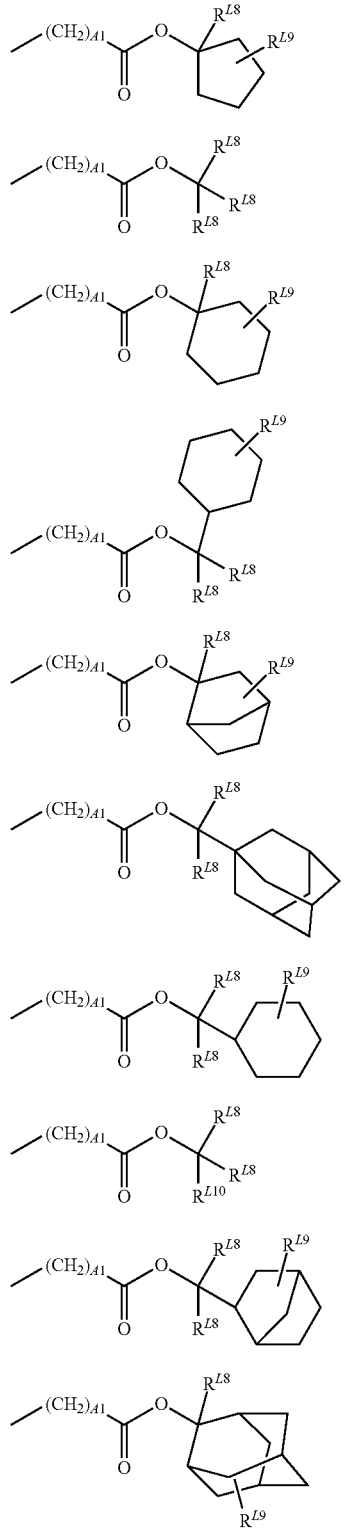

In the above formulae, $R^{L8}$ is each independently a straight, branched or cyclic $C_1$-$C_{10}$ alkyl group or a $C_6$-$C_{20}$ aryl group. $R^{L9}$ is hydrogen or a straight, branched or cyclic $C_1$-$C_{10}$ alkyl group. $R^{L10}$ is a straight, branched or cyclic $C_2$-$C_{10}$ alkyl group or a $C_6$-$C_{20}$ aryl group. A1 is an integer of 0 to 6.

In formula (A-2), $R^{L2}$ and $R^{L3}$ are hydrogen or a straight, branched or cyclic alkyl group of 1 to 18 carbon atoms, preferably 1 to 10 carbon atoms. Suitable alkyl groups include methyl, ethyl, propyl, isopropyl, n-butyl, sec-butyl, tert-butyl, cyclopentyl, cyclohexyl, 2-ethylhexyl, and n-octyl. $R^{L4}$ is a monovalent hydrocarbon group of 1 to 18 carbon atoms, preferably 1 to 10 carbon atoms, which may contain a heteroatom such as oxygen. Suitable monovalent hydrocarbon groups include straight, branched or cyclic alkyl groups and substituted forms of these alkyl groups in which some hydrogen atoms are substituted by hydroxyl, alkoxy, oxo, amino, or alkylamino groups. Examples of the substituted alkyl groups are shown below.

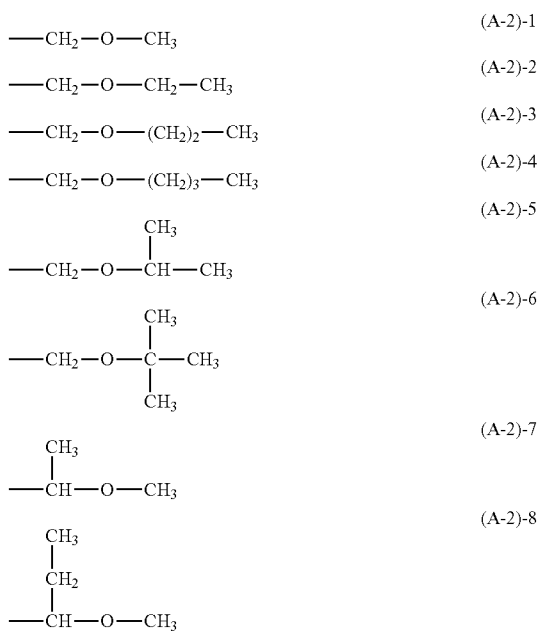

A pair of $R^{L2}$ and $R^{L3}$, $R^{L2}$ and $R^{L4}$, or $R^{L3}$ and $R^{L4}$ may bond together to form a ring with the carbon atom to which they are attached. In this event, each of ring-forming $R^{L2}$ and $R^{L3}$, $R^{L2}$ and $R^{L4}$, or $R^{L3}$ and $R^{L4}$ is a straight or branched alkylene group of 1 to 18 carbon atoms, preferably 1 to 10 carbon atoms while the carbon count of the ring preferably ranges from 3 to 10, more preferably from 4 to 10.

Of the acid labile groups of formula (A-2), the straight and branched ones are exemplified by the following groups having formulae (A-2)-1 to (A-2)-69.

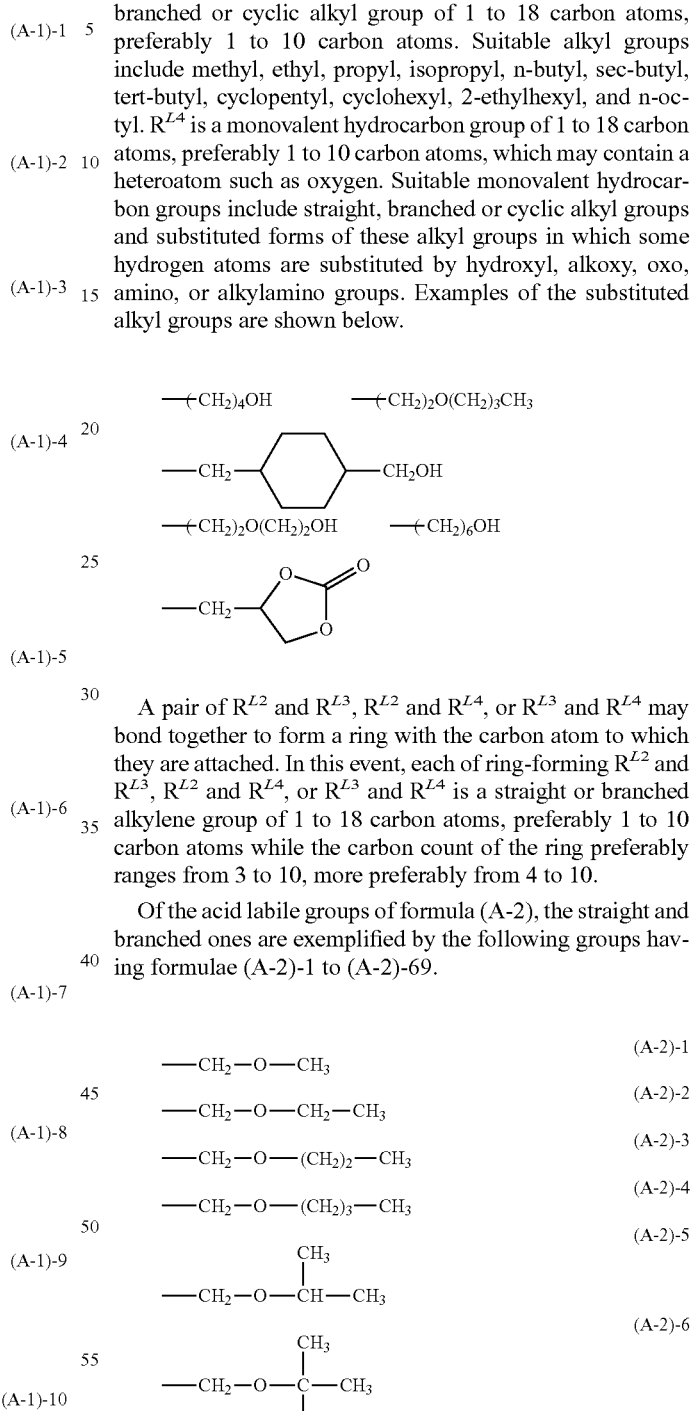

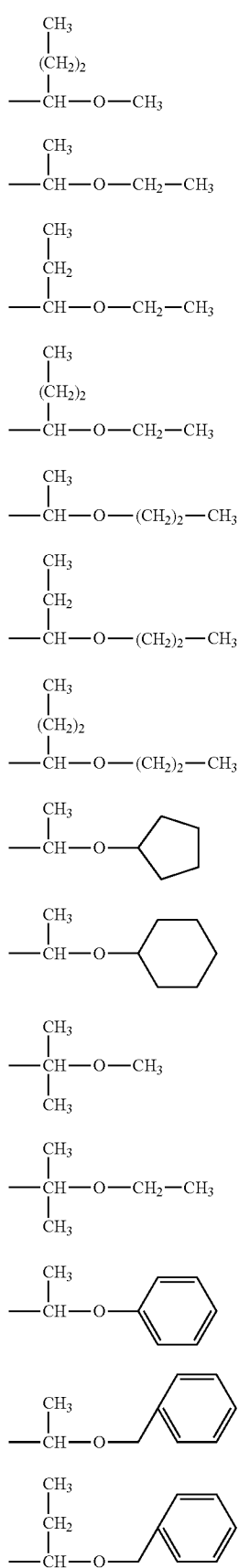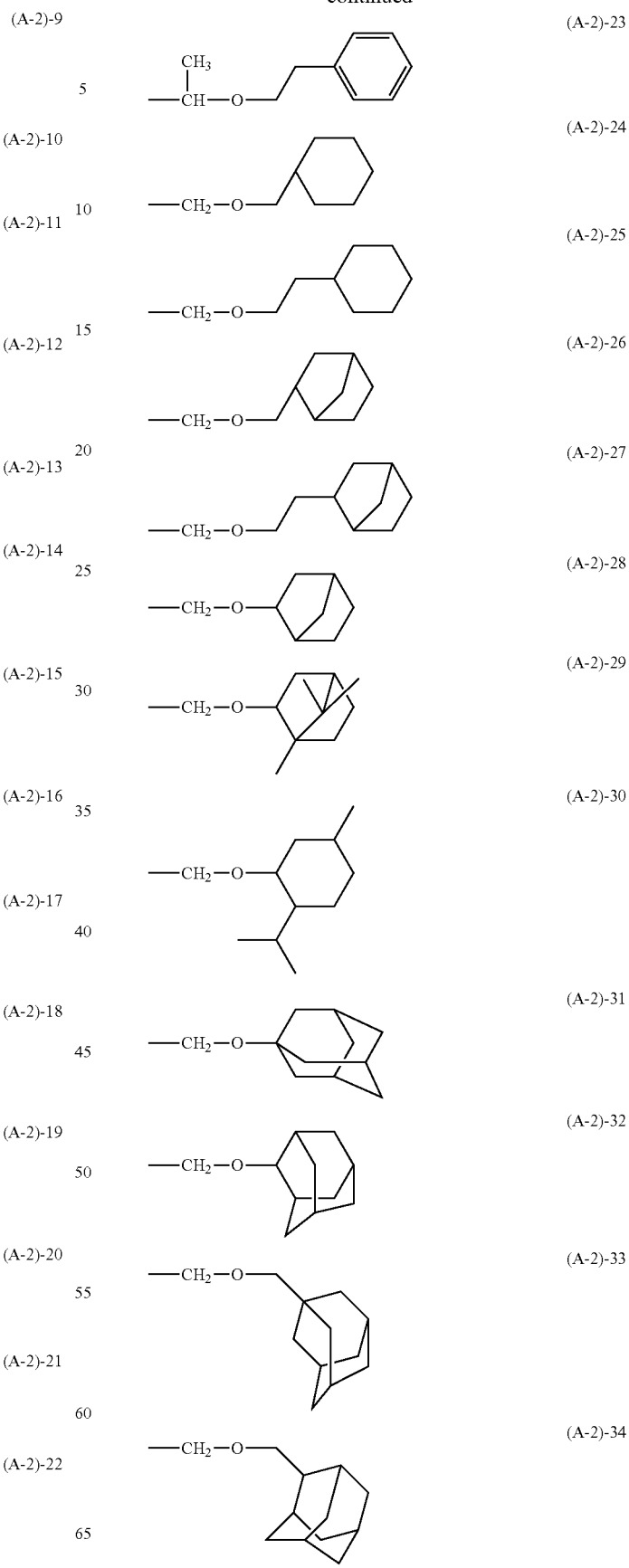

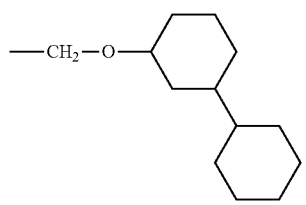
(A-2)-35
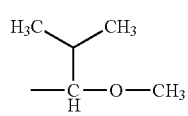
(A-2)-36
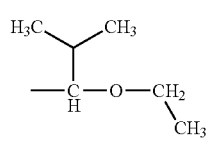
(A-2)-37
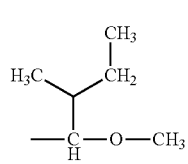
(A-2)-38
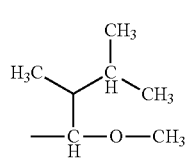
(A-2)-39
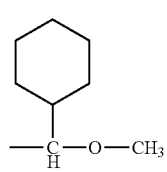
(A-2)-40
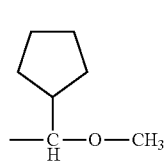
(A-2)-41
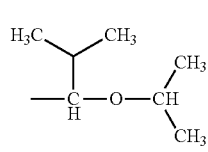
(A-2)-42
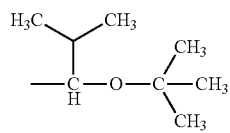
(A-2)-43
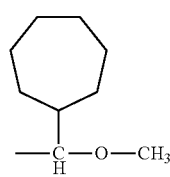
(A-2)-44
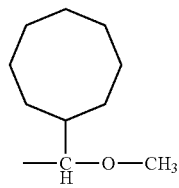
(A-2)-45
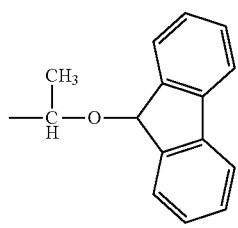
(A-2)-46
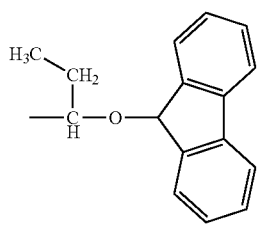
(A-2)-47
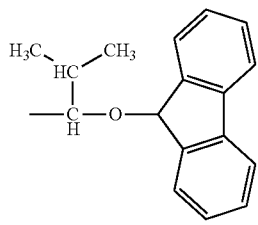
(A-2)-48
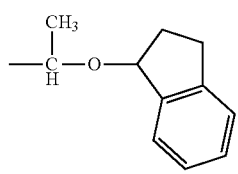
(A-2)-49
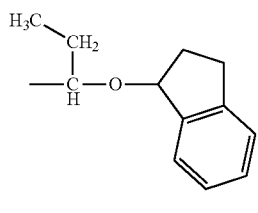
(A-2)-50
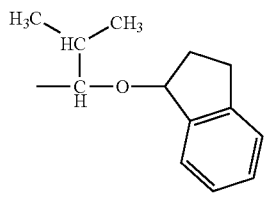
(A-2)-51
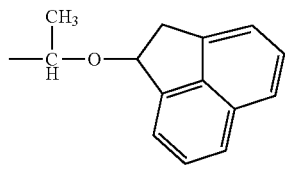
(A-2)-52

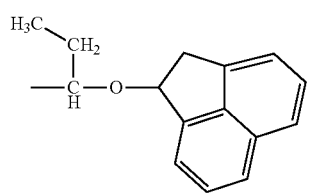 (A-2)-53
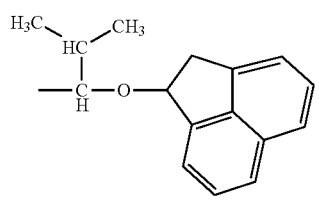 (A-2)-54
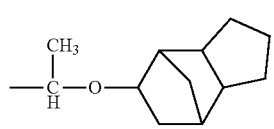 (A-2)-55
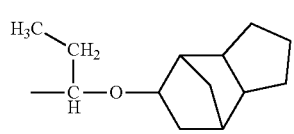 (A-2)-56
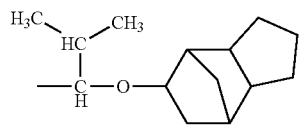 (A-2)-57
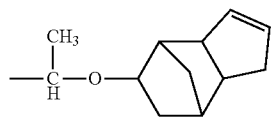 (A-2)-58
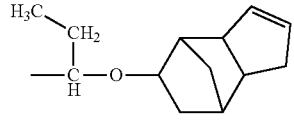 (A-2)-59
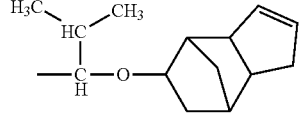 (A-2)-60
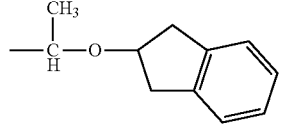 (A-2)-61
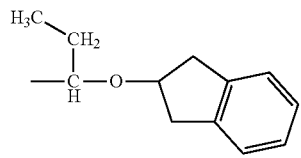 (A-2)-62
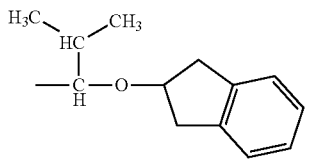 (A-2)-63
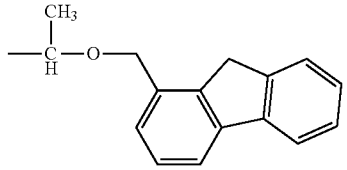 (A-2)-64
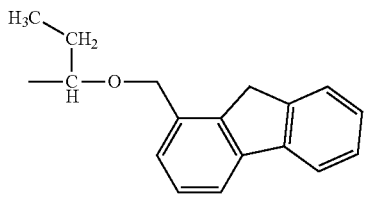 (A-2)-65
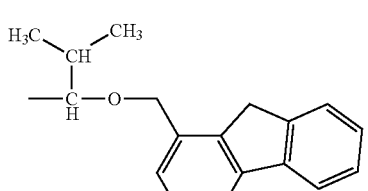 (A-2)-66
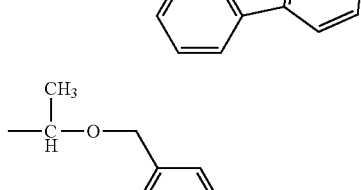 (A-2)-67
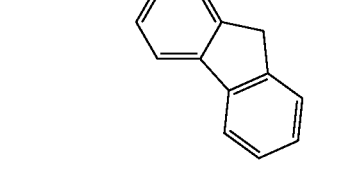 (A-2)-68
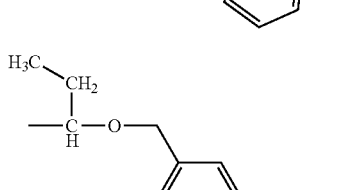 (A-2)-69

Of the acid labile groups of formula (A-2), the cyclic ones are, for example, tetrahydrofuran-2-yl, 2-methyltetrahydrofuran-2-yl, tetrahydropyran-2-yl, and 2-methyltetrahydropyran-2-yl.

Other examples of acid labile groups include those of the following formula (A-2a) or (A-2b) while the polymer may be crosslinked within the molecule or between molecules with these acid labile groups.

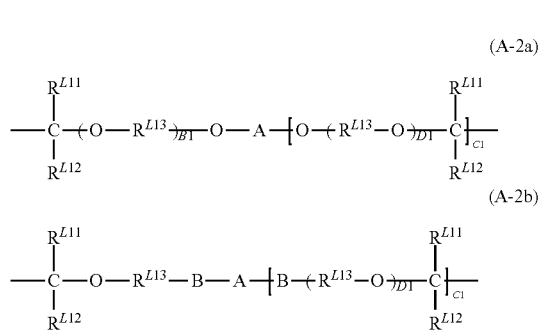

Herein $R^{L11}$ and $R^{L12}$ each are hydrogen or a straight, branched or cyclic $C_1$-$C_8$ alkyl group. $R^{L11}$ and $R^{L12}$ may bond together to form a ring with the carbon atom to which they are attached, and $R^{L40}$ and $R^{L41}$ are straight or branched $C_1$-$C_8$ alkylene groups when they form a ring. $R^{L13}$ is a straight, branched or cyclic $C_1$-$C_{10}$ alkylene group. "A" is a (C1+1)-valent aliphatic or alicyclic saturated hydrocarbon group, aromatic hydrocarbon group or heterocyclic group having 1 to 50 carbon atoms, which may be separated by a heteroatom or in which some carbon-bonded hydrogen atoms may be substituted by hydroxyl, carboxyl, acyl groups or fluorine atoms. "B" is —CO—O—, —NHCO—O— or —NHCONH—. Each of B1 and D1 is 0 or an integer of 1 to 10, preferably 0 or an integer of 1 to 5, and C1 is an integer of 1 to 7.

Preferably, "A" is selected from divalent to tetravalent, straight, branched or cyclic $C_1$-$C_{20}$ alkylene, alkyltriyl and alkyltetrayl groups, and $C_6$-$C_{30}$ arylene groups, which may contain a heteroatom or in which some carbon-bonded hydrogen atoms may be substituted by hydroxyl, carboxyl, acyl groups or halogen atoms. The subscript C1 is preferably an integer of 1 to 3.

The crosslinking acetal groups of formulae (A-2a) and (A-2b) are exemplified by the following formulae (A-2)-70 through (A-2)-77.

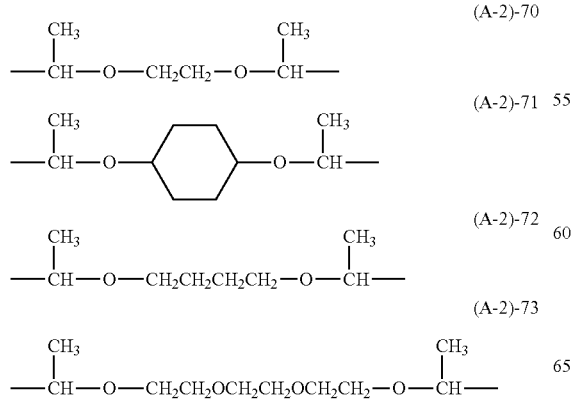

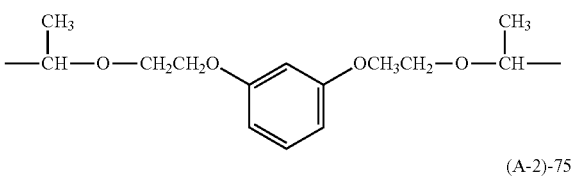

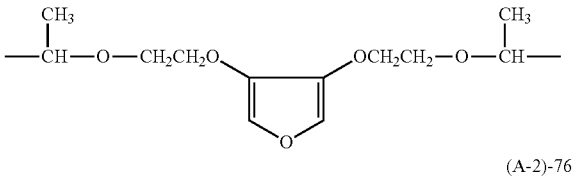

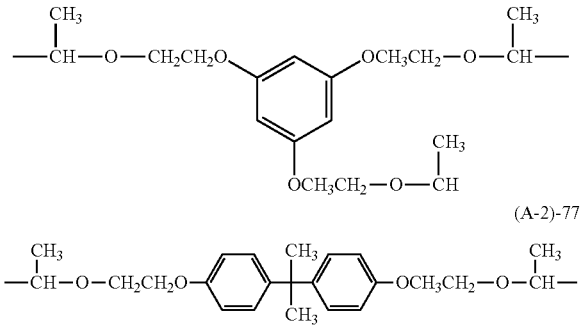

In formula (A-3), $R^{L5}$, $R^{L6}$ and $R^{L7}$ each are a monovalent hydrocarbon group, typically a straight, branched or cyclic $C_1$-$C_{20}$ alkyl group, which may contain a heteroatom such as oxygen, sulfur, nitrogen or fluorine. A pair of $R^{L5}$ and $R^{L6}$, $R^{L5}$ and $R^{L7}$, or $R^{L6}$ and $R^{L7}$ may bond together to form a ring with the carbon atom to which they are attached. In this event, each of ring-forming $R^{L5}$ and $R^{L6}$, $R^{L5}$ and $R^{L7}$, or $R^{L6}$ and $R^{L7}$ is a straight or branched alkylene group of 1 to 20 carbon atoms while the carbon count of the ring preferably ranges from 3 to 20.

Exemplary tertiary alkyl groups of formula (A-3) include tert-butyl, triethylcarbyl, 1-ethylnorbornyl, 1-methylcyclohexyl, 1-ethylcyclopentyl, 2-(2-methyl)adamantyl, 2-(2-ethyl)adamantyl, and tert-amyl.

Other exemplary tertiary alkyl groups of formula (A-3) include those of the following formulae (A-3)-1 to (A-3)-18.

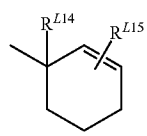
(A-3)-4

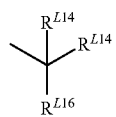
(A-3)-5

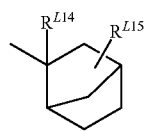
(A-3)-6

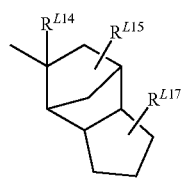
(A-3)-7

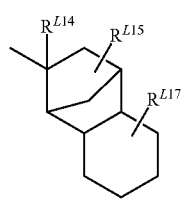
(A-3)-8

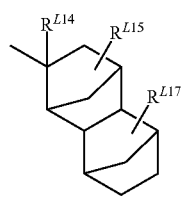
(A-3)-9

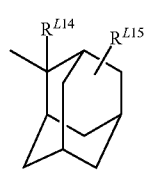
(A-3)-10

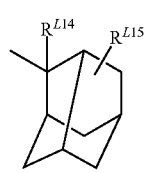
(A-3)-11

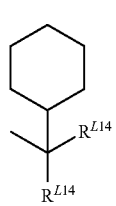
(A-3)-12

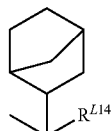
(A-3)-13

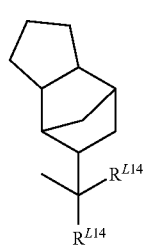
(A-3)-14

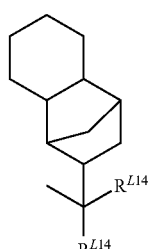
(A-3)-15

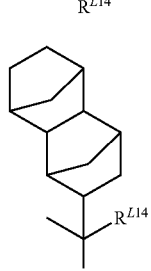
(A-3)-16

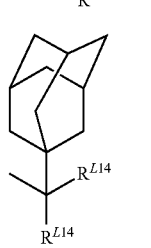
(A-3)-17

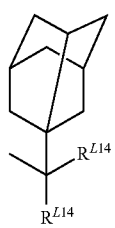
(A-3)-18

Herein $R^{L14}$ is each independently a straight, branched or cyclic $C_1$-$C_8$ alkyl group or $C_6$-$C_{20}$ aryl group, typically phenyl or naphthyl, $R^{L15}$ and $R^{L17}$ each are hydrogen or a straight, branched or cyclic $C_1$-$C_{20}$ alkyl group, and $R^{L16}$ is a $C_6$-$C_{20}$ aryl group, typically phenyl.

The polymer may be crosslinked within the molecule or between molecules with a group $R^{L18}$ which is a di- or multi-valent alkylene or arylene group, as shown by the following formulae (A-3)-19 and (A-3)-20.

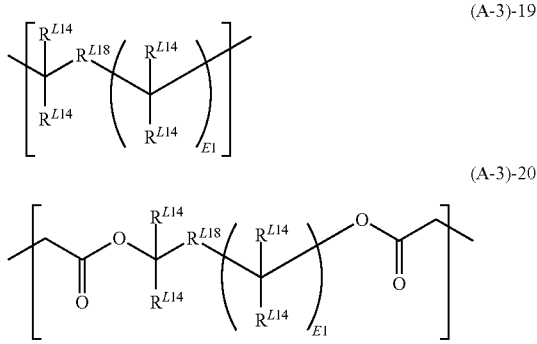

(A-3)-19

(A-3)-20

Herein $R^{L14}$ is as defined above, $R^{L18}$ is a straight, branched or cyclic $C_1$-$C_{20}$ alkylene group or arylene group, typically phenylene, which may contain a heteroatom such as oxygen, sulfur or nitrogen, and El is an integer of 1 to 3.

The method of introducing the acid labile group $R^3$ as illustrated in formula (2) includes a method of introducing at the stage of the monomer having formula (1), or a method of polymerizing a monomer having a phenolic hydroxyl group into a polymer and introducing the acid labile group into the polymer. The introduction of the acid labile group at the monomer stage has the advantage of possible control of a minute amount of the acid labile group introduced. Also in a common practice, an acid labile group of tertiary ester type is introduced at the monomer stage, and an acid labile group of acetal type is introduced at the polymer stage.

In a preferred embodiment, the polymer comprising recurring units (a) having an acid labile group as represented by formula (2) further comprises recurring units (b) having an adhesive group selected from among hydroxyl group, lactone ring, ether group, ester group, carbonyl group, cyano group, cyclic —O—C(=O)—S— and cyclic —O—C(=O)—NH—. The recurring units (b) may be of one type or a mixture of two or more types. Fractions a and b of recurring units (a) and (b) are in the range: 0<a≤1.0, 0≤b<1.0, and 0.05≤a+b≤1.0.

Of the recurring units (b), those units having a phenolic hydroxyl group are preferred since they have a sensitizing effect in the EB and EUV lithography. The recurring unit having a phenolic hydroxyl group is preferably at least one of recurring units (b1) to (b8) as represented by the general formula (3).

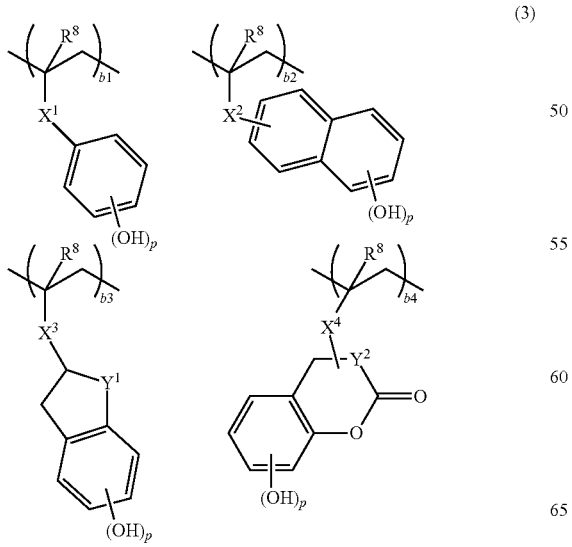

(3)

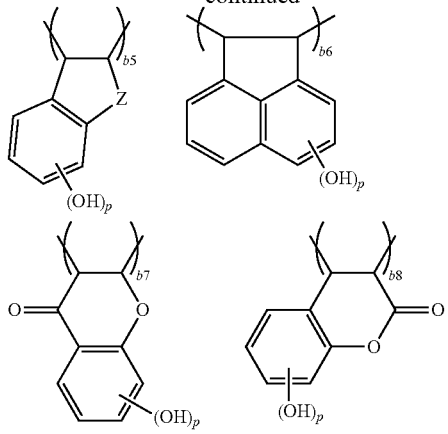

Herein $R^8$ is hydrogen or methyl, $X^1$ and $X^2$ are a single bond or a group —C(=O)—O—$R^9$—, $X^3$ and $X^4$ are a group —C(=O)—O—$R^9$—. $R^9$ is a single bond or $C_1$-$C_{10}$ straight, branched or cyclic alkylene. $Y^1$ and $Y^2$ are methylene or ethylene, Z is methylene, oxygen or sulfur atom, p is 1 or 2, b1 to b8 are positive numbers in the range: 0≤b1<1.0, 0≤b2<1.0, 0≤b3<1.0, 0≤b4<1.0, 0≤b5<1.0, 0≤b6<1.0, 0≤b7<1.0, 0≤b8<1.0, and b1+b2+b3+b4+b5+b6+b7+b8=b.

Examples of suitable monomers from which the recurring units (b1) to (b8) having a phenolic hydroxyl group are derived are given below.

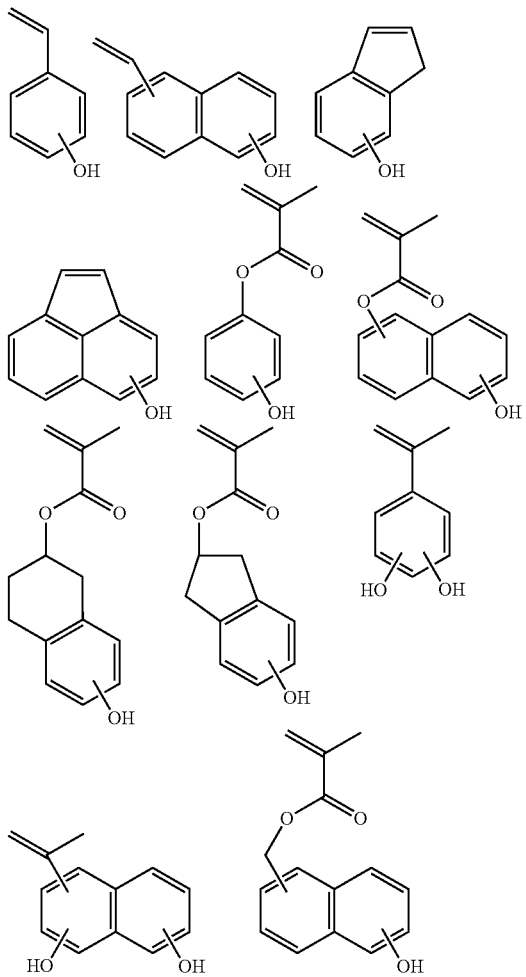

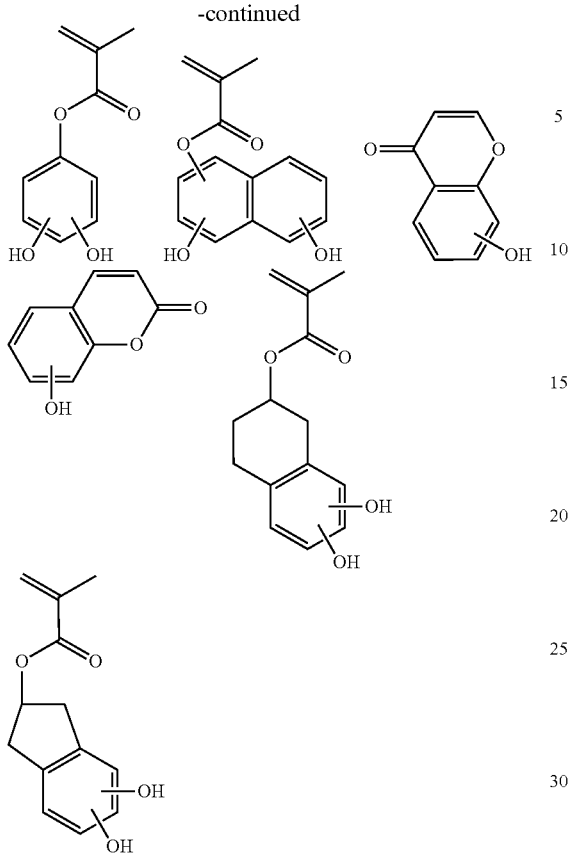
Examples of suitable monomers from which the recurring units (b) having an adhesive group selected from among hydroxyl group (other than phenolic hydroxyl group), lactone ring, ether group, ester group, carbonyl group, cyano group, cyclic —O—C(=O)—S— and cyclic —O—C(=O)—NH— are derived are given below.
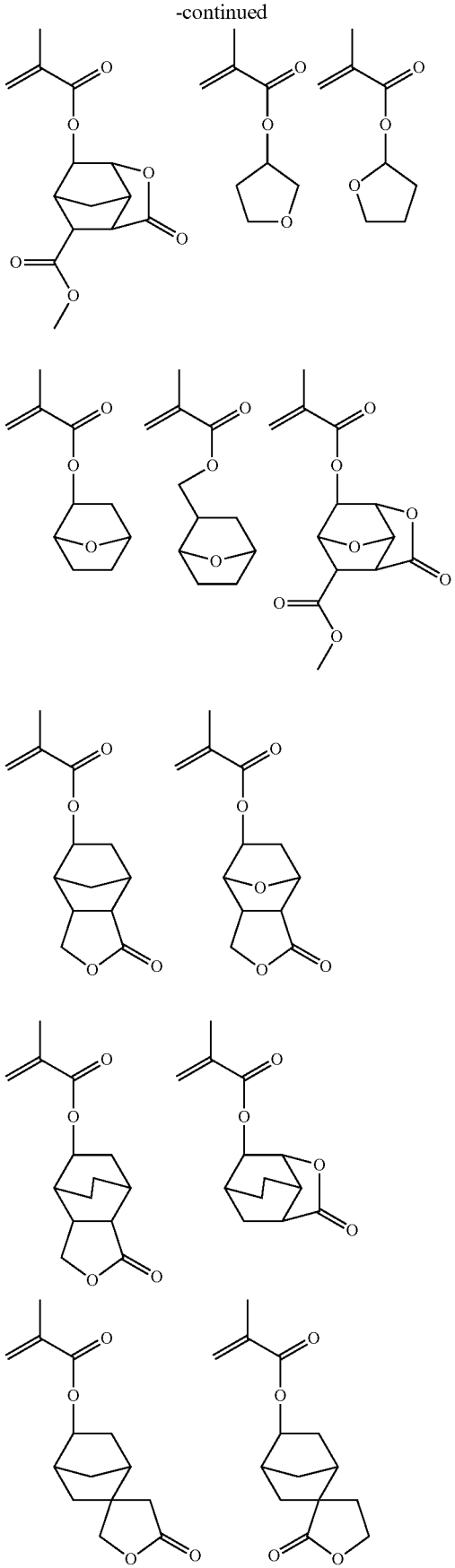

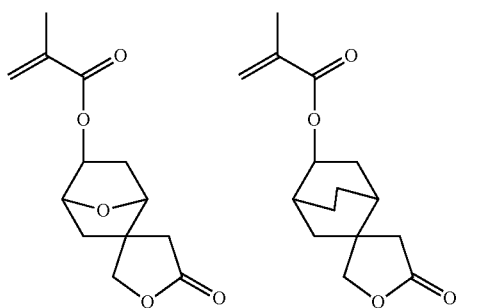
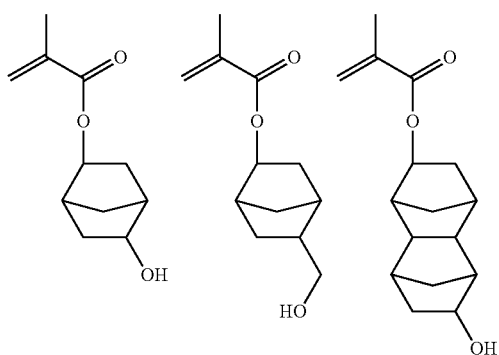
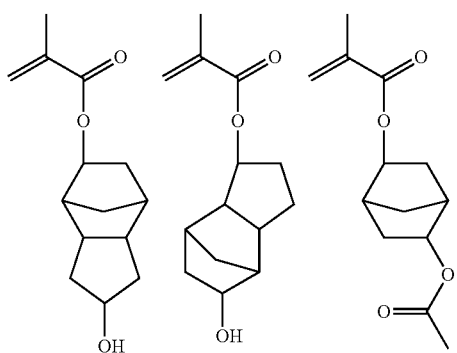
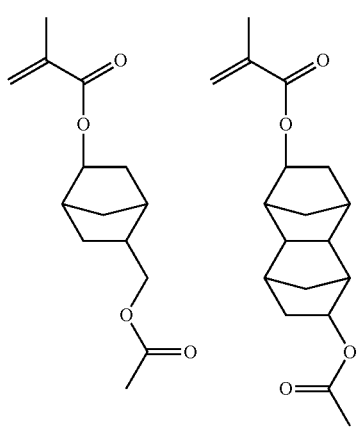
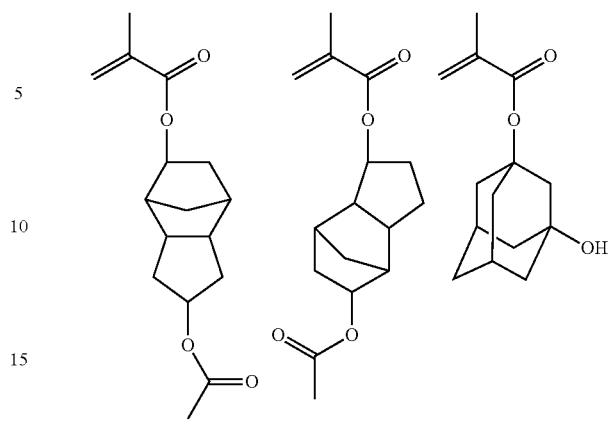
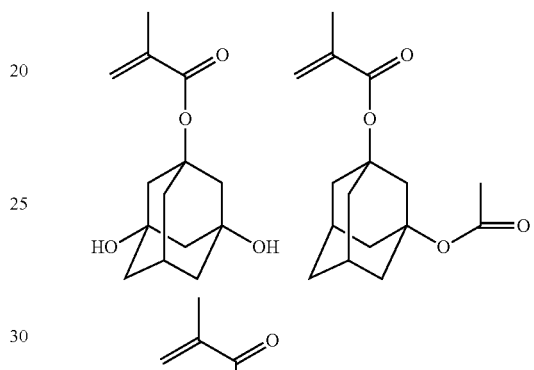
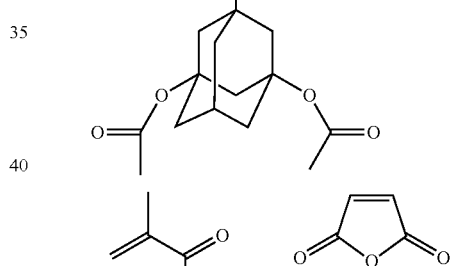
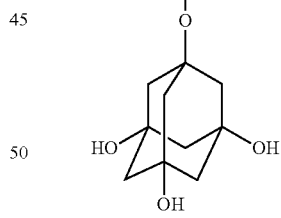
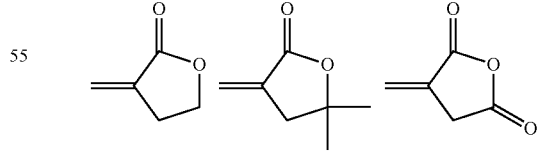
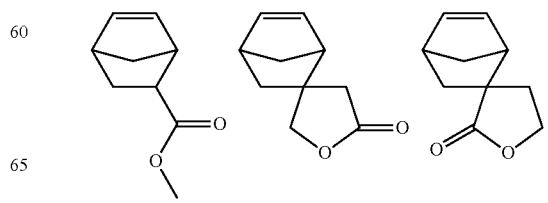

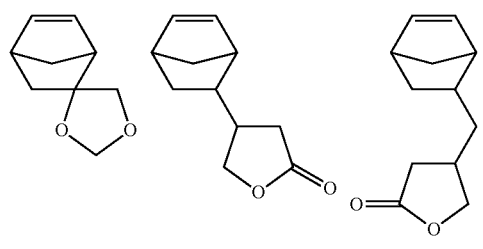
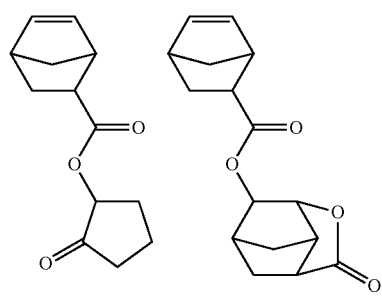
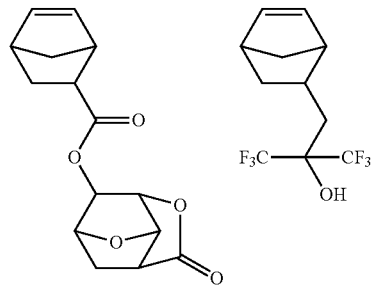
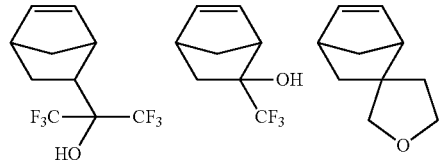
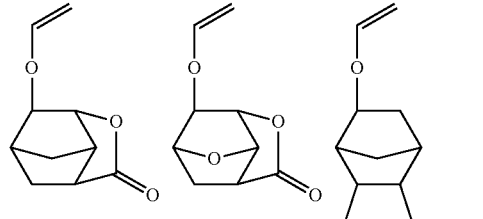
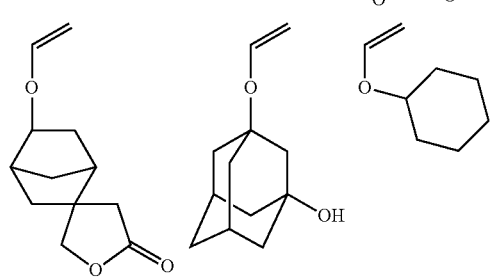
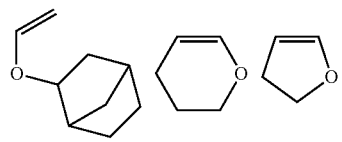
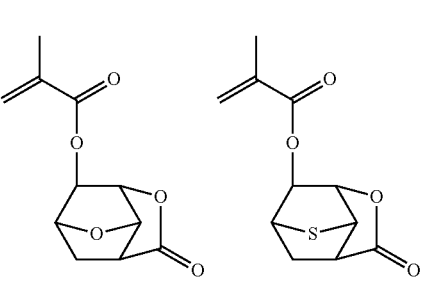
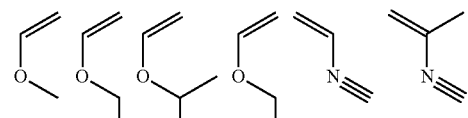
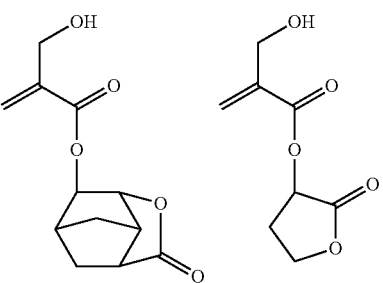
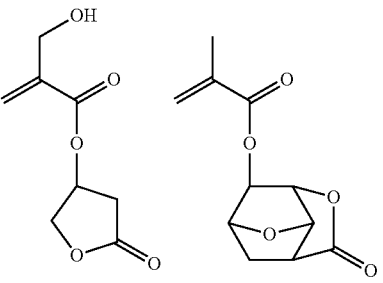
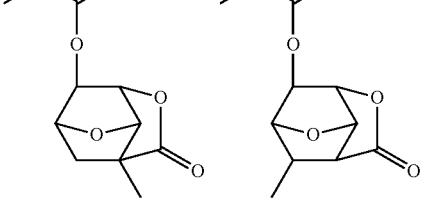
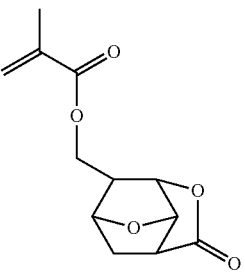

-continued
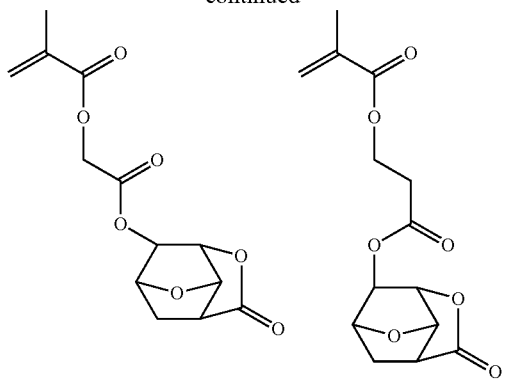
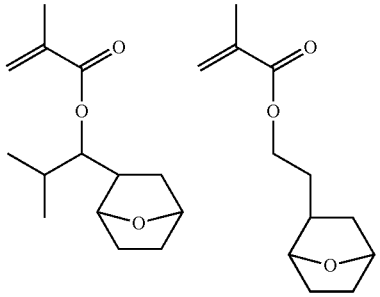
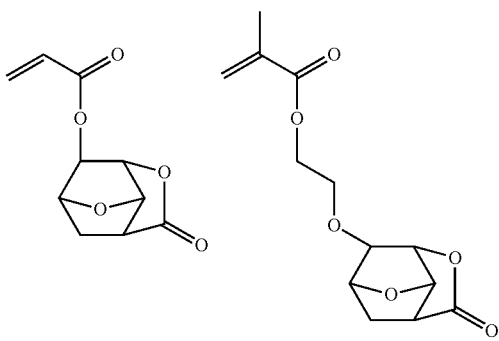
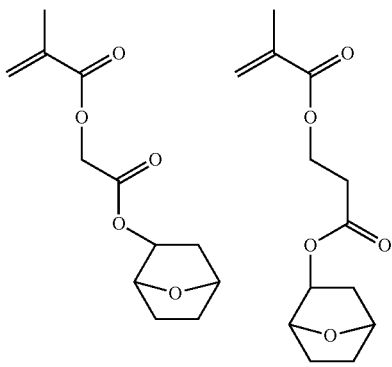
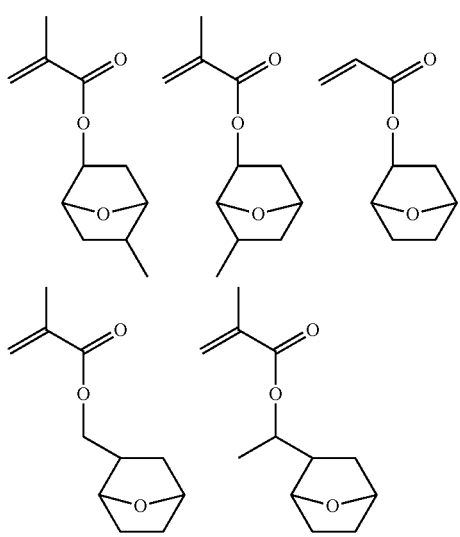
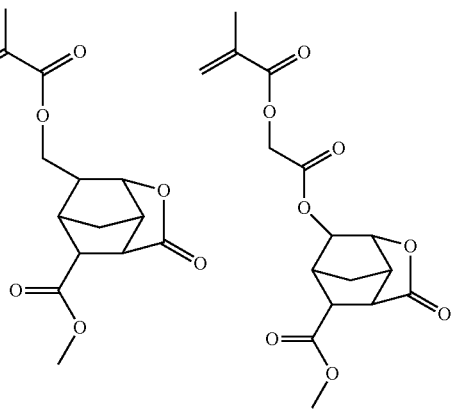

37
-continued
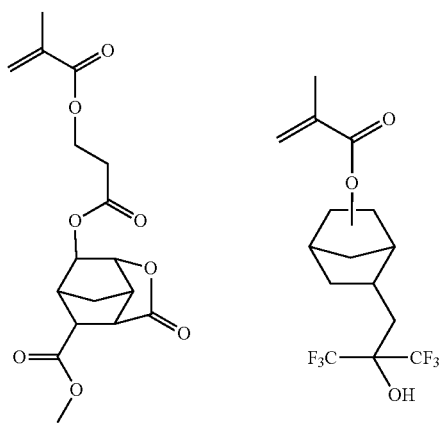
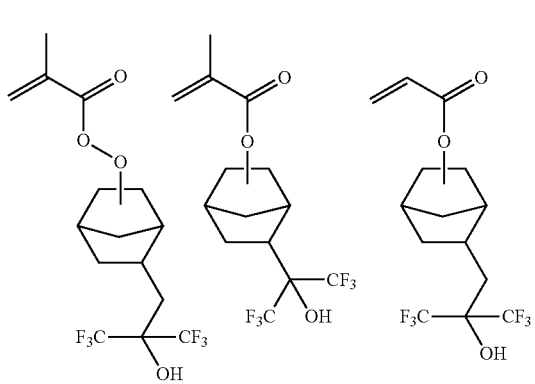
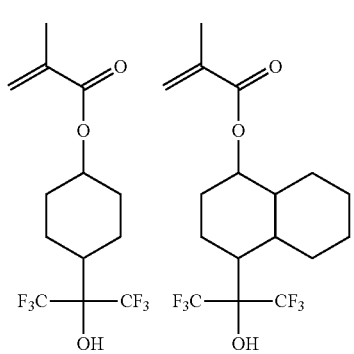
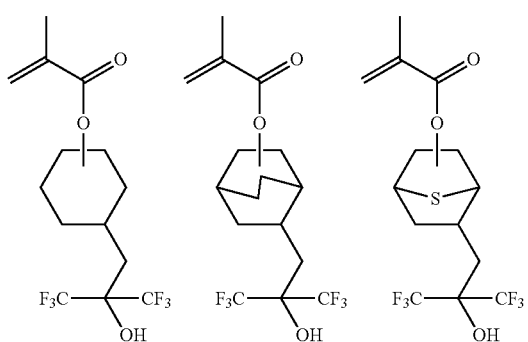
38
-continued
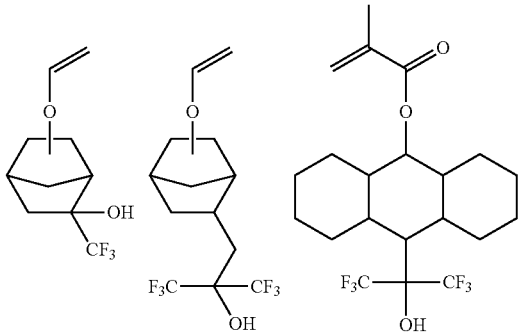
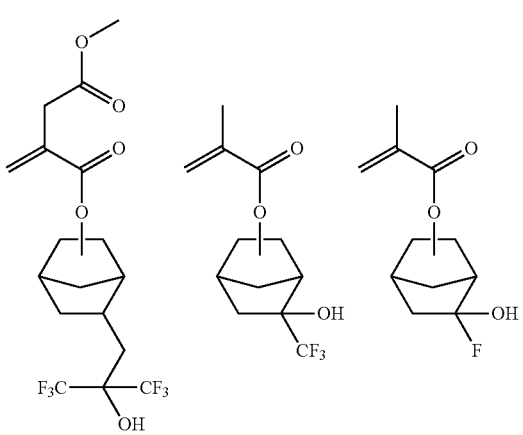
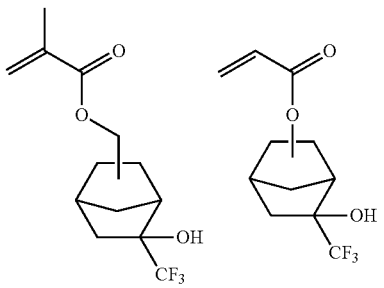
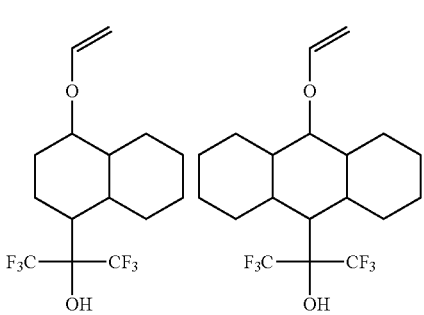

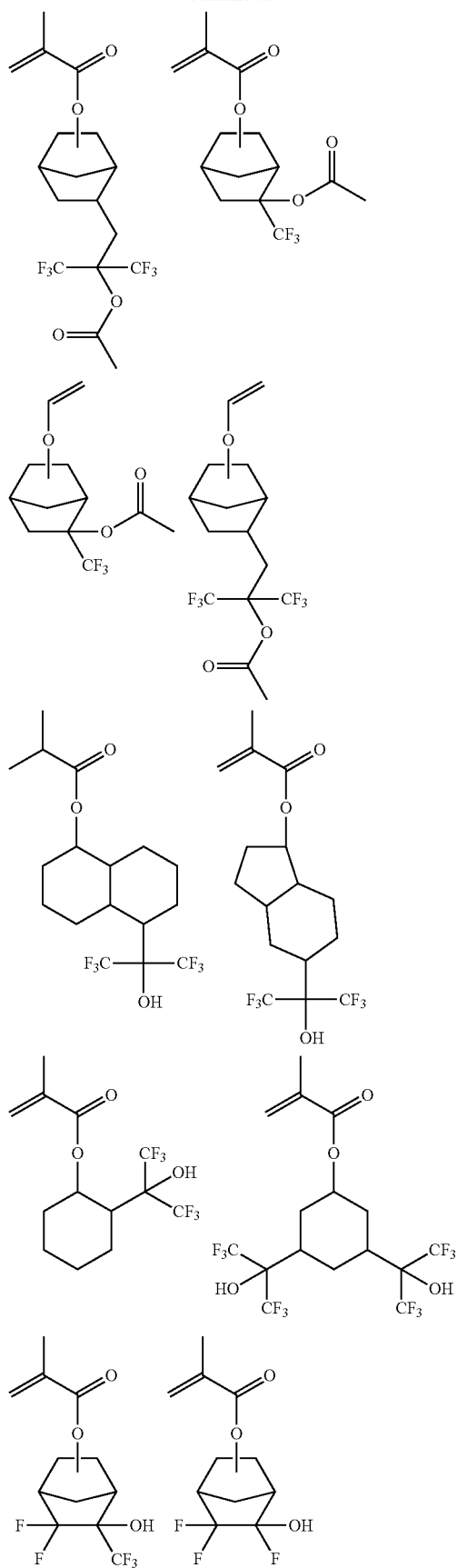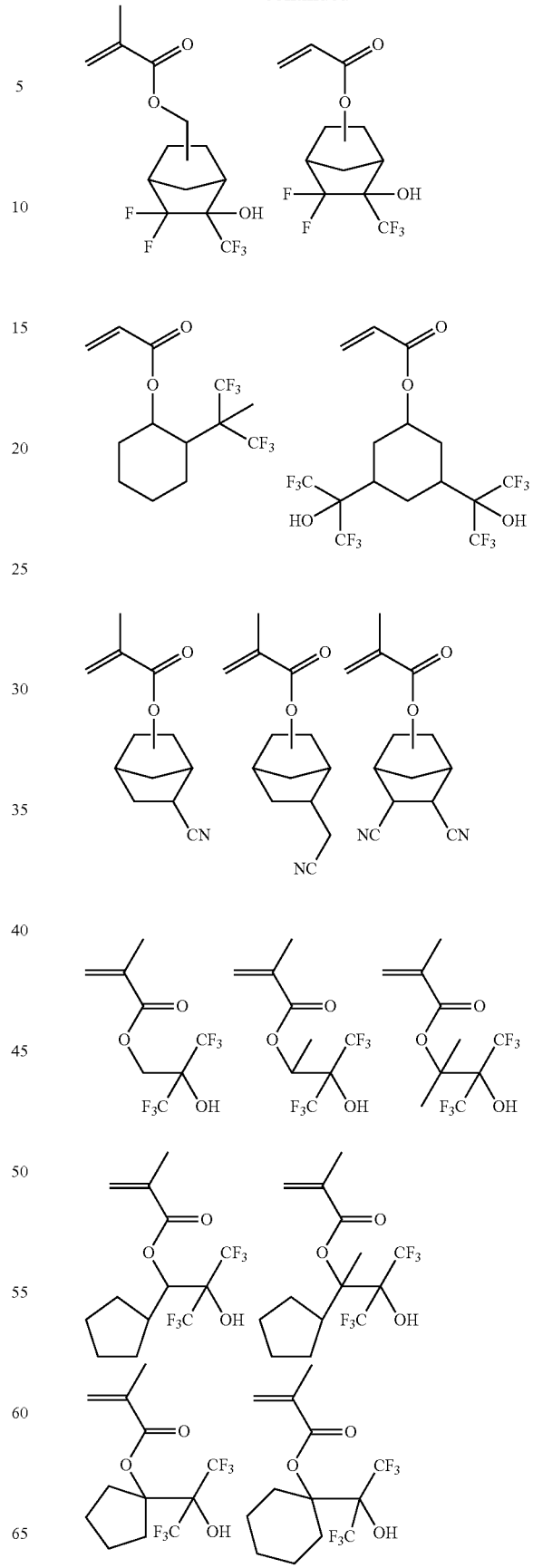

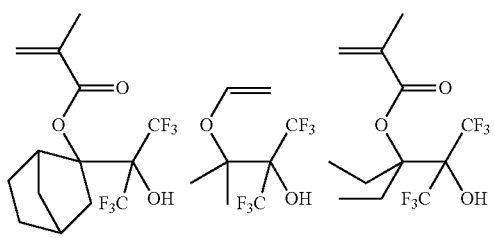
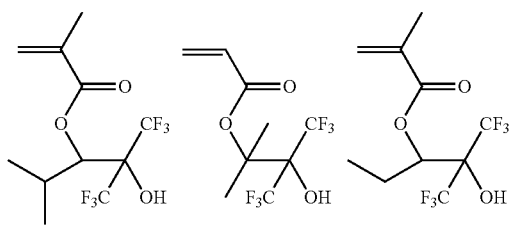
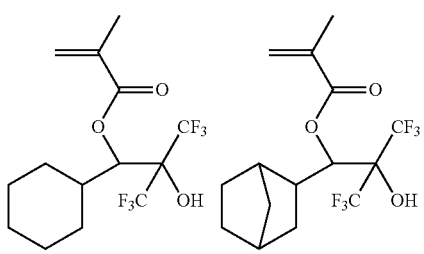
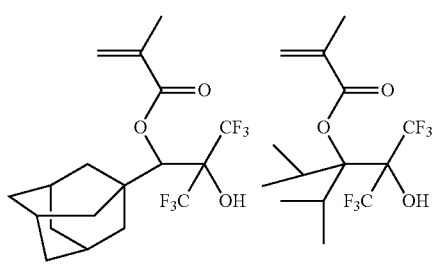
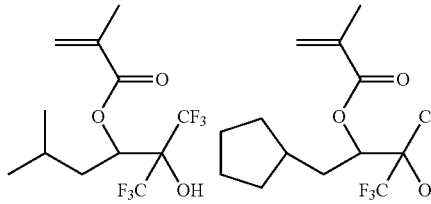
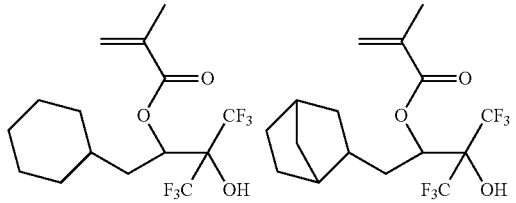
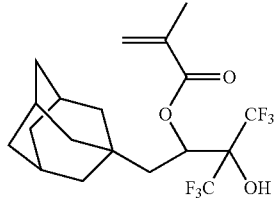
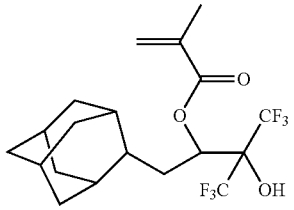
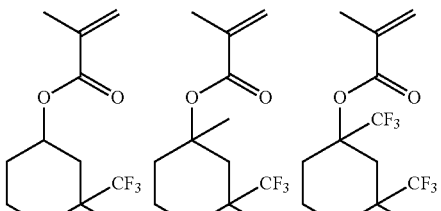
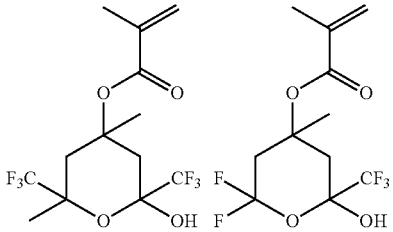
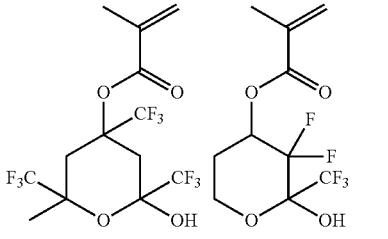
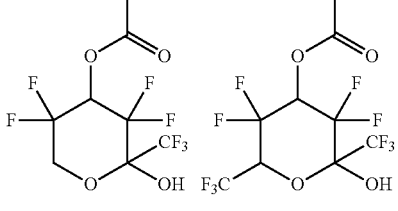
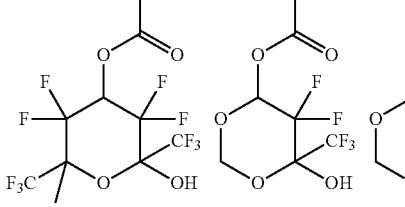
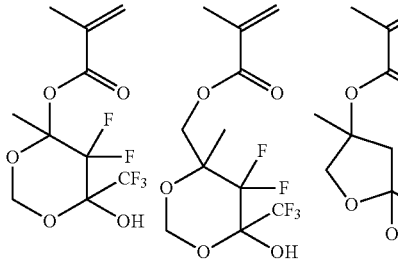

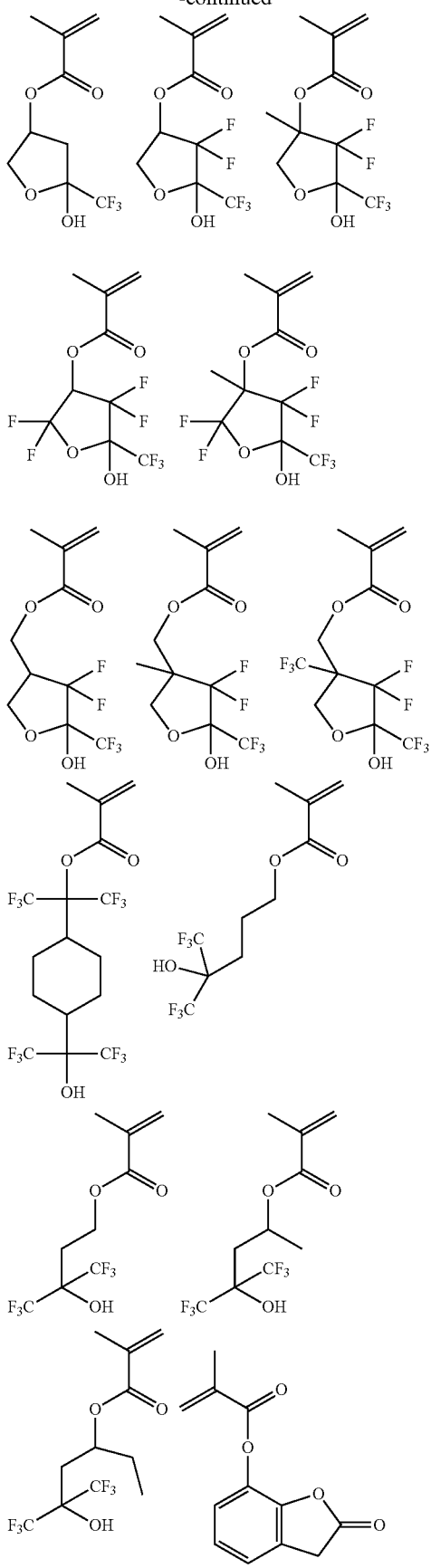
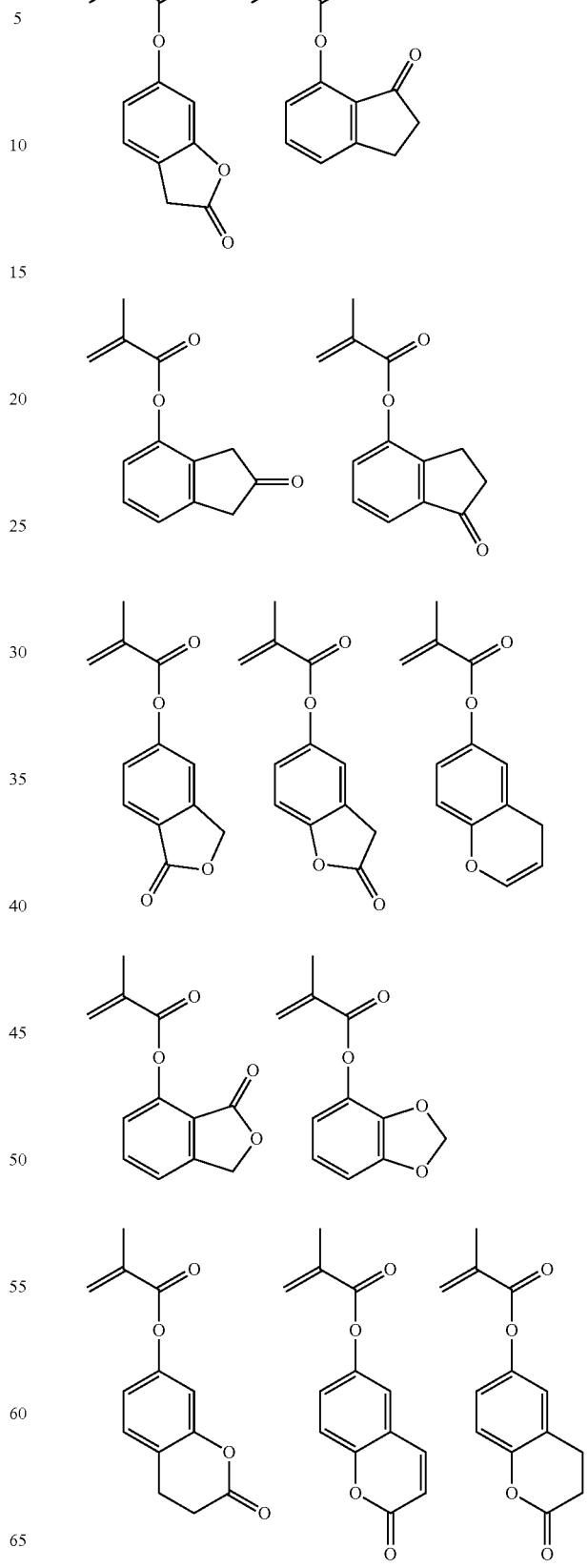

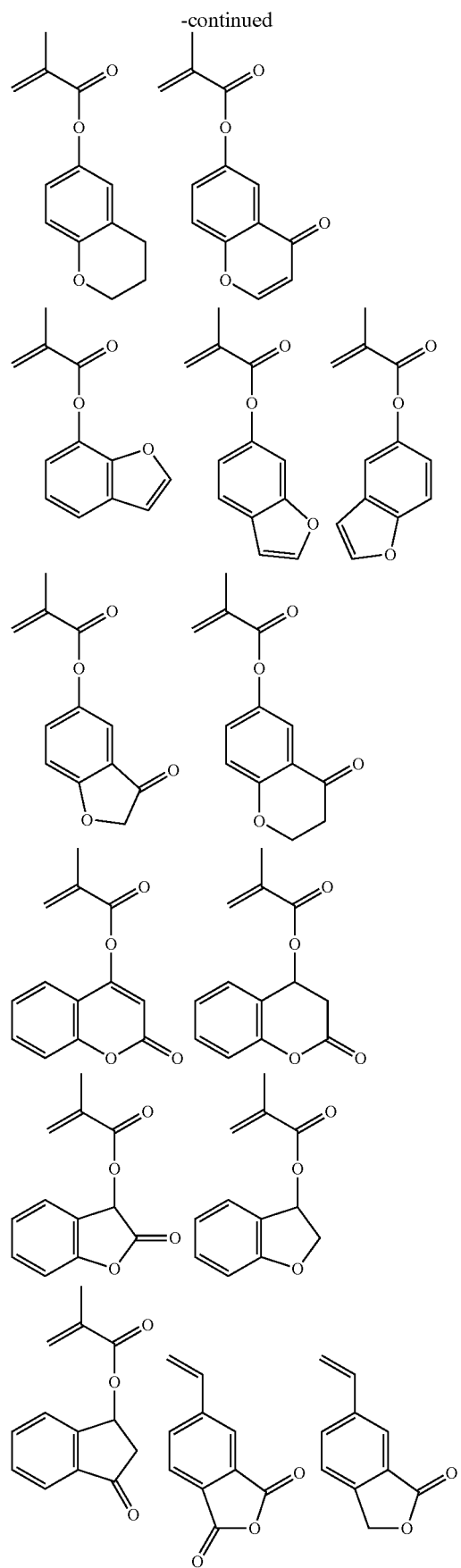
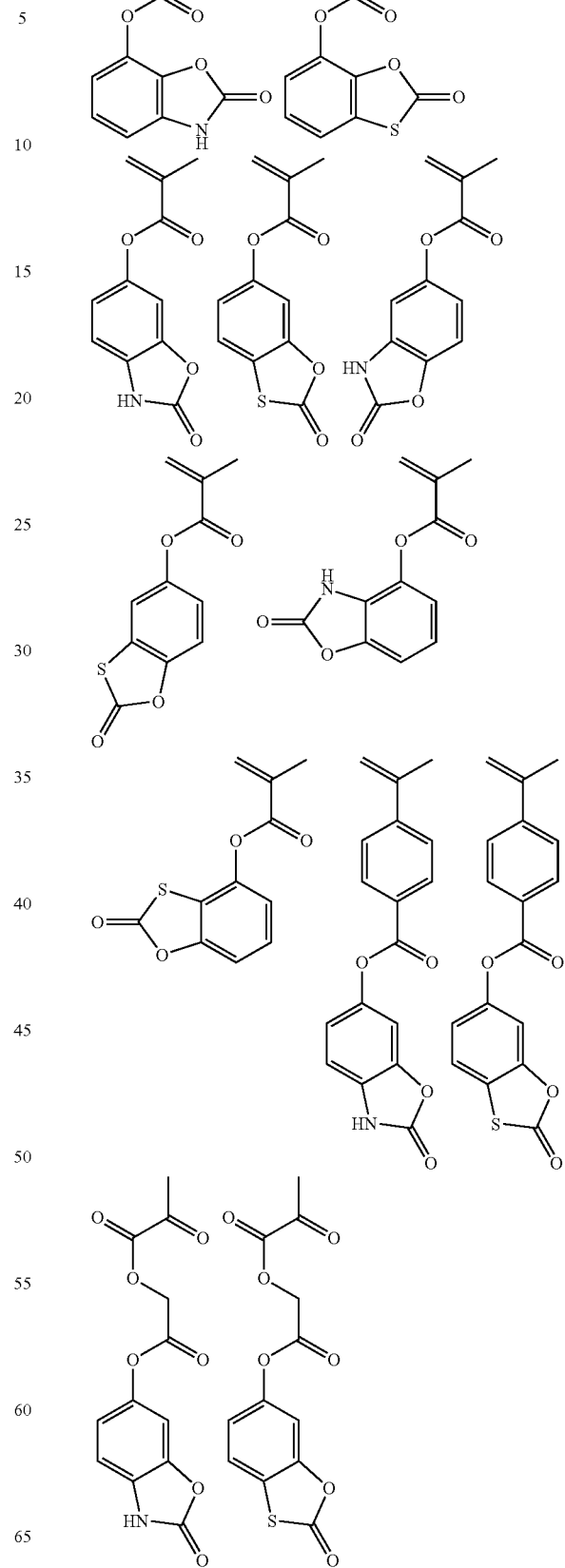

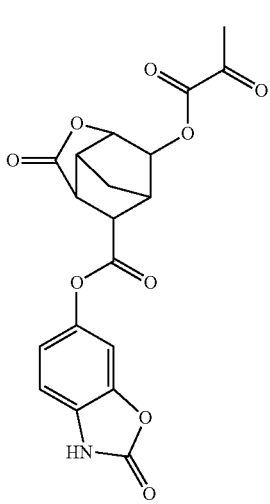

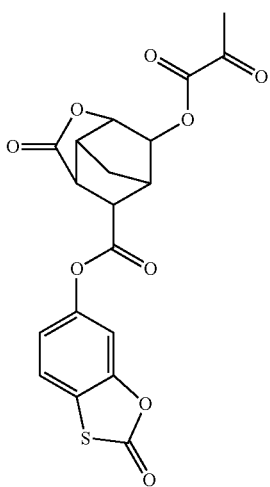

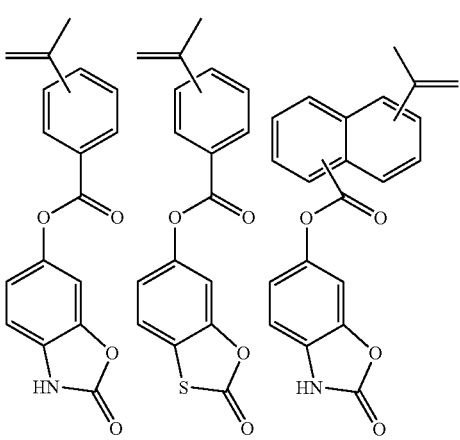

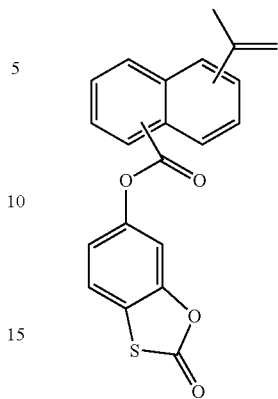

In the case of a monomer having a hydroxyl group, the hydroxyl group may be replaced by an acetal group susceptible to deprotection with acid, typically ethoxyethoxy, prior to polymerization, and the polymerization be followed by deprotection with weak acid and water. Alternatively, the hydroxy group may be replaced by an acetyl, formyl, pivaloyl or similar group prior to polymerization, and the polymerization be followed by alkaline hydrolysis.

In another preferred embodiment, the polymer has further copolymerized therein recurring units (c) of at least one type selected from units (c1) to (c5) of indene, acenaphthylene, chromone, coumarin, and norbornadiene, or derivatives thereof, represented by the general formula (4).

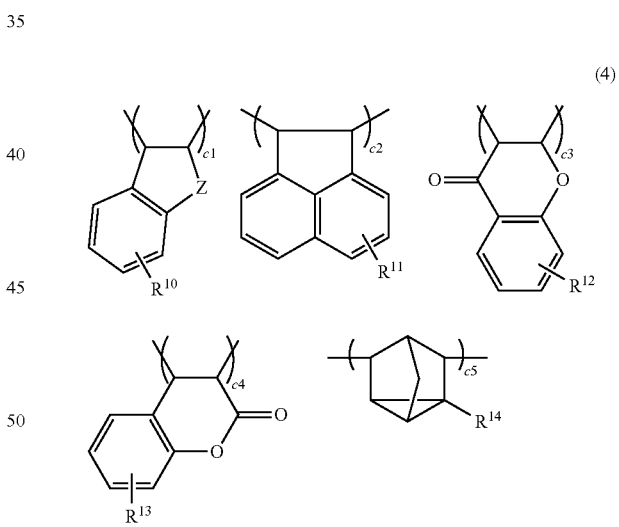

Herein $R^{10}$ to $R^{14}$ are each independently selected from among hydrogen, $C_1$-$C_{30}$ alkyl, $C_1$-$C_{30}$ alkyl wherein some or all carbon-bonded hydrogen atoms are substituted by halogen atoms, $C_1$-$C_8$ alkoxy, $C_1$-$C_8$ alkanoyl, $C_2$-$C_8$ alkoxycarbonyl, $C_6$-$C_{10}$ aryl, halogen, and 1,1,1,3,3,3-hexafluoro-2-propanol group, and Z is methylene, oxygen or sulfur, c1 to c5 are positive numbers in the range: $0 \leq c1 < 1.0$, $0 \leq c2 < 1.0$, $0 \leq c3 < 1.0$, $0 \leq c4 < 1.0$, $0 \leq c5 < 1.0$, and $0 < c1+c2+c3+c4+c5 < 1.0$.

Examples of suitable monomers from which recurring units (c1) to (c5) are derived are given below.

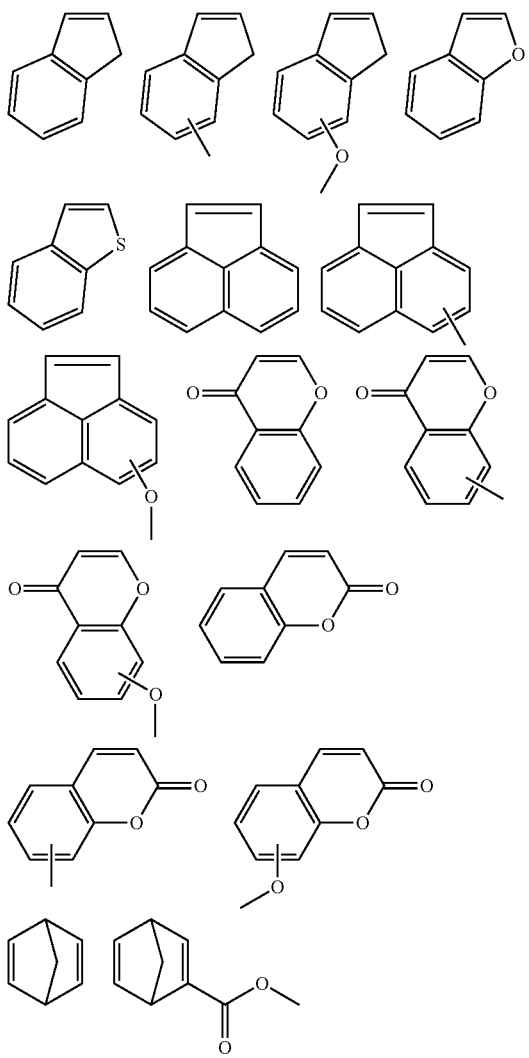

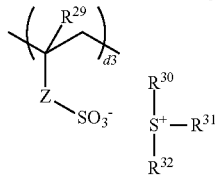

In a further preferred embodiment, the polymer may further comprise recurring units (d) derived from an acid generator in the form of a polymerizable olefin-containing onium salt. JP-A H04-230645, JP-A 2005-084365, and JP-A 2006-045311 disclose polymerizable olefin-containing sulfonium salts capable of generating a specific sulfonic acid and similar iodonium salts. JP-A 2006-178317 discloses a sulfonium salt having sulfonic acid directly attached to the main chain.

In this embodiment, the polymer may further comprise recurring units (d) of at least one type selected from recurring units (d1) to (d3) having a sulfonium salt, represented by the general formula (5).

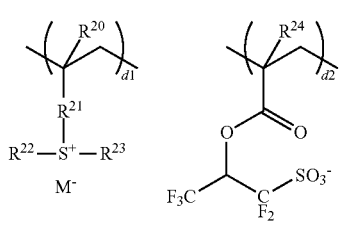

Herein $R^{20}$, $R^{24}$ and $R^{29}$ each are hydrogen or methyl. $R^{21}$ is a single bond, phenylene, —O—$R^{28}$—, or —C(=O)—Y—$R^{28}$— wherein Y is oxygen or NH and $R^{28}$ is a straight, branched or cyclic $C_1$-$C_6$ alkylene group, alkenylene group or phenylene group, which may contain a carbonyl (—CO—), ester (—COO—), ether (—O—) or hydroxyl group. $R^{22}$, $R^{23}$, $R^{25}$, $R^{26}$, $R^{27}$, $R^{30}$, $R^{31}$, and $R^{32}$ are each independently a straight, branched or cyclic $C_1$-$C_{12}$ alkyl group which may contain a carbonyl, ester or ether group, or a $C_6$-$C_{12}$ aryl group, $C_7$-$C_{20}$ aralkyl group, or thiophenyl group. Z is a single bond, methylene, ethylene, phenylene, fluorinated phenylene, —O—$R^{33}$—, or —C(=O)—$Z^1$—$R^{33}$— wherein $Z^1$ is oxygen or NH and $R^{33}$ is a straight, branched or cyclic $C_1$-$C_6$ alkylene group, alkenylene group or phenylene group, which may contain a carbonyl, ester, ether or hydroxyl group. $M^-$ is a non-nucleophilic counter ion. Molar fractions d1 to d3 are in the range: $0 \leq d1 \leq 0.5$, $0 \leq d2 \leq 0.5$, $0 \leq d3 \leq 0.5$, and $0 < d1+d2+d3 \leq 0.5$.

Examples of the non-nucleophilic counter ion represented by $M^-$ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imidates such as bis(trifluoromethylsulfonyl)imide, bis(perfluoroethylsulfonyl)imide and bis(perfluorobutylsulfonyl)imide; methidates such as tris(trifluoromethylsulfonyl)methide and tris(perfluoroethylsulfonyl)methide.

The attachment of an acid generator to the polymer main chain is effective in restraining acid diffusion, thereby preventing a reduction of resolution due to blur by acid diffusion. Also edge roughness (LER or LWR) is improved since the acid generator is uniformly dispersed.

While the polymer according to the invention comprises recurring units (a) having an acid labile group as essential units, it may further comprise recurring units (e) of (meth)acrylate having substituted thereon an acid labile group $R^{41}$ and/or recurring units (f) of hydroxystyrene having substituted thereon an acid labile group $R^{43}$, as represented by the following general formula (7).

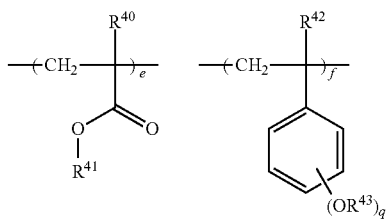

Herein $R^{40}$ and $R^{42}$ each are hydrogen or methyl, $R^{41}$ and $R^{43}$ each are an acid labile group, and q is 1 or 2.

The acid labile groups $R^{41}$ and $R^{43}$ in formula (7) may be selected from the acid labile groups of formulae (A-1), (A-2), and (A-3).

Preferably, $R^{41}$ in recurring unit (e) is an acid labile group of formula (A-3). In this embodiment, the preferred recurring units (e) are recurring units of (meth)acrylate having an exo-form structure represented by the following formula (A-3)-21.

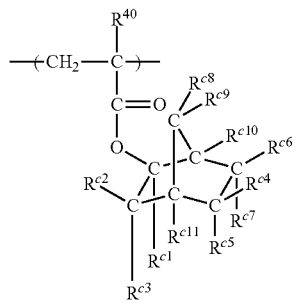

(A-3)-21

Herein, $R^{40}$ is as defined above; $R^{c1}$ is a straight, branched or cyclic $C_1$-$C_8$ alkyl group or $C_6$-$C_{20}$ aryl group in which some or all carbon-bonded hydrogen atoms may be substituted by halogen atoms; $R^{c2}$ to $R^{c7}$, $R^{c10}$ and $R^{c11}$ are each independently hydrogen or a monovalent $C_1$-$C_{15}$ hydrocarbon group which may contain a heteroatom; and $R^{c8}$ and $R^{c9}$ are hydrogen. Alternatively, a pair of $R^{c2}$ and $R^{c3}$, $R^{c4}$ and $R^{c6}$, $R^{c4}$ and $R^{c7}$, $R^{c5}$ and $R^{c7}$, $R^{c5}$ and $R^{c11}$, $R^{c6}$ and $R^{c10}$, $R^{c8}$ and $R^{c9}$, or $R^{c9}$ and $R^{c10}$ may bond together to form a ring with the carbon atom to which they are attached, and in that event, each of ring-forming $R^{c2}$ and $R^{c3}$, $R^{c4}$ and $R^{c6}$, $R^{c4}$ and $R^{c7}$, $R^{c5}$ and $R^{c7}$, $R^{c5}$ and $R^{c11}$, $R^{c6}$ and $R^{c10}$, $R^{c8}$ and $R^{c9}$, or $R^{c9}$ and $R^{c10}$ is a divalent $C_1$-$C_{15}$ hydrocarbon group which may contain a heteroatom. Also, a pair of $R^{c2}$ and $R^{c11}$, $R^{c8}$ and $R^{c11}$, or $R^{c4}$ and $R^{c6}$ which are attached to vicinal carbon atoms may bond together directly to form a double bond. The formula also represents an enantiomer.

The ester form monomers from which recurring units having an exo-form structure represented by formula (A-3)-21 are derived are described in U.S. Pat. No. 6,448,420 (JP-A 2000-327633). Illustrative non-limiting examples of suitable monomers are given below.

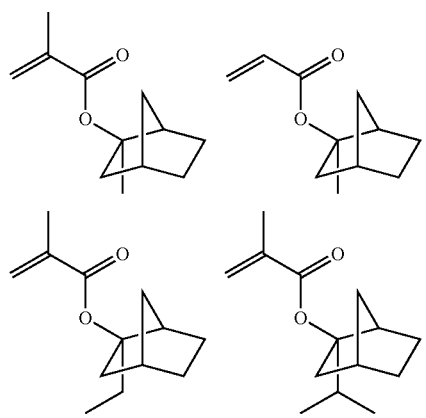

-continued

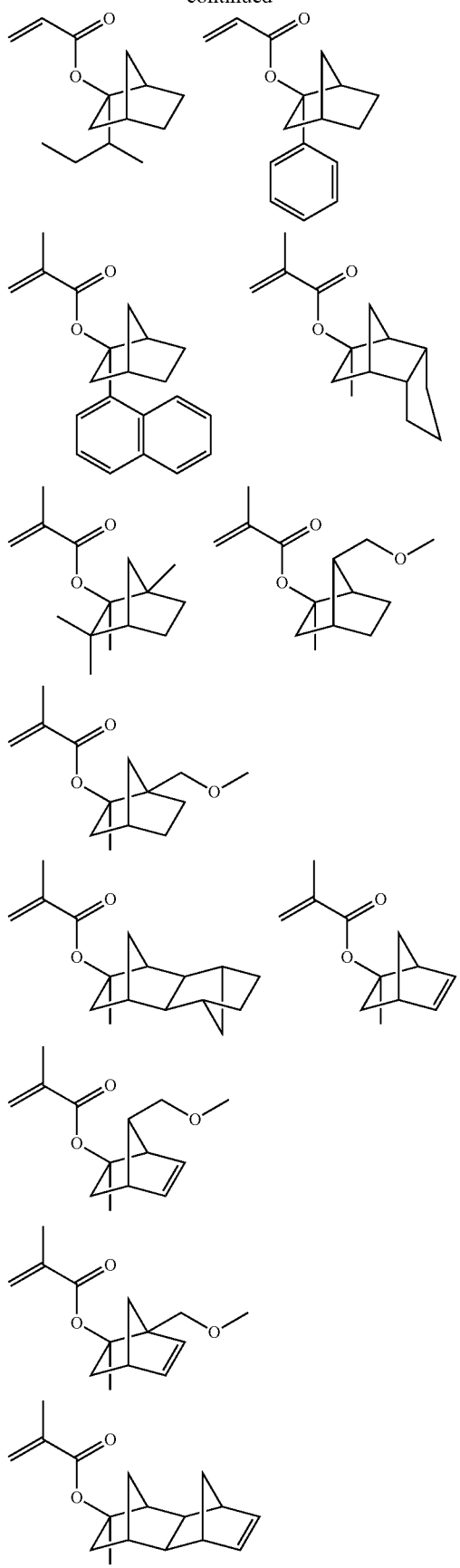

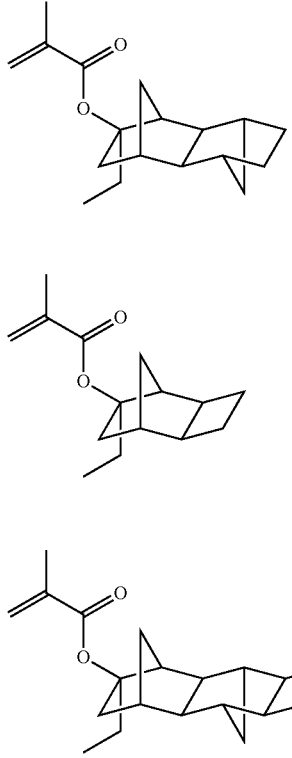

Other preferred examples of the recurring units (e) include recurring units derived from (meth)acrylates having furandiyl, tetrahydrofurandiyl or oxanorbornanediyl substituted thereon, as represented by the following formula (A-3)-22.

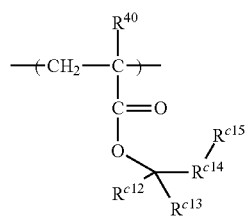

(A-3)-22

Herein, $R^{40}$ is as defined above. $R^{c12}$ and $R^{c13}$ are each independently a monovalent, straight, branched or cyclic $C_1$-$C_{10}$ hydrocarbon group. Alternatively, $R^{c12}$ and $R^{c13}$ may bond together to form an aliphatic hydrocarbon ring with the carbon atom to which they are attached, and each of $R^{c12}$ and $R^{c13}$ is a divalent $C_1$-$C_{10}$ hydrocarbon group, typically alkylene, when they form a ring. $R^{c14}$ is a divalent group selected from furandiyl, tetrahydrofurandiyl and oxanorbornanediyl. $R^{c15}$ is hydrogen or a monovalent, straight, branched or cyclic $C_1$-$C_{10}$ hydrocarbon group which may contain a heteroatom.

Examples of the monomers from which the recurring units of methacrylates substituted with an acid labile group having furandiyl, tetrahydrofurandiyl or oxanorbornanediyl are derived are shown below, but not limited thereto. Note that Me is methyl and Ac is acetyl.

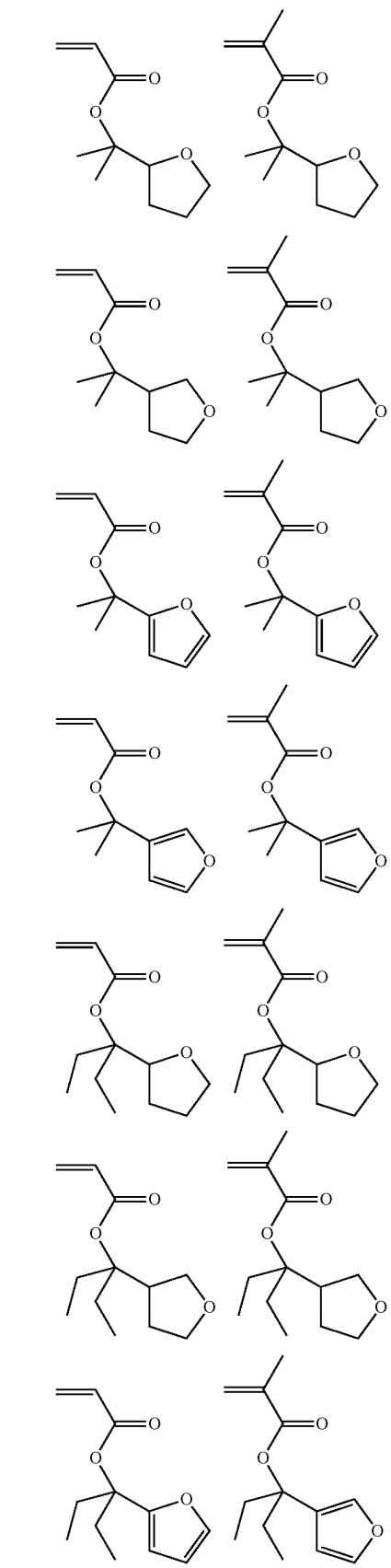

-continued
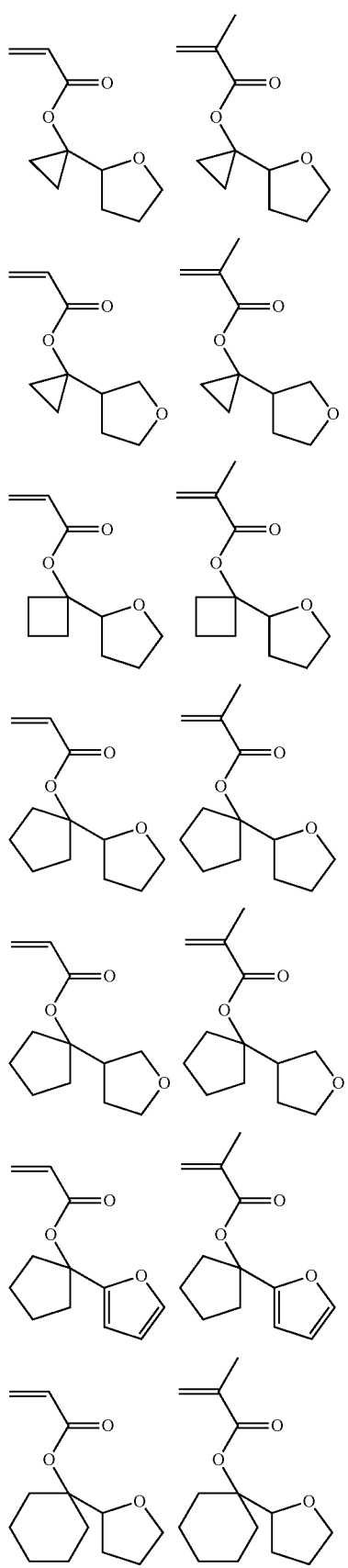
-continued
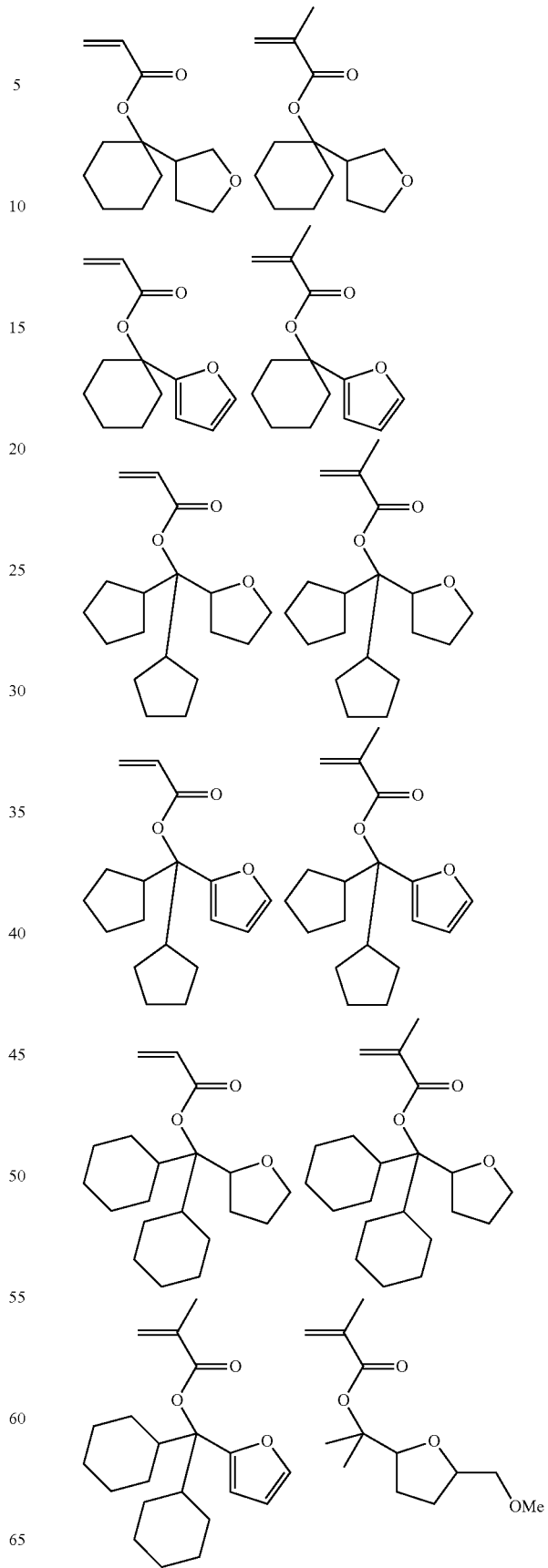

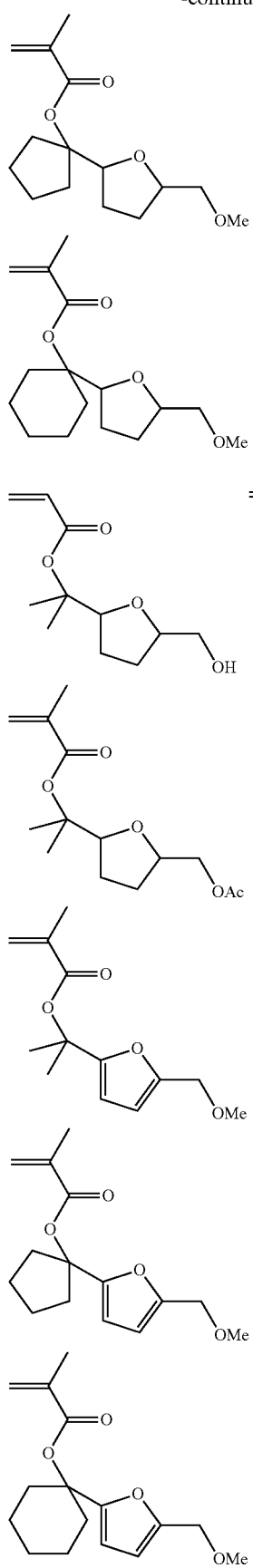
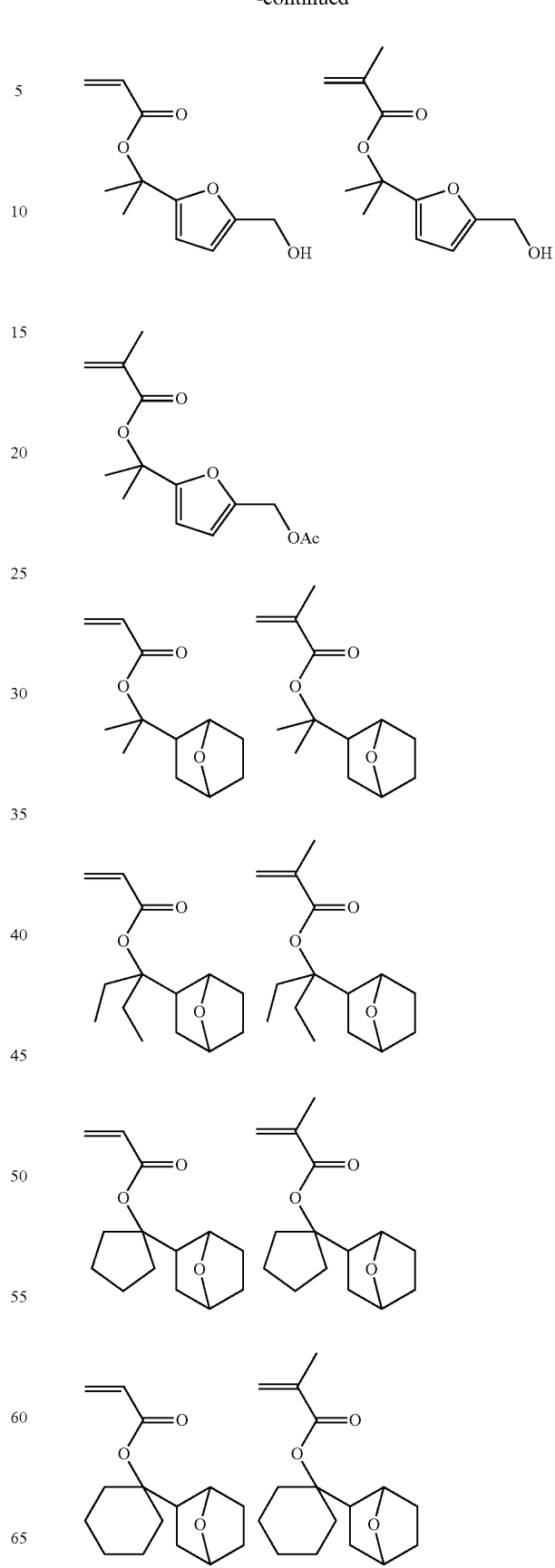

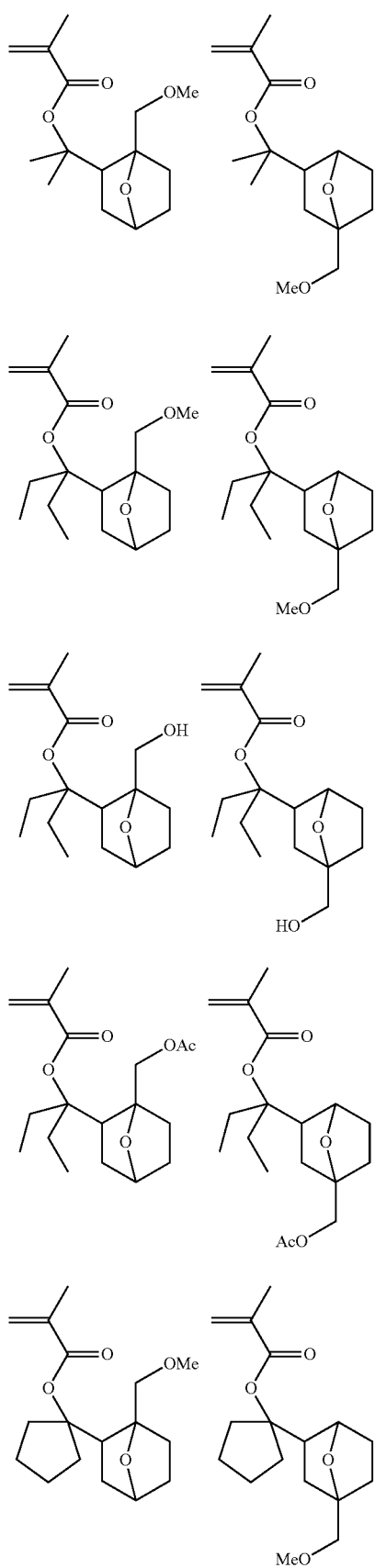

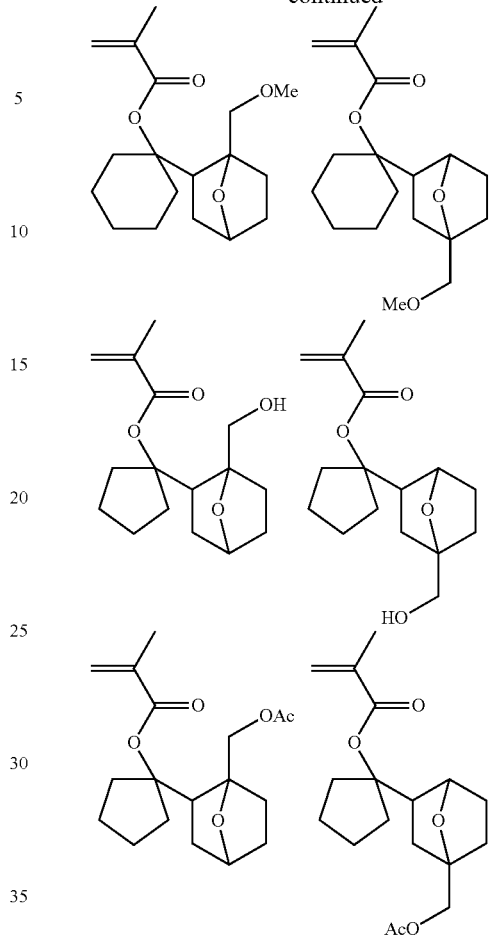

Besides the recurring units (a) to (f), additional recurring units (g) may be copolymerized in the polymer, which include recurring units derived from styrene, vinylnaphthalene, vinylanthracene, vinylpyrene, methyleneindane, and the like.

The polymer used herein may be synthesized by any desired methods, for example, by dissolving one or more monomers selected from the monomers to form the recurring units (a) to (g) in an organic solvent, adding a radical polymerization initiator thereto, and effecting heat polymerization. Examples of the organic solvent which can be used for polymerization include toluene, benzene, tetrahydrofuran, diethyl ether and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is typically 2 to 100 hours, preferably 5 to 20 hours.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis as mentioned above, for thereby converting the polymer product to polyhydroxystyrene or hydroxypolyvinylnaphthalene. For alkaline hydrolysis, a base such as aqueous ammonia or triethylamine may be used. The reaction temperature is typically −20° C. to 100° C., preferably 0° C. to 60° C., and the reaction time is typically 0.2 to 100 hours, preferably 0.5 to 20 hours.

In the copolymer, recurring units (a) to (g) may be incorporated in the following molar fraction:

$0<a\leq1.0$, preferably $0<a<1.0$, more preferably $0.05\leq a\leq 0.8$, and even more preferably $0.08\leq a\leq 0.7$;

$0\leq b<1.0$, preferably $0<b<1.0$, more preferably $0.1\leq b\leq 0.9$, and even more preferably $0.15\leq b\leq 0.8$;

$0\leq c<1.0$, preferably $0\leq c\leq 0.9$, and more preferably $0\leq c\leq 0.8$;

$0\leq d\leq 0.5$, preferably $0\leq d\leq 0.4$, and more preferably $0\leq d\leq 0.3$;

$0\leq e\leq 0.5$, preferably $0\leq e\leq 0.4$, and more preferably $0\leq e\leq 0.3$;

$0\leq f\leq 0.5$, preferably $0\leq f\leq 0.4$, and more preferably $0\leq f\leq 0.3$;

$0\leq g\leq 0.5$, preferably $0\leq g\leq 0.4$, and more preferably $0\leq g\leq 0.3$;

preferably $0.2\leq a+b+c\leq 1.0$, more preferably $0.3\leq a+b+c\leq 1.0$; and $a+b+c+d+e+f+g=1$.

The meaning of $a+b+c=1$, for example, is that in a polymer comprising recurring units (a), (b), and (c), the sum of recurring units (a), (b), and (c) is 100 mol % based on the total amount of entire recurring units. The meaning of $a+b+c<1$ is that the sum of recurring units (a), (b), and (c) is less than 100 mol % based on the total amount of entire recurring units, indicating the inclusion of other recurring units.

The polymer serving as the base resin in the resist composition should have a weight average molecular weight (Mw) in the range of 1,000 to 500,000, and preferably 2,000 to 30,000, as measured by gel permeation chromatography (GPC) versus polystyrene standards using tetrahydrofuran as a solvent. With too low a Mw, the resist composition may become less heat resistant. A polymer with too high a Mw may lose alkaline solubility and give rise to a footing phenomenon after pattern formation.

If a multi-component copolymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the multi-component copolymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, molecular weight or dispersity is acceptable. A blend of one or more inventive polymer and one or more conventional polymer is also acceptable.

Resist Composition

The polymer is advantageously used as a base resin in a positive resist composition, typically chemically amplified positive resist composition. The positive resist composition comprises the polymer defined herein as a base resin and an organic solvent.

Examples of the organic solvent used herein are described in JP-A 2008-111103, paragraphs [0144] to [0145] (U.S. Pat. No. 7,537,880). Exemplary solvents include ketones such as cyclohexanone and methyl-2-n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in admixture. An appropriate amount of the organic solvent used is 50 to 10,000 parts, more preferably 100 to 5,000 parts by weight relative to 100 parts by weight of the base resin.

Preferably the positive resist composition may further comprise a dissolution regulator. Inclusion of a dissolution regulator may lead to an increased difference in dissolution rate between exposed and unexposed areas and a further improvement in resolution. Exemplary dissolution regulators are described in JP-A 2008-122932, paragraphs [0155] to [0178] (US 2008090172). The dissolution regulators may be used alone or in admixture. An appropriate amount of the dissolution regulator is 0 to 50 parts, more preferably 0 to 40 parts by weight relative to 100 parts by weight of the base resin. As long as the amount of the dissolution regulator is up to 50 parts by weight, there is little risk of the pattern film being slimmed to invite a drop of resolution.

The positive resist composition may further include an acid generator in order for the composition to function as a chemically amplified positive resist composition. Typical of the acid generator used herein is a photoacid generator (PAG) capable of generating an acid in response to actinic light or radiation. It is any compound capable of generating an acid upon exposure to high-energy radiation. Suitable photoacid generators include sulfonium salts, iodonium salts, sulfonyldiazomethane, N-sulfonyloxyimide, and oxime-O-sulfonate acid generators. Exemplary acid generators are described in JP-A 2008-111103, paragraphs [0122] to [0142] (U.S. Pat. No. 7,537,880).

An appropriate amount of the acid generator used is 0 to 100 parts, more preferably 0.01 to 100 parts, and even more preferably 0.1 to 80 parts by weight relative to 100 parts by weight of the base resin. As long as the amount of the acid generator is up to 100 parts by weight, the photoresist film maintains a fully high transmittance, minimizing the degradation of resolution. The acid generators may be used alone or in admixture of two or more. The transmittance of the resist film can be controlled by using an acid generator having a low transmittance at the exposure wavelength and adjusting the amount of the acid generator added.

Addition of a basic compound to the positive resist composition holds down the diffusion rate of acid within the resist film, for example, achieving a further improvement in resolution. Examples of the basic compound include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, imide derivatives, and carbamate derivatives as described in JP-A 2008-111103, paragraphs [0146] to [0164], specifically amine compounds having a hydroxyl, ether, ester, lactone, cyano or sulfonic ester group. An appropriate amount of the basic compound used is 0 to 100 parts, and more preferably 0.001 to 50 parts by weight per 100 parts by weight of the base resin.

A surfactant may be added to the positive resist composition. Addition of a surfactant may improve or control the coating characteristics of the resist composition. Exemplary surfactants are described in JP-A 2008-111103, paragraphs [0165] to [0166]. An appropriate amount of the surfactant is 0 to 10 parts, more preferably 0.0001 to 5 parts by weight relative to 100 parts by weight of the base resin.

An acetylene alcohol may be added to the positive resist composition. Exemplary acetylene alcohols are described in JP-A 2008-122932, paragraphs [0179] to [0182] (US 2008090172). An appropriate amount of the acetylene alcohol used is 0 to 2%, more preferably 0.02 to 1% by weight based on the total weight of the resist composition. An amount of up to 2 wt % of the acetylene alcohol minimizes the risk of reducing the resolution of the resist composition.

Also useful are quenchers of polymer type as described in JP-A 2008-239918. The polymeric quencher segregates at the resist surface after coating and thus enhances the rectangularity of resist pattern. When a protective film is applied as is often the case in the immersion lithography, the polymeric quencher is also effective for preventing slimming of resist pattern or rounding of pattern top. The polymeric quencher when used may be added in any desired amount as long as the benefits of the invention are not compromised.

As described above, the inventive polymer is used as a base resin and combined with an organic solvent and any desired components including an acid generator, dissolution regulator, basic compound, and surfactant to formulate a positive resist composition. This positive resist composition has a very high sensitivity in that the dissolution rate in developer of the polymer in exposed areas is accelerated by catalytic reaction. In addition, the resist film has a high dissolution contrast, resolution, exposure latitude, and process adaptability, and provides a good pattern profile after exposure, yet better etching resistance, and minimal proximity bias because of restrained acid diffusion. By virtue of these advantages, the composition is fully useful in commercial application and suited as a pattern-forming material for the fabrication of VLSIs. Particularly when an acid generator is incorporated to formulate a chemically amplified positive resist composition capable of utilizing acid catalyzed reaction, the composition has a higher sensitivity and is further improved in the properties described above.

Process

The positive resist composition, typically chemically amplified positive resist composition comprising a polymer comprising recurring units having an acid labile group as represented by formula (2), optionally an acid generator, basic compound, surfactant or the like in an organic solvent is used in the fabrication of various integrated circuits. Pattern formation using the resist composition may be performed by well-known lithography processes. The process generally involves coating, heat treatment (or prebaking), exposure, heat treatment (PEB), and development. If necessary, any additional steps may be added.

The positive resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, MoSi, or $SiO_2$) by a suitable coating technique such as spin coating, roll coating, flow coating, dip coating, spray coating or doctor coating. The coating is prebaked on a hot plate at a temperature of 60 to 150° C. for 10 seconds to 30 minutes, preferably 80 to 120° C. for 30 seconds to 20 minutes. The resulting resist film is generally 0.1 to 2.0 μm thick.

The resist film is then exposed to a desired pattern of high-energy radiation such as UV, deep-UV, electron beam, x-ray, excimer laser light, γ-ray, synchrotron radiation or extreme UV (soft x-ray), directly or through a mask. The exposure dose is preferably about 1 to 200 $mJ/cm^2$, more preferably about 10 to 100 $mJ/cm^2$, or 0.1 to 100 $\mu C/cm^2$, more preferably 0.5 to 50 $\mu C/cm^2$. The resist film is further baked (PEB) on a hot plate at 60 to 150° C. for 10 seconds to 30 minutes, preferably 80 to 120° C. for 30 seconds to 20 minutes.

Thereafter the resist film is developed with a developer in the form of an aqueous base solution for 3 seconds to 3 minutes, preferably 5 seconds to 2 minutes by conventional techniques such as dip, puddle or spray techniques. Suitable developers are 0.1 to 10 wt %, preferably 2 to 10 wt %, more preferably 2 to 5 wt % aqueous solutions of tetramethylammonium hydroxide (TMAH), tetraethylammonium hydroxide (TEAH), tetrapropylammonium hydroxide (TPAH) and tetrabutylammonium hydroxide (TBAH). The resist film in the exposed area is dissolved in the developer whereas the resist film in the unexposed area is not dissolved. In this way, the desired positive pattern is formed on the substrate. It is appreciated that the resist composition of the invention is best suited for micro-patterning using such high-energy radiation as EB, EUV (soft x-ray), x-ray, γ-ray and synchrotron radiation among others.

Although TMAH aqueous solution is generally used as the developer, TEAH, TPAH and TBAH having a longer alkyl chain are effective in inhibiting the resist film from being swollen during development and thus preventing pattern collapse. JP 3429592 describes an example using an aqueous TBAH solution for the development of a polymer comprising recurring units having an alicyclic structure such as adamantane methacrylate and recurring units having an acid labile group such as t-butyl methacrylate, the polymer being water repellent due to the absence of hydrophilic groups.

The TMAH developer is most often used as 2.38 wt % aqueous solution, which corresponds to 0.26N. The TEAH, TPAH, and TBAH aqueous solutions should preferably have an equivalent normality. The concentration of TEAH, TPAH, and TBAH that corresponds to 0.26N is 3.84 wt %, 5.31 wt %, and 6.78 wt %, respectively.

When a pattern with a line size of 32 nm or less is resolved by the EB and EUV lithography, there arises a phenomenon that lines become wavy, lines merge together, and merged lines collapse. It is believed that this phenomenon occurs because lines are swollen in the developer and the thus expanded lines merge together. Since the swollen lines containing liquid developer are as soft as sponge, they readily collapse under the stress of rinsing. For this reason, the developer using a long-chain alkyl developing agent is effective for preventing film swell and hence, pattern collapse.

EXAMPLE

Synthesis Examples, Comparative Synthesis Examples, Examples and Comparative Examples are given below for further illustrating the invention, but they should not be construed as limiting the invention thereto. Mw is a weight average molecular weight as measured by gel permeation chromatography (GPC) versus polystyrene standards using tetrahydrofuran as a solvent, and Mw/Mn designates molecular weight distribution or dispersity. All parts (pbw) are by weight.

Monomer Synthesis

Polymerizable acid-labile compounds within the scope of the invention were synthesized as follows.

Monomer Synthesis Example 1

Synthesis of Monomer 1

Under ice cooling, isobutene was introduced into a mixture of 17.8 g of 4-hydroxyphenyl methacrylate, 0.3 g of methanesulfonic acid, and 100 g of toluene over 4 hours. To the reaction solution, 50 g of water was added to quench the reaction, from which the organic layer was recovered. The organic layer was washed with water, sodium bicarbonate water, and saturated saline solution in sequence and concentrated. The concentrate was purified by distillation, obtaining 152 g (yield 65%) of 4-tert-butoxyphenyl methacrylate, designated Monomer 1.

Monomer Synthesis Example 2

Synthesis of Monomer 2

The procedure of Monomer Synthesis Example 1 was repeated aside from using 3-hydroxyphenyl methacrylate instead of 4-hydroxyphenyl methacrylate. There was obtained 3-tert-butoxyphenyl methacrylate, designated Monomer 2 (yield 68%).

Monomer Synthesis Example 3

Synthesis of Monomer 3

Monomer Synthesis Example 3-1

Synthesis of 4-tert-amyloxy-1-phenol

A Grignard reagent was previously prepared using 99.3 g of 1-tert-amyloxy-4-chlorobenzene, 12.76 g of magnesium, and 200 mL of tetrahydrofuran. To the Grignard reagent, 57.1 g of trimethyl borate was added dropwise at an internal temperature below −50° C. At a reaction temperature of 5° C., stirring was continued for 3 hours. Thereafter, at an internal temperature below 30° C., 45.0 g of acetic acid and 145.7 g of 35% hydrogen peroxide solution were added. At room temperature, stirring was continued for 3 hours. Standard work-up and purification by silica gel chromatography gave 62.2 g of 4-tert-amyloxy-1-phenol (yield 69%).

Monomer Synthesis Example 3-2

Synthesis of 4-tert-amyloxyphenyl methacrylate

To a mixture of 8.0 g of 4-tert-amyloxy-1-phenol obtained in Monomer Synthesis Example 3-1, 6.3 g of triethylamine, and 20 mL of acetonitrile, 5.6 g of methacrylic acid chloride was added dropwise at an internal temperature below 20° C. Stirring was continued for 2 hours at the temperature, after which 10 mL of water was added to quench the reaction. Standard work-up and vacuum distillation gave 8.4 g of 4-tert-amyloxyphenyl methacrylate, designated Monomer 3 (yield 77%).
Boiling point: 92-93° C./21 Pa
IR (NaCl): v=3106, 2976, 2932, 2881, 1737, 1637, 1500, 1462, 1381, 1366, 1319, 1295, 1194, 1159, 1128, 941, 888 cm$^{-1}$
$^1$H-NMR (600 MHz in DMSO-d$_6$): δ=0.94 (3H, t), 1.19 (6H, s), 1.61 (2H, q), 1.98 (3H, m), 5.85-5.87 (1H, m), 6.24 (1H, s), 6.95-6.98 (2H, m), 7.03-7.07 (2H, m) ppm
$^{13}$C-NMR (150 MHz in DMSO-d$_6$): δ=8.43, 18.00, 25.73, 33.76, 80.35, 122.06, 124.17, 127.47, 135.32, 145.87, 152.55, 165.31 ppm Monomer Synthesis Example 4

Synthesis of Monomer 4

Under ice cooling, a mixture of 159.2 g of di-tent-butyl dicarbonate and 100 mL of tetrahydrofuran was added dropwise to a mixture of 100.0 g of 4-hydroxyphenyl methacrylate, 85.2 g of triethylamine, and 500 mL of tetrahydrofuran over 2 hours. Stirring was continued for 8 hours at room temperature, after which 250 g of water was added to quench the reaction. Standard work-up and purification by silica gel chromatography gave 137.4 g of 4-tert-butoxycarboxyoxyphenyl methacrylate, designated Monomer 4 (yield 88%).

Monomer Synthesis Example 5

Synthesis of Monomer 5

The procedure of Monomer Synthesis Example 4 was repeated aside from using cyclohexyl chloromethyl ether instead of di-tert-butyl dicarbonate. There was obtained 4-cyclohexyloxymethoxyphenyl methacrylate, designated Monomer 5 (yield 89%).

Monomer Synthesis Example 6

Synthesis of Monomer 6

The procedure of Monomer Synthesis Example 1 was repeated aside from using methylene cyclopentane instead of isobutene. There was obtained 4-methylcyclopentyloxyphenyl methacrylate, designated Monomer 6 (yield 61%).

Monomer Synthesis Example 7

Synthesis of Monomer 7

The procedure of Monomer Synthesis Example 1 was repeated aside from using 2-methyleneadamantane instead of isobutene. There was obtained 4-(2-methyladamantyloxy)phenyl methacrylate, designated Monomer 7 (yield 61%).

Monomer Synthesis Example 8

Synthesis of Monomer 8

The procedure of Monomer Synthesis Example 4 was repeated aside from using 1-chloro-2-methylpropyl methyl ether instead of cyclohexyl chloromethyl ether. There was obtained 4-(methoxy-2-methylpropoxy)phenyl methacrylate, designated Monomer 8 (yield 87%).

Monomer Synthesis Example 9

Synthesis of Monomer 9

The procedure of Monomer Synthesis Example 1 was repeated aside from using methylenecyclohexane instead of isobutene. There was obtained 4-methylcyclohexyloxyphenyl methacrylate, designated Monomer 9 (yield 60%).

Monomer Synthesis Example 10

Synthesis of Monomer 10

The procedure of Monomer Synthesis Example 4 was repeated aside from using neopentyl chloromethyl ether instead of di-tert-butyl dicarbonate. There was obtained 4-neopentyloxymethoxyphenyl methacrylate, designated Monomer 10 (yield 92%).

Monomer Synthesis Example 11

Synthesis of Monomer 11

The procedure of Monomer Synthesis Example 4 was repeated aside from using 2-adamantyl chloromethyl ether instead of di-tert-butyl dicarbonate. There was obtained 4-(2-adamantylmethoxy)phenyl methacrylate, designated Monomer 11 (yield 72%).

Monomer Synthesis Example 12

Synthesis of Monomer 12

The procedure of Monomer Synthesis Example 4 was repeated aside from using 1-adamantylmethyl chloromethyl ether instead of di-tert-butyl dicarbonate. There was obtained 4-(1-adamantylmethylmethoxy)phenyl methacrylate, designated Monomer 12 (yield 74%).

Monomer Synthesis Example 13

Synthesis of Monomer 13

The procedure of Monomer Synthesis Example 1 was repeated aside from using isopropylenecyclopentane instead of isobutene. There was obtained 4-isopropylcyclopentyloxy-phenyl methacrylate, designated Monomer 13 (yield 30%).

Monomer Synthesis Example 14

Synthesis of Monomer 14

The procedure of Monomer Synthesis Example 1 was repeated aside from using ethylenecyclohexane instead of isobutene. There was obtained 4-ethylcyclohexyloxyphenyl methacrylate, designated Monomer 14 (yield 32%).

Monomers 1 to 14 have the structures shown below.

Monomer 1

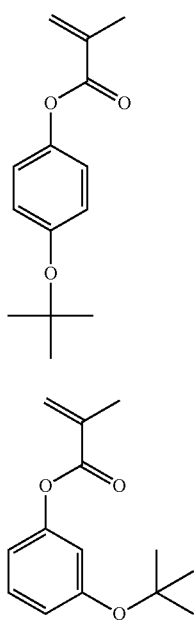

Monomer 2

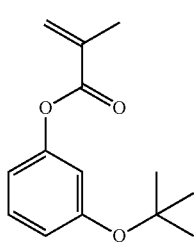

Monomer 3

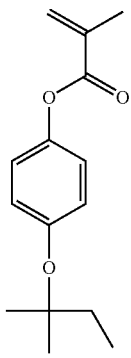

Monomer 4

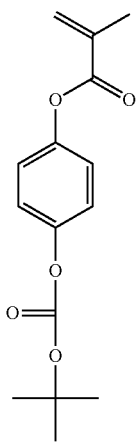

Monomer 5

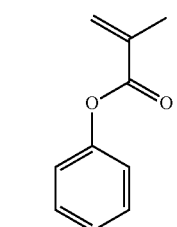

Monomer 6

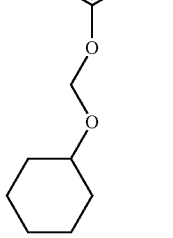

Momomer 7
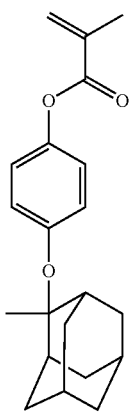
Monomer 8
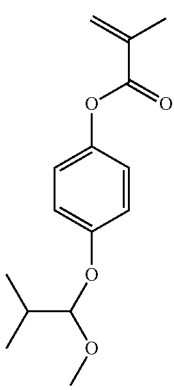
Monomer 9
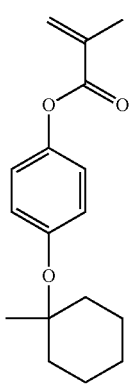
Monomer 10
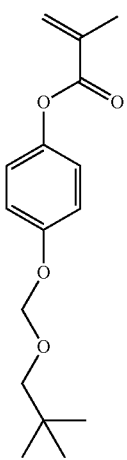
Monomer 11
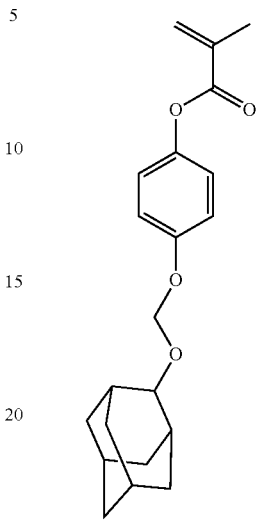
Monomer 12
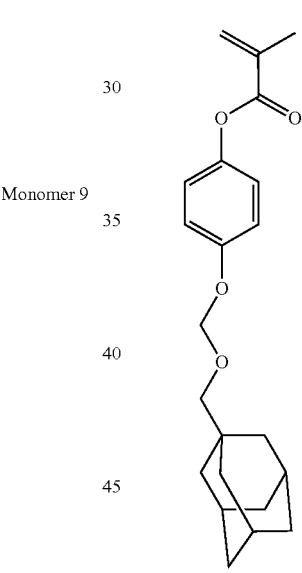
Monomer 13
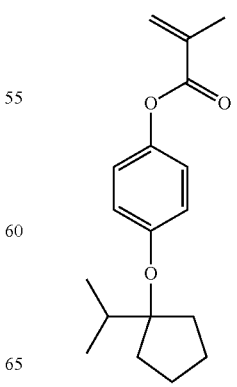

Monomer 14

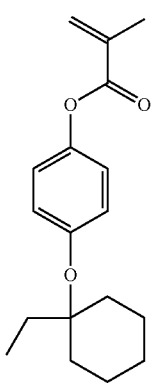

Monomer 1: 4-tert-butoxyphenyl methacrylate
Monomer 2: 3-tert-butoxyphenyl methacrylate
Monomer 3: 4-tert-amyloxyphenyl methacrylate
Monomer 4: 4-tert-butoxycarbonyloxyphenyl methacrylate
Monomer 5: 4-cyclohexyloxymethoxyphenyl methacrylate
Monomer 6: 4-methylcyclopentyloxyphenyl methacrylate
Monomer 7: 4-(2-methyladamantyloxy)phenyl methacrylate
Monomer 8: 4-(methoxy-2-methylpropoxy)phenyl methacrylate
Monomer 9: 4-methylcyclohexyloxyphenyl methacrylate
Monomer 10: 4-neopentyloxymethoxyphenyl methacrylate
Monomer 11: 4-(2-adamantylmethoxy)phenyl methacrylate
Monomer 12: 4-(1-adamantylmethylmethoxy)phenyl methacrylate
Monomer 13: 4-isopropylcyclopentyloxyphenyl methacrylate
Monomer 14: 4-ethylcyclohexyloxyphenyl methacrylate PAG monomers 1 to 3 and Adhesive monomers 1 and 2 used herein are shown below.

PAG monomer 1

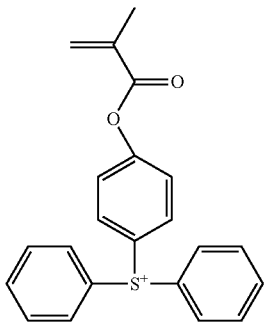

PAG monomer 2

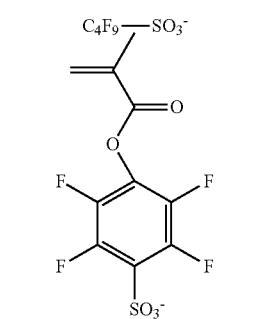

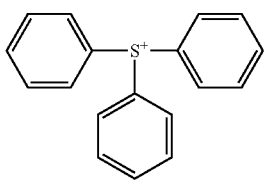

PAF monomer 3

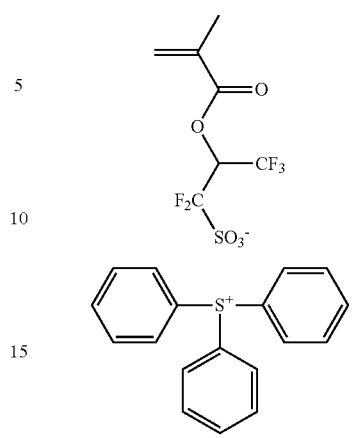

PAG monomer 1: 4-methacrylic acid-oxyphenyldiphenylsulfonium perfluorobutanesulfonate
PAG monomer 2: triphenylsulfonium 2,3,5,6-tetrafluoro-4-methacryloyloxybenzenesulfonate
PAG monomer 3: triphenylsulfonium 1,1,3,3,3-pentafluoro-2-methacryloyloxypropane-1-sulfonate Adhesive monomer 1

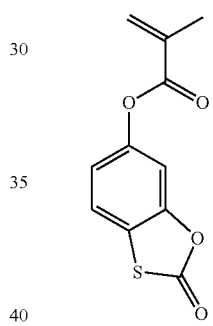

Adhesive monomer 2

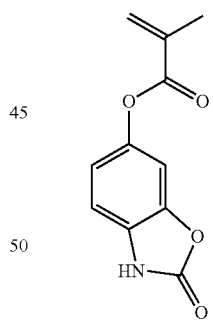

Adhesive monomer 1: 2-oxo-1,3-benzoxathiol-5-yl methacrylate
Adhesive monomer 2: 2-oxo-2,3-dihydrobenzoxazol-5-yl methacrylate Polymer Synthesis Synthesis Example 1

A 2-L flask was charged with 8.2 g of Monomer 1, 10.5 g of 4-acetoxystyrene, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of azobisisobutyronitrile (AIBN) was added as a polymerization initiator. The reactor was heated at 60° C. and reaction run for 15 hours. The reaction solution was precipitated from 1 L of isopropyl alcohol. The white solid was collected by filtration and dissolved again in a mixture of 100 mL of methanol and 200 mL of tetrahydrofuran, to which 10 g of triethylamine and 10 g of water were added. Deprotection reaction of acetyl group was conducted at 70° C. for 5 hours, followed by neutralization with acetic acid. The reaction solution was concentrated and dissolved in 100 mL of acetone. By similar precipitation, filtration, and drying at 60° C., a white polymer was obtained.

The polymer was analyzed by $^{13}$C-NMR, $^1$H-NMR, and GPC, with the analytical data shown below.
Copolymer Composition (Molar Ratio)
  Monomer 1:4-hydroxystyrene=0.35:0.65
Mw=8,100
Mw/Mn=1.63
This is designated Polymer 1.

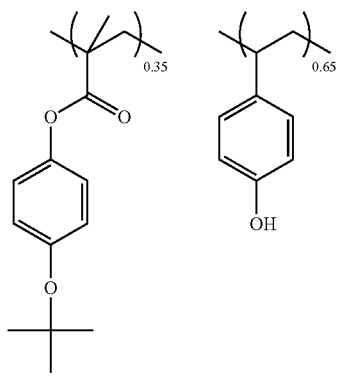

Polymer 1

Synthesis Example 2

A 2-L flask was charged with 7.0 g of Monomer 2, 12.5 g of 3-hydroxyphenyl methacrylate, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^1$H-NMR, and GPC, with the analytical data shown below.
Copolymer Composition (Molar Ratio)
  Monomer 2:3-hydroxyphenyl methacrylate=0.29:0.71
Mw=8,200
Mw/Mn=1.71
This is designated Polymer 2.

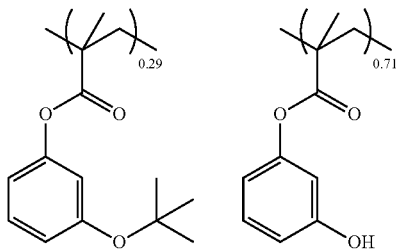

Polymer 2

Synthesis Example 3

A 2-L flask was charged with 7.0 g of Monomer 4, 16.3 g of 5-hydroxyindan-2-yl methacrylate, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^1$H-NMR, and GPC, with the analytical data shown below.
Copolymer Composition (Molar Ratio)
  Monomer 4:5-hydroxyindan-2-yl methacrylate=0.25:0.75
Mw=8,900
Mw/Mn=1.96
This is designated Polymer 3.

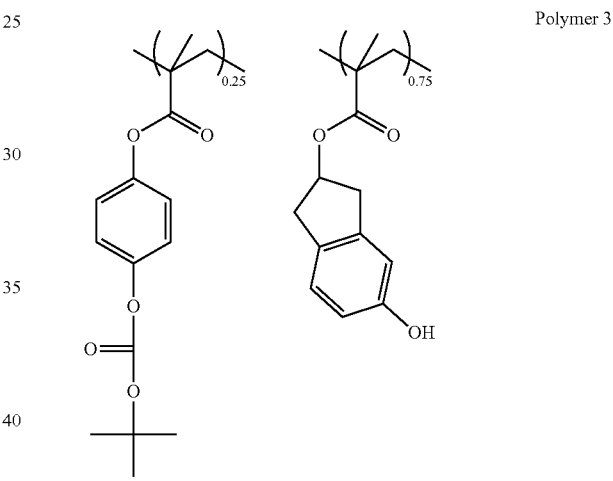

Polymer 3

Synthesis Example 4

A 2-L flask was charged with 7.4 g of Monomer 3, 8.7 g of 5-hydroxyindan-2-yl methacrylate, 6.7 g of 3-oxo-2,7-dioxatricyclo[4.2.1.0$^{4,8}$]nonan-9-yl methacrylate, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^1$H-NMR, and GPC, with the analytical data shown below.
Copolymer Composition (Molar Ratio)
  Monomer 3:5-hydroxyindan-2-yl methacrylate: 3-oxo-2,7-dioxatricyclo[4.2.1.0$^{4,8}$]nonan-9-yl methacrylate=0.30:0.40:0.30

Mw=8,200
Mw/Mn=1.81
This is designated Polymer 4.

Polymer 4

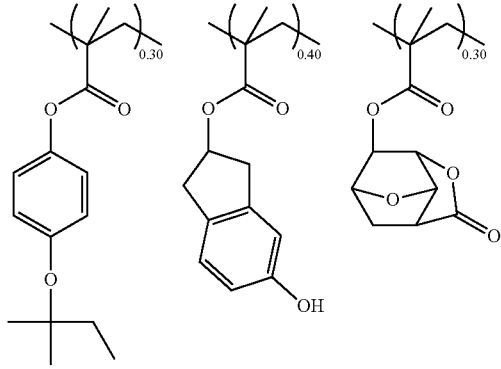

Synthesis Example 5

A 2-L flask was charged with 6.7 g of Monomer 5, 1.7 g of indene, 10.8 g of 4-acetoxystyrene, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and dissolved again in a mixture of 100 mL of methanol and 200 mL of tetrahydrofuran, to which 10 g of triethylamine and 10 g of water were added. Deprotection reaction of acetyl group was conducted at 70° C. for 5 hours, followed by neutralization with acetic acid. The reaction solution was concentrated and dissolved in 100 mL of acetone. By similar precipitation, filtration, and drying at 60° C., a white polymer was obtained.

The polymer was analyzed by $^{13}$C-NMR, $^{1}$H-NMR, and GPC, with the analytical data shown below.
Copolymer Composition (Molar Ratio)
　Monomer 5:indene:4-hydroxystyrene=0.23:0.10:0.67
Mw=6,900
Mw/Mn=1.69
This is designated Polymer 5.

Polymer 5

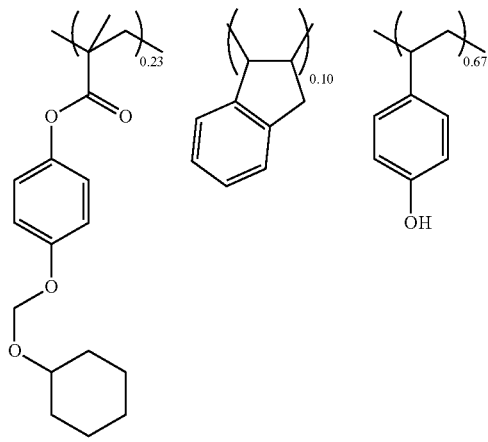

Synthesis Example 6

A 2-L flask was charged with 15.1 g of 4-hydroxyphenyl methacrylate, 1.6 g of styrene, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isobutyl alcohol. The white solid was collected by filtration and dissolved again in 200 mL of tetrahydrofuran, to which 3.5 g of 1-chloro-1-methoxy-2-methylpropane was added. With stirring at room temperature, 11 g of triethylamine was added to the solution, which was stirred for 16 hours. The reaction solution was poured into 1 L of acetic acid water for crystallization. The resulting white solid was washed twice with water, collected by filtration, and vacuum dried at 40° C., obtaining a white polymer.

The polymer was analyzed by $^{13}$C-NMR, $^{1}$H-NMR, and GPC, with the analytical data shown below.
Copolymer Composition (Molar Ratio)
　4-(methoxy-2-methylpropoxy)phenyl methacrylate: 4-hydroxyphenyl methacrylate:styrene=0.30:0.55:0.15
Mw=8,600
Mw/Mn=1.98
This is designated Polymer 6.

Polymer 6

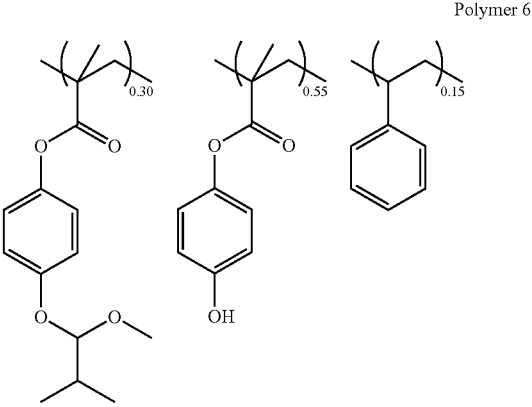

Synthesis Example 7

A 2-L flask was charged with 8.2 g of Monomer 1, 4.8 g of 1-hydroxynaphthalen-5-yl methacrylate, 7.5 g of tetrahydro-2-oxofuran-3-yl methacrylate, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^{1}$H-NMR, and GPC, with the analytical data shown below.
Copolymer Composition (Molar Ratio)
　Monomer 1:1-hydroxynaphthalen-5-yl methacrylate: tetrahydro-2-oxofuran-3-yl methacrylate=0.35:0.21:0.44

Mw=7,300
Mw/Mn=1.87
This is designated Polymer 7.

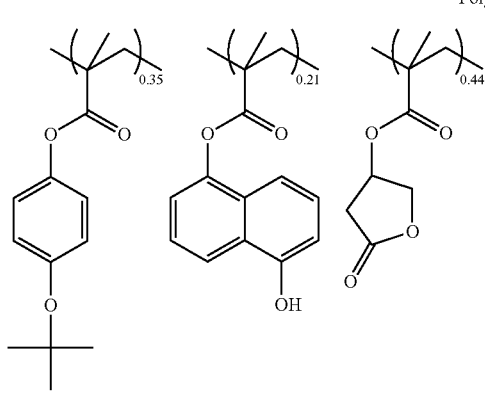

Polymer 7

Synthesis Example 8

A 2-L flask was charged with 7.5 g of Monomer 1, 9.4 g of 4-acetoxystyrene, 1.7 g of acenaphthylene, and 20 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and dissolved again in a mixture of 100 mL of methanol and 200 mL of tetrahydrofuran, to which 10 g of triethylamine and 10 g of water were added. Deprotection reaction of acetyl group was conducted at 70° C. for 5 hours, followed by neutralization with acetic acid. The reaction solution was concentrated and dissolved in 100 mL of acetone. By similar precipitation, filtration, and drying at 60° C., a white polymer was obtained.

The polymer was analyzed by $^{13}$C-NMR, $^{1}$H-NMR, and GPC, with the analytical data shown below.
Copolymer Composition (Molar Ratio)
    Monomer 1:4-hydroxystyrene:acenaphthylene=0.32: 0.58:0.10
Mw=5,500
Mw/Mn=1.71
This is designated Polymer 8.

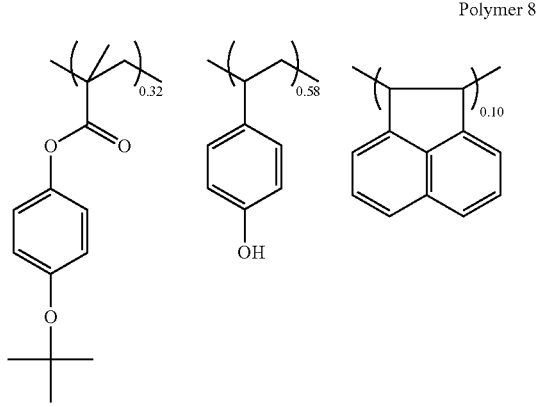

Polymer 8

Synthesis Example 9

A 2-L flask was charged with 8.0 g of Monomer 1, 2.0 g of 7-acetoxyindene, 8.8 g of 4-acetoxystyrene, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and dissolved again in a mixture of 100 mL of methanol and 200 mL of tetrahydrofuran, to which 10 g of triethylamine and 10 g of water were added. Deprotection reaction of acetyl group was conducted at 70° C. for 5 hours, followed by neutralization with acetic acid. The reaction solution was concentrated and dissolved in 100 mL of acetone. By similar precipitation, filtration, and drying at 60° C., a white polymer was obtained.

The polymer was analyzed by $^{13}$C-NMR, $^{1}$H-NMR, and GPC, with the analytical data shown below.
Copolymer Composition (Molar Ratio)
    Monomer 1:7-hydroxyindene:4-hydroxystyrene=0.34: 0.10:0.56
Mw=6,300
Mw/Mn=1.63
This is designated Polymer 9.

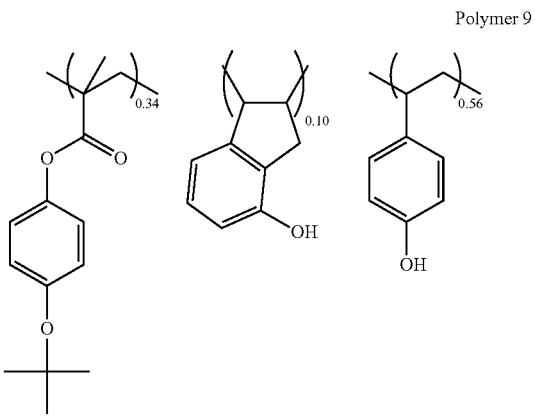

Polymer 9

Synthesis Example 10

A 2-L flask was charged with 8.2 g of Monomer 1, 6.5 g of 4-acetoxystyrene, 2.7 g of 6-hydroxycoumarin, 1.5 g of coumarin, and 20 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and dissolved again in a mixture of 100 mL of methanol and 200 mL of tetrahydrofuran, to which 10 g of triethylamine and 10 g of water were added. Deprotection reaction of acetyl group was conducted at 70° C. for 5 hours, followed by neutralization with acetic acid. The reaction solution was concentrated and dissolved in 100 mL of acetone. By similar precipitation, filtration, and drying at 60° C., a white polymer was obtained.

The polymer was analyzed by $^{13}$C-NMR, $^{1}$H-NMR, and GPC, with the analytical data shown below.
Copolymer Composition (Molar Ratio)
    Monomer 1:4-hydroxystyrene:6-hydroxycoumarin: coumarin=0.35:0.40:0.15:0.10

Mw=6,100
Mw/Mn=1.71
This is designated Polymer 10.

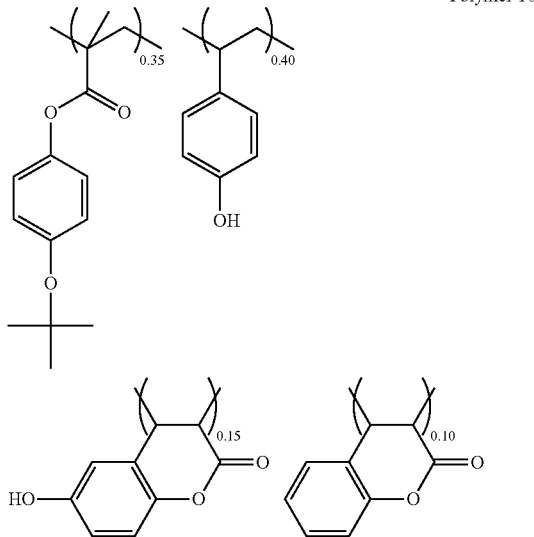
Polymer 10

Synthesis Example 11

A 2-L flask was charged with 7.4 g of Monomer 3, 14.1 g of 7-hydroxy-1,2,3,4-tetrahydronaphthalen-2-yl methacrylate, and 20 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^1$H-NMR, and GPC, with the analytical data shown below.
Copolymer Composition (Molar Ratio)
   Monomer 3:7-hydroxy-1,2,3,4-tetrahydronaphthalen-2-yl methacrylate=0.30:0.70
Mw=6,900
Mw/Mn=1.79
This is designated Polymer 11.

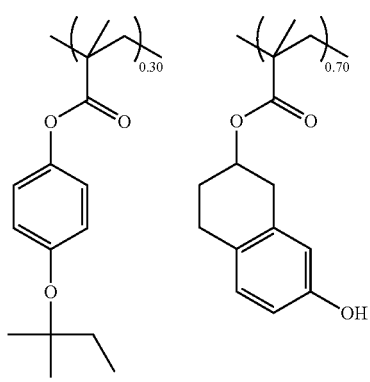
Polymer 11

Synthesis Example 12

A 2-L flask was charged with 16.0 g of 4-hydroxyphenyl methacrylate, 1.5 g of 2-vinylnaphthalene, and 20 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isobutyl alcohol. The white solid was collected by filtration and dissolved again in 200 mL of tetrahydrofuran, to which 0.01 g of methanesulfonic acid and 3.5 g of 2-indanyl vinyl ether were added. Reaction was run at room temperature for 1 hour, after which 0.25 g of 30% ammonia water was added to quench the reaction. The reaction solution was poured into 1 L of acetic acid solution for crystallization. The resulting white solid was washed twice with water, collected by filtration, and vacuum dried at 40° C., obtaining a white polymer.

The polymer was analyzed by $^{13}$C-NMR, $^1$H-NMR, and GPC, with the analytical data shown below.
Copolymer Composition (Molar Ratio)
   4-(2-indanyloxyethoxy)phenyl methacrylate: 4-hydroxyphenyl methacrylate:2-vinylnaphthalene=0.26:0.64:0.10
Mw=7,600
Mw/Mn=1.72
This is designated Polymer 12.

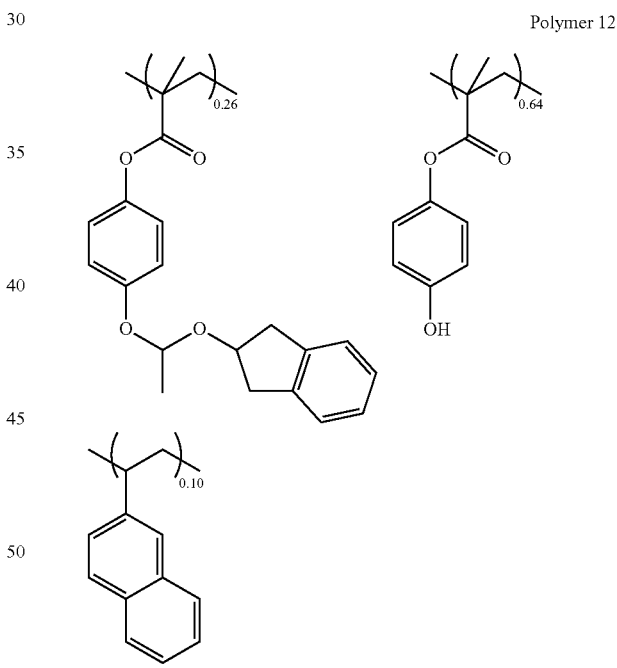
Polymer 12

Synthesis Example 13

A 2-L flask was charged with 16.0 g of 4-hydroxyphenyl methacrylate, 2.0 g of methyl 2,5-norbornadiene-2-carboxylate, and 20 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isobutyl alcohol. The white solid was collected by filtration and dissolved again in 200 mL of tetrahydrofuran, to which 0.01 g of methanesulfonic acid and 3.5 g of 1-acenaphthenyl vinyl ether were added. Reaction was run at room temperature for 1 hour, after which 0.25 g of 30% ammonia water was added to quench the reaction. The reaction solution was poured into 1 L of acetic acid solution for crystallization. The resulting white solid was washed twice with water, collected by filtration, and vacuum dried at 40° C., obtaining a white polymer.

The polymer was analyzed by $^{13}$C-NMR, $^1$H-NMR, and GPC, with the analytical data shown below.
Copolymer Composition (Molar Ratio)
4-(1-acenaphthenyloxyethoxy)phenyl methacrylate: 4-hydroxyphenyl methacrylate: methyl 2,5-norbornadiene-2-carboxylate=0.25:0.65:0.10
Mw=6,100
Mw/Mn=1.88
This is designated Polymer 13.

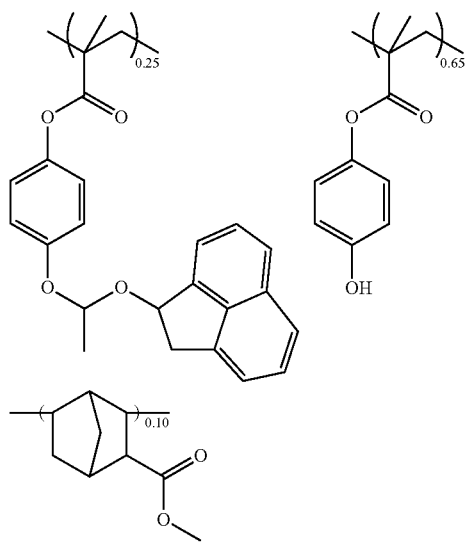

Polymer 13

Synthesis Example 14

A 2-L flask was charged with 17.8 g of 4-hydroxyphenyl methacrylate and 20 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isobutyl alcohol. The white solid was collected by filtration and dissolved again in 200 mL of tetrahydrofuran, to which 0.01 g of methanesulfonic acid and 3.4 g of 9-fluorenyl vinyl ether were added. Reaction was run at room temperature for 1 hour, after which 0.25 g of 30% ammonia water was added to quench the reaction. The reaction solution was poured into 1 L of acetic acid solution for crystallization. The resulting white solid was washed with water twice, collected by filtration, and vacuum dried at 40° C., obtaining a white polymer.

The polymer was analyzed by $^{13}$C-NMR, $^1$H-NMR, and GPC, with the analytical data shown below.
Copolymer Composition (Molar Ratio)
4-(9-fluorenyloxyethoxy)phenyl methacrylate: 4-hydroxyphenyl methacrylate=0.32:0.68
Mw=7,100
Mw/Mn=1.76
This is designated Polymer 14.

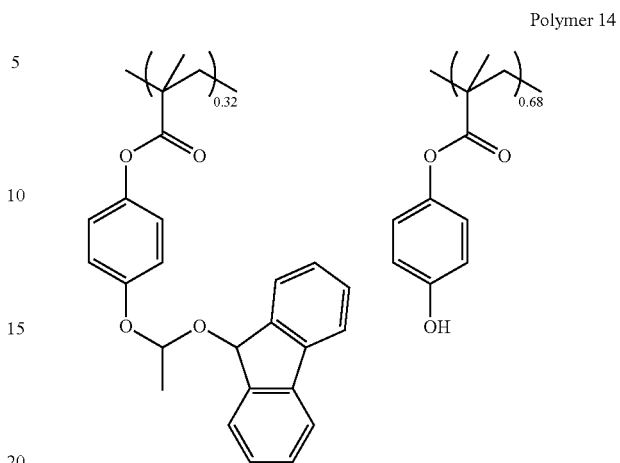

Polymer 14

Synthesis Example 15

A 2-L flask was charged with 16.0 g of 4-hydroxyphenyl methacrylate, 1.6 g of acenaphthylene, and 20 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isobutyl alcohol. The white solid was collected by filtration and dissolved again in 200 mL of tetrahydrofuran, to which 4.1 g of 1-chloro-2-methyl-tricyclo[5.2.1.0$^{2,6}$]dec-8-yloxypropane was added. With stirring at room temperature, 11 g of triethylamine was added to the solution, and stirring was continued for a further 16 hours. The reaction solution was poured into 1 L of acetic acid solution for crystallization. The resulting white solid was washed twice with water, collected by filtration, and vacuum dried at 40° C., obtaining a white polymer.

The polymer was analyzed by $^{13}$C-NMR, $^1$H-NMR, and GPC, with the analytical data shown below.
Copolymer Composition (Molar Ratio)
4-(tricyclo[5.2.1.0$^{2,6}$]dec-8-yloxy-2-methylpropoxy)-phenyl methacrylate:4-hydroxyphenyl methacrylate: acenaphthylene=0.28:0.62:0.10
Mw=7,100
Mw/Mn=1.76
This is designated Polymer 15.

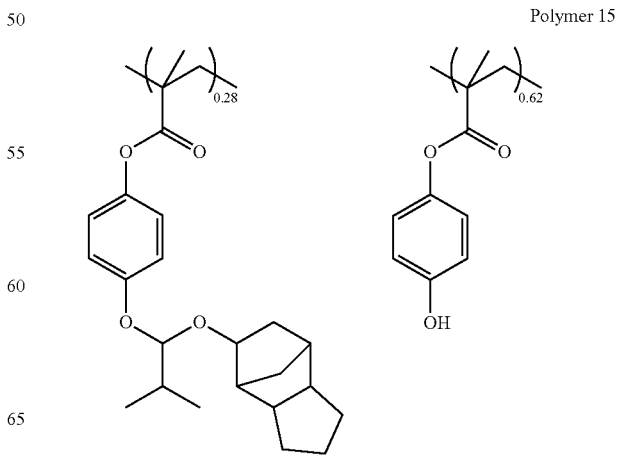

Polymer 15

-continued

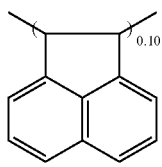

Synthesis Example 16

A 2-L flask was charged with 7.0 g of Monomer 1, 5.3 g of 4-hydroxyphenyl methacrylate, 6.7 g of 3-oxo-2,7-dioxatricyclo[4.2.1.0$^{4,8}$]nonan-9-yl methacrylate, 6.5 g of PAG monomer 1, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^1$H-NMR, and GPC, with the analytical data shown below.
Copolymer Composition (Molar Ratio)
  Monomer 1:4-hydroxyphenyl methacrylate: 3-oxo-2,7-dioxatricyclo[4.2.1.0$^{4,8}$]nonan-9-yl methacrylate:PAG monomer 1=0.30:0.30:0.30:0.10
Mw=8,100
Mw/Mn=1.91
This is designated Polymer 16.

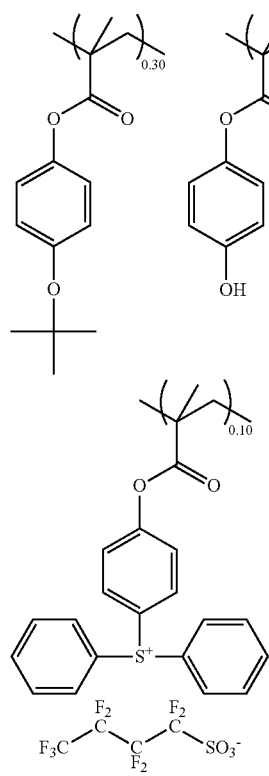

Polymer 16

Synthesis Example 17

A 2-L flask was charged with 7.0 g of Monomer 1, 5.3 g of 4-hydroxyphenyl methacrylate, 6.7 g of 3-oxo-2,7-dioxatricyclo[4.2.1.0$^{4,8}$]nonan-9-yl methacrylate, 5.7 g of PAG monomer 2, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^1$H-NMR, and GPC, with the analytical data shown below.
Copolymer Composition (Molar Ratio)
  Monomer 1:4-hydroxyphenyl methacrylate: 3-oxo-2,7-dioxatricyclo[4.2.1.0$^{4,8}$]nonan-9-yl methacrylate:PAG monomer 2=0.30:0.30:0.30:0.10
Mw=8,300
Mw/Mn=1.93
This is designated Polymer 17.

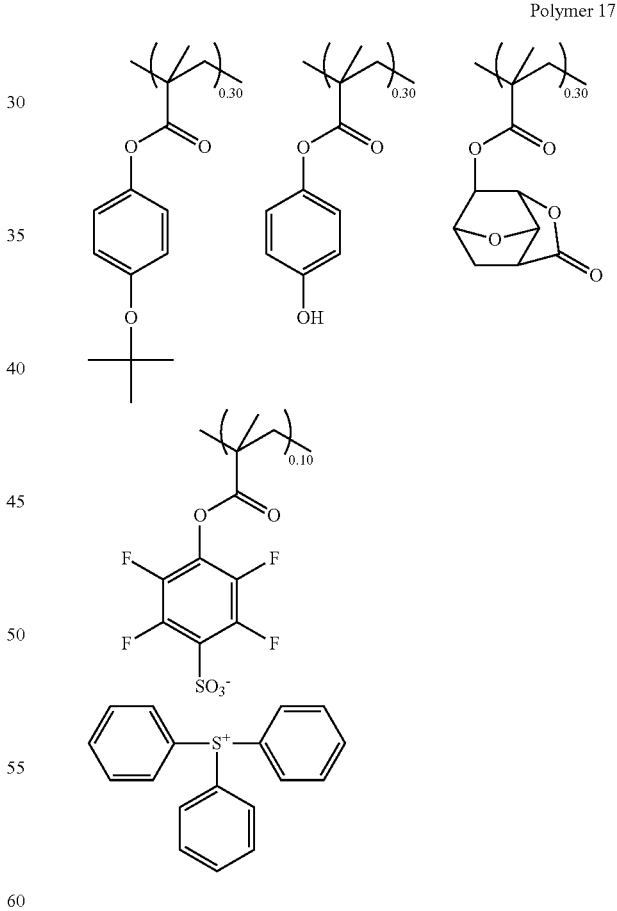

Polymer 17

Synthesis Example 18

A 2-L flask was charged with 7.0 g of Monomer 1, 5.3 g of 4-hydroxyphenyl methacrylate, 6.7 g of 3-oxo-2,7-dioxatricyclo[4.2.1.0$^{4,8}$]nonan-9-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^{1}$H-NMR, and GPC, with the analytical data shown below.

Copolymer Composition (Molar Ratio)
  Monomer 1:4-hydroxyphenyl methacrylate: 3-oxo-2,7-dioxatricyclo[4.2.1.0$^{4,8}$]nonan-9-yl methacrylate:PAG monomer 3=0.30:0.30:0.30:0.10

Mw=7,900
Mw/Mn=1.93

This is designated Polymer 18.

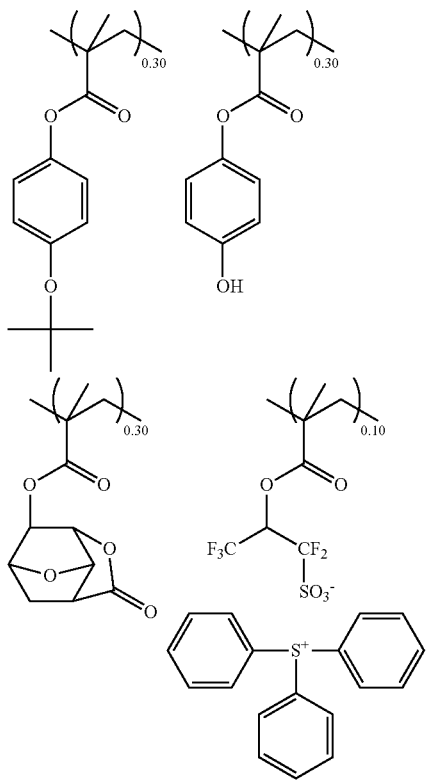

Polymer 18

Synthesis Example 19

A 2-L flask was charged with 3.5 g of Monomer 1, 4.1 g of 3-ethyl-3-exo-tetracyclo[4.4.0.1$^{2,5}$.1$^{7,10}$]dodecanyl methacrylate, 5.3 g of 4-hydroxyphenyl methacrylate, 6.5 g of 2,7-dihydro-2-oxobenzo[C]furan-5-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^{1}$H-NMR, and GPC, with the analytical data shown below.

Copolymer Composition (Molar Ratio)
  Monomer 1:3-ethyl-3-exo-tetracyclo[4.4.0.1$^{2,5}$.1$^{7,10}$]-dodecanyl methacrylate:4-hydroxyphenyl methacrylate: 2,7-dihydro-2-oxobenzo[C]furan-5-yl methacrylate: PAG monomer 3=0.15:0.15:0.30:0.30:0.10

Mw=7,800
Mw/Mn=1.70

This is designated Polymer 19.

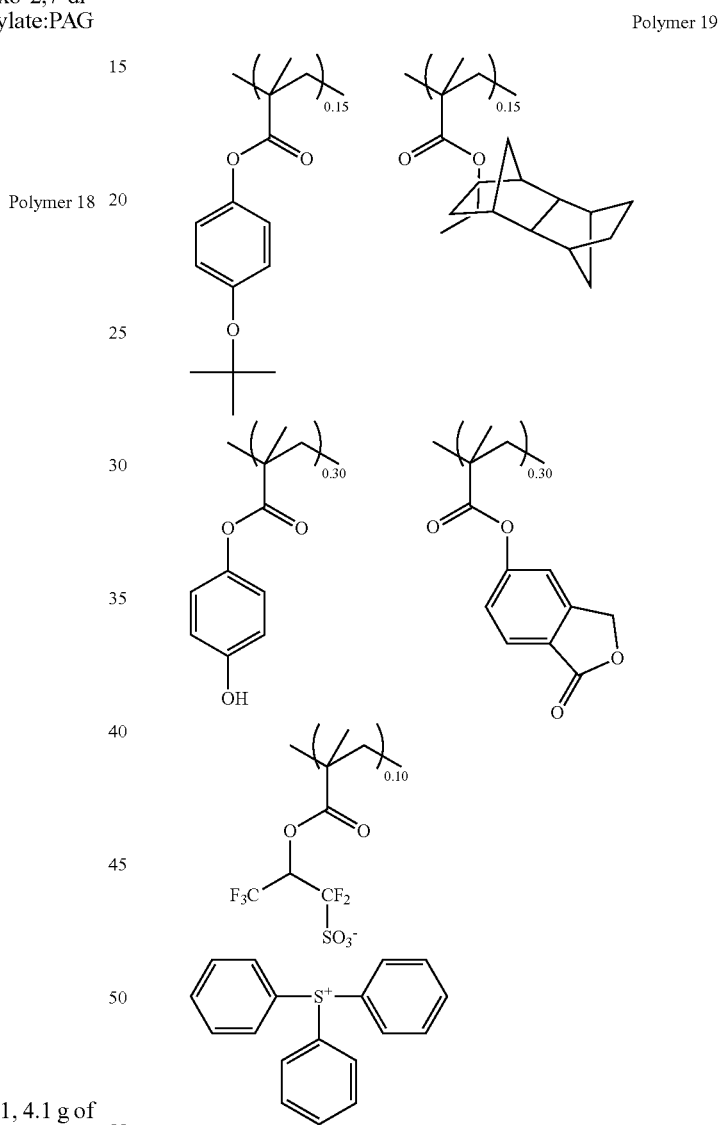

Polymer 19

Synthesis Example 20

A 2-L flask was charged with 7.0 g of Monomer 1, 6.4 g of 6-acetoxy-2-vinylnaphthalene, 6.7 g of 3-oxo-2,7-dioxatricyclo[4.2.1.0$^{4,8}$]nonan-9-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and dissolved again in a mixture of 100 mL of methanol and 200 mL of tetrahydrofuran, to which 10 g of triethylamine and 10 g of water were added. Deprotection reaction of acetyl group was conducted at 70° C. for 5 hours, followed by neutralization with acetic acid. The reaction solution was concentrated and dissolved in 100 mL of acetone. By similar precipitation, filtration, and drying at 60° C., a white polymer was obtained.

The polymer was analyzed by $^{13}$C-NMR, $^{1}$H-NMR, and GPC, with the analytical data shown below.

Copolymer Composition (Molar Ratio)
  Monomer 1:6-hydroxy-2-vinylnaphthalene: 3-oxo-2,7-dioxatricyclo[4.2.1.0$^{4,8}$]nonan-9-yl methacrylate:PAG monomer 3=0.30:0.30:0.30:0.10

Mw=6,800
Mw/Mn=1.99

This is designated Polymer 20.

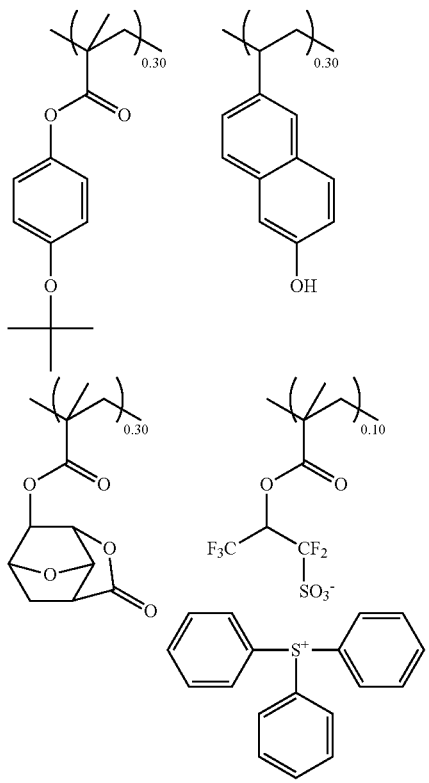

Polymer 20

Synthesis Example 21

A 2-L flask was charged with 7.0 g of Monomer 1, 6.5 g of 5-hydroxyindan-2-yl methacrylate, 6.7 g of 3-oxo-2,7-dioxatricyclo[4.2.1.0$^{4,8}$]nonan-9-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^{1}$H-NMR, and GPC, with the analytical data shown below.

Copolymer Composition (Molar Ratio)
  Monomer 1:5-hydroxyindan-2-yl methacrylate: 3-oxo-2,7-dioxatricyclo[4.2.1.0$^{4,8}$]nonan-9-yl methacrylate: PAG monomer 3=0.30:0.30:0.30:0.10

Mw=8,100
Mw/Mn=1.96

This is designated Polymer 21.

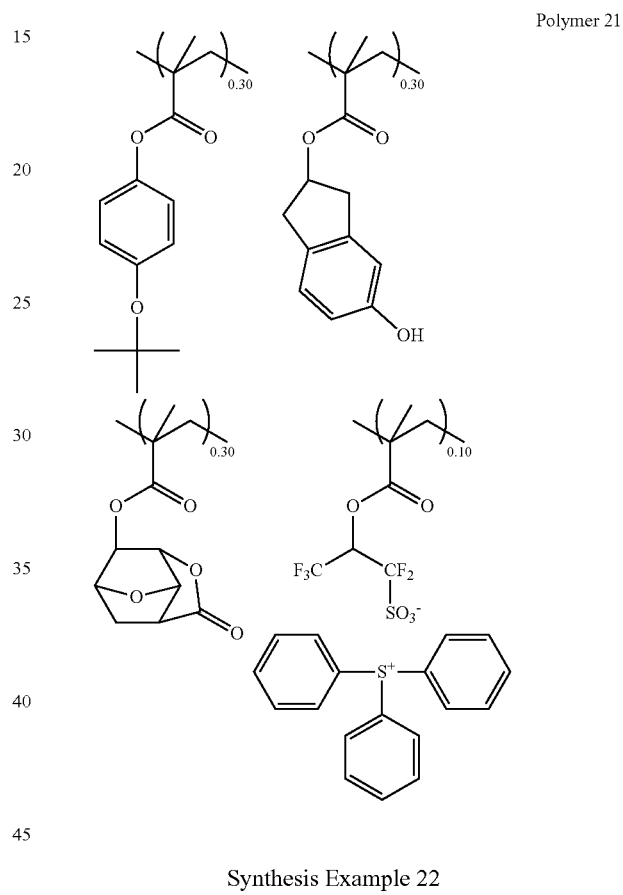

Polymer 21

Synthesis Example 22

A 2-L flask was charged with 7.8 g of Monomer 6, 7.4 g of 5,8-dihydroxy-1,2,3,4-tetrahydronaphthalen-2-yl methacrylate, 6.7 g of 3-oxo-2,7-dioxatricyclo[4.2.1.0$^{4,8}$]-nonan-9-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^{1}$H-NMR, and GPC, with the analytical data shown below.

Copolymer Composition (Molar Ratio)
  Monomer 6:5,8-dihydroxy-1,2,3,4-tetrahydronaphthalen-2-yl methacrylate:3-oxo-2,7-dioxatricyclo[4.2.1.0$^{4,8}$]-nonan-9-yl methacrylate:PAG monomer 3=0.30:0.20:0.40:0.10

Mw=8,900
Mw/Mn=1.66

This is designated Polymer 22.

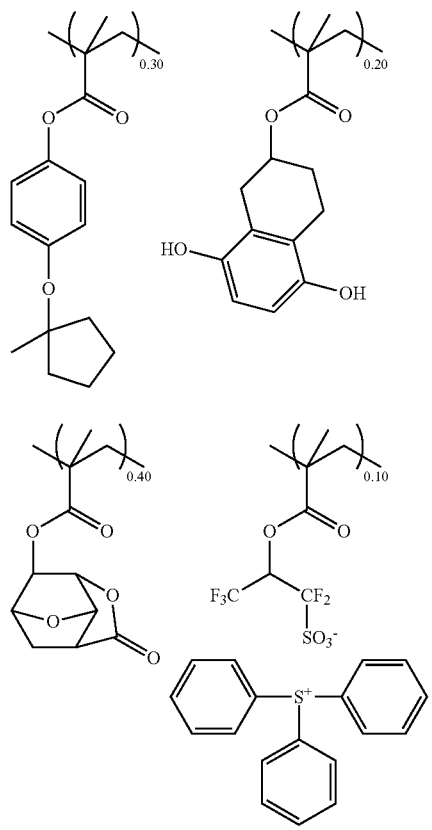

Polymer 22

Mw=8,300
Mw/Mn=1.89

This is designated Polymer 23.

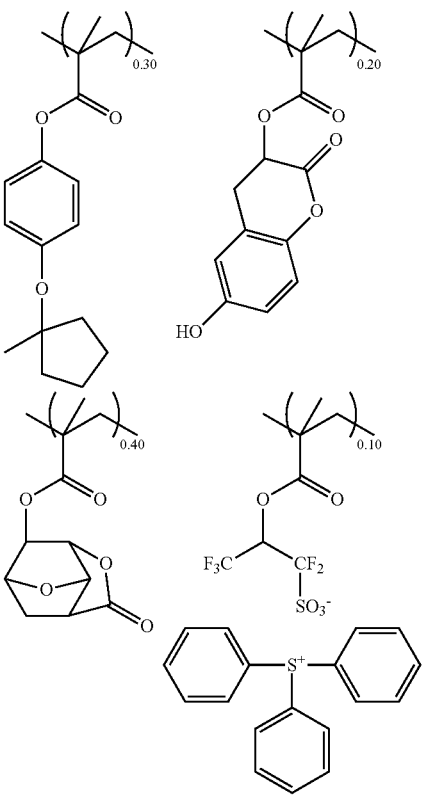

Polymer 23

Synthesis Example 23

A 2-L flask was charged with 7.8 g of Monomer 6, 7.4 g of 6-hydroxycoumarin-3-yl methacrylate, 6.7 g of 3-oxo-2,7-dioxatricyclo[4.2.1.0$^{4,8}$]nonan-9-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^1$H-NMR, and GPC, with the analytical data shown below.

Copolymer Composition (Molar Ratio)

Monomer 6:6-hydroxycoumarin-3-yl methacrylate: 3-oxo-2,7-dioxatricyclo[4.2.1.0$^{4,8}$]nonan-9-yl methacrylate:PAG monomer 3=0.30:0.20:0.40:0.10

Synthesis Example 24

A 2-L flask was charged with 7.0 g of Monomer 1, 4.5 g of 4-hydroxy-1-naphthalene methacrylate, 6.7 g of 3-oxo-2,7-dioxatricyclo[4.2.1.0$^{4,8}$]nonan-9-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^1$H-NMR, and GPC, with the analytical data shown below.

Copolymer Composition (Molar Ratio)

Monomer 1:4-hydroxy-1-naphthalene methacrylate: 3-oxo-2,7-dioxatricyclo[4.2.1.0$^{4,8}$]nonan-9-yl methacrylate:PAG monomer 3=0.30:0.20:0.40:0.10

Mw=7,300
Mw/Mn=1.77

This is designated Polymer 24.

This is designated Polymer 25.

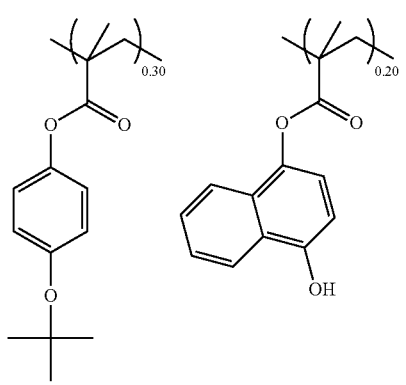

Polymer 24

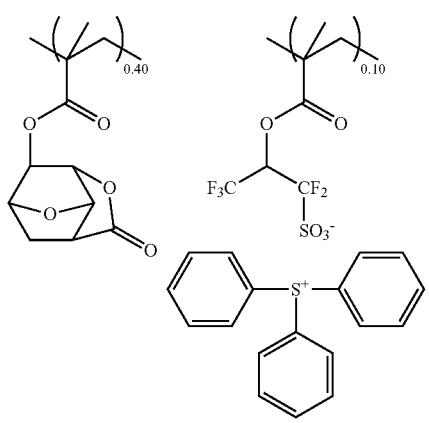

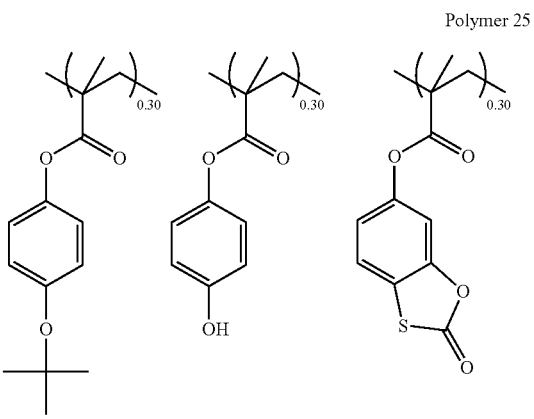

Polymer 25

Synthesis Example 25

A 2-L flask was charged with 7.0 g of Monomer 1, 5.3 g of 4-hydroxyphenyl methacrylate, 6.7 g of Adhesive monomer 1, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^1$H-NMR, and GPC, with the analytical data shown below.

Copolymer Composition (Molar Ratio)

Monomer 1:4-hydroxyphenyl methacrylate: Adhesive monomer 1:PAG monomer 3=0.30:0.30:0.30:0.10

Mw=8,300

Mw/Mn=1.85

Synthesis Example 26

A 2-L flask was charged with 7.0 g of Monomer 8, 5.3 g of 4-hydroxyphenyl methacrylate, 7.4 g of Adhesive monomer 2, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^1$H-NMR, and GPC, with the analytical data shown below.

Copolymer Composition (Molar Ratio)

Monomer 2:4-hydroxyphenyl methacrylate: Adhesive monomer 2:PAG monomer 3=0.30:0.30:0.30:0.10

Mw=7,800

Mw/Mn=1.79

This is designated Polymer 26.

This is designated Polymer 27.

Polymer 26

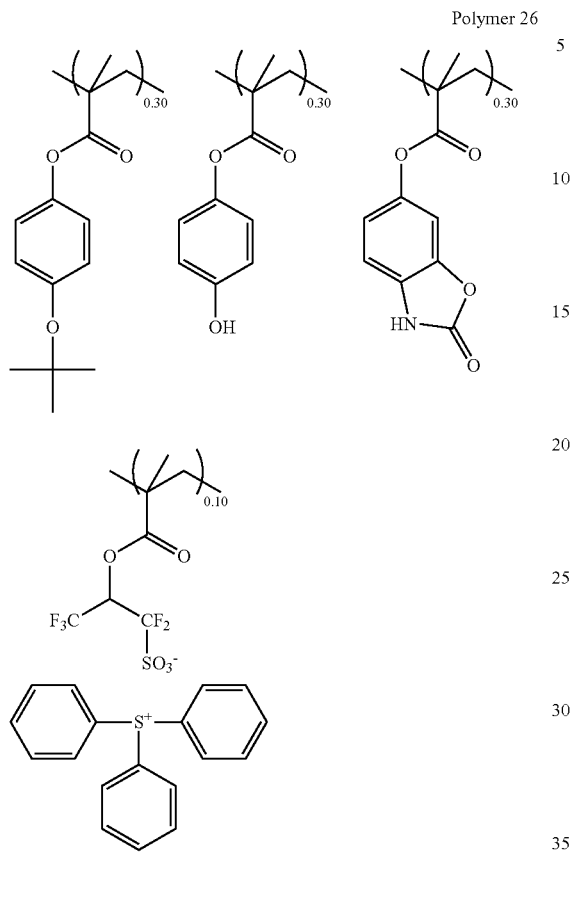

Polymer 27

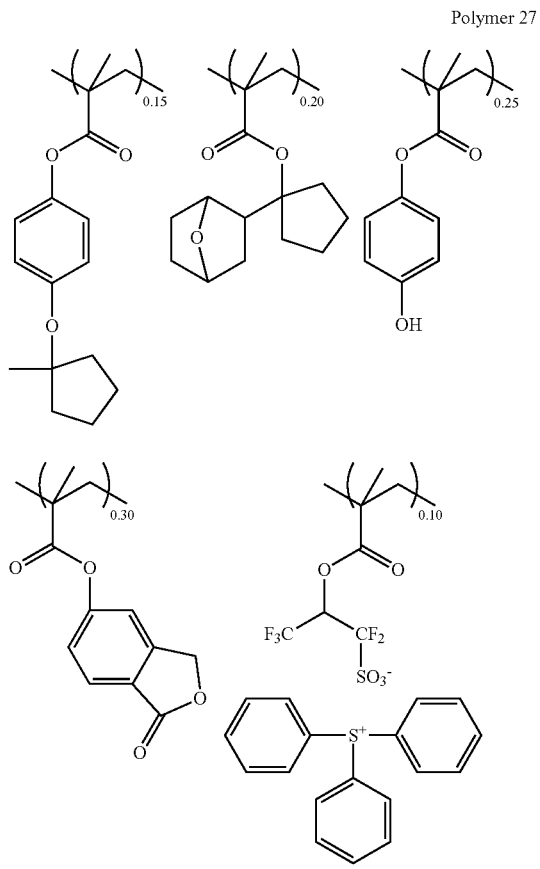

Synthesis Example 27

A 2-L flask was charged with 3.7 g of Monomer 6, 5.0 g of 2-(7-oxanorbornan-2-yl)cyclopentyl methacrylate, 4.4 g of 4-hydroxyphenyl methacrylate, 6.5 g of 2,7-dihydro-2-oxobenzo[C]furan-5-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^{1}$H-NMR, and GPC, with the analytical data shown below.

Copolymer Composition (Molar Ratio)

Monomer 6:2-(7-oxanorbornan-2-yl)cyclopentyl methacrylate:4-hydroxyphenyl methacrylate: 2,7-dihydro-2-oxobenzo[C]furan-5-yl methacrylate:PAG monomer 3=0.15:0.20:0.25:0.30:0.10

Mw=7,300
Mw/Mn=1.68

Synthesis Example 28

A 2-L flask was charged with 3.5 g of Monomer 1, 3.6 g of 1-ethylcyclopentyl methacrylate, 4.4 g of 4-hydroxyphenyl methacrylate, 6.5 g of 2,7-dihydro-2-oxobenzo[C]furan-5-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^{1}$H-NMR, and GPC, with the analytical data shown below.

Copolymer Composition (Molar Ratio)

Monomer 1:1-ethylcyclopentyl methacrylate: 4-hydroxyphenyl methacrylate: 2,7-dihydro-2-oxobenzo[C]furan-5-yl methacrylate:PAG monomer 3=0.15:0.20:0.25:0.30:0.10

Mw=7,700
Mw/Mn=1.77

This is designated Polymer 28.

This is designated Polymer 29.

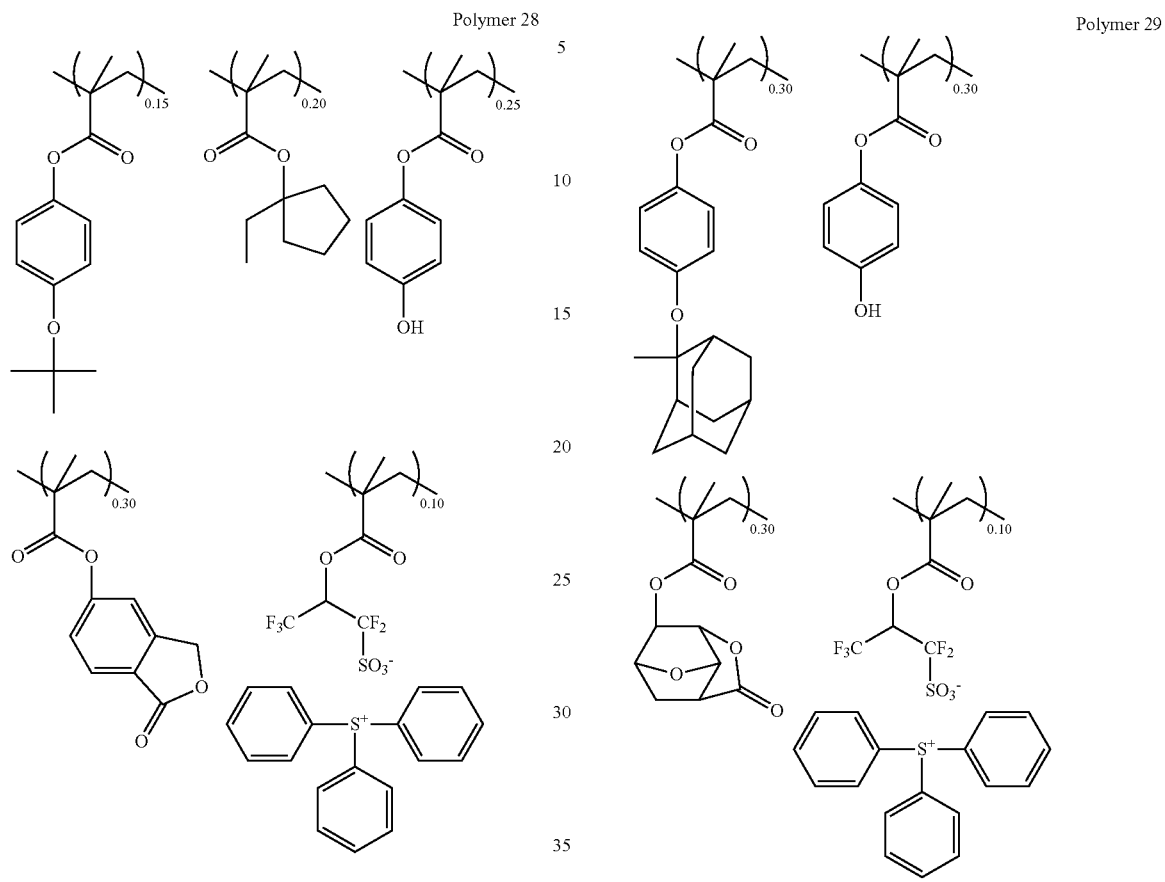

Synthesis Example 29

A 2-L flask was charged with 9.8 g of Monomer 7, 5.3 g of 4-hydroxyphenyl methacrylate, 6.7 g of 3-oxo-2,7-dioxatricyclo[4.2.1.0$^{4,8}$]nonan-9-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^1$H-NMR, and GPC, with the analytical data shown below.

Copolymer Composition (Molar Ratio)

Monomer 7:4-hydroxyphenyl methacrylate: 3-oxo-2,7-dioxatricyclo[4.2.1.0$^{4,8}$]nonan-9-yl methacrylate:PAG monomer 3=0.30:0.30:0.30:0.10

Mw=7,600

Mw/Mn=1.96

Synthesis Example 30

A 2-L flask was charged with 9.8 g of Monomer 9, 3.6 g of 4-hydroxyphenyl methacrylate, 4.5 g of 3-oxo-2,7-dioxatricyclo[4.2.1.0$^{4,8}$]nonan-9-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^1$H-NMR, and GPC, with the analytical data shown below.

Copolymer Composition (Molar Ratio)

Monomer 9:4-hydroxyphenyl methacrylate: 3-oxo-2,7-dioxatricyclo[4.2.1.0$^{4,8}$]nonan-9-yl methacrylate:PAG monomer 3=0.50:0.20:0.20:0.10

Mw=7,300

Mw/Mn=1.93

This is designated Polymer 30.

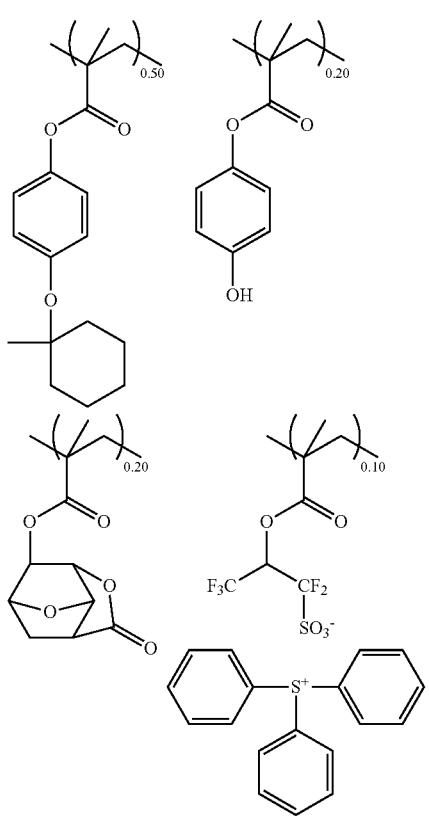

Polymer 30

This is designated Polymer 31.

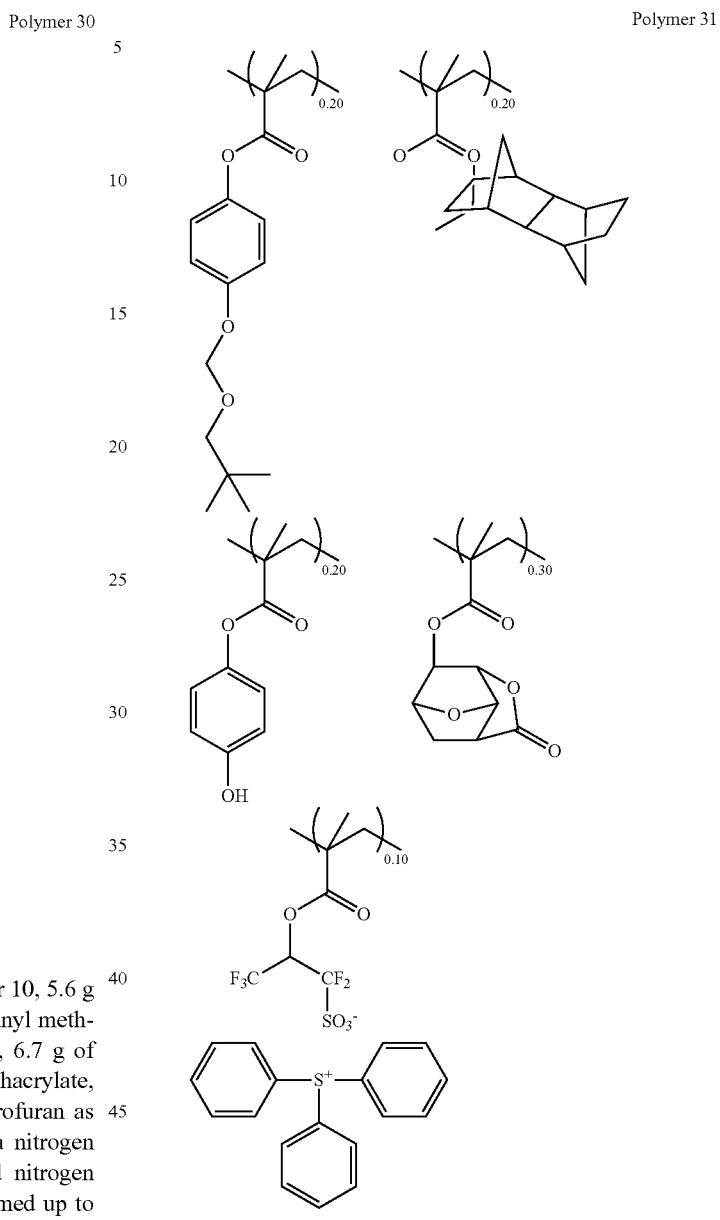

Polymer 31

Synthesis Example 31

A 2-L flask was charged with 5.6 g of Monomer 10, 5.6 g of 3-ethyl-3-exo-tetracyclo[4.4.0.1$^{2,5}$.1$^{7,10}$]dodecanyl methacrylate, 3.6 g of 4-hydroxyphenyl methacrylate, 6.7 g of 3-oxo-2,7-dioxatricyclo[4.2.1.0$^{4,8}$]nonan-9-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^{1}$H-NMR, and GPC, with the analytical data shown below.

Copolymer Composition (Molar Ratio)

Monomer 10:3-ethyl-3-exo-tetracyclo[4.4.0.1$^{2,5}$.1$^{7,10}$]-dodecanyl methacrylate:4-hydroxyphenyl methacrylate: 3-oxo-2,7-dioxatricyclo[4.2.1.0$^{4,8}$]nonan-9-yl methacrylate:PAG monomer 3=0.20:0.20:0.20:0.30:0.10

Mw=7,400

Mw/Mn=1.84

Synthesis Example 32

A 2-L flask was charged with 13.7 g of Monomer 11, 3.6 g of 4-hydroxyphenyl methacrylate, 6.7 g of 3-oxo-2,7-dioxatricyclo[4.2.1.0$^{4,8}$]nonan-9-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^{1}$H-NMR, and GPC, with the analytical data shown below.

Copolymer Composition (Molar Ratio)
Monomer 11:4-hydroxyphenyl methacrylate: 3-oxo-2,7-dioxatricyclo[4.2.1.0$^{4,8}$]nonan-9-yl methacrylate:PAG monomer 3=0.40:0.20:0.30:0.10
Mw=7,900
Mw/Mn=1.41
This is designated Polymer 32.

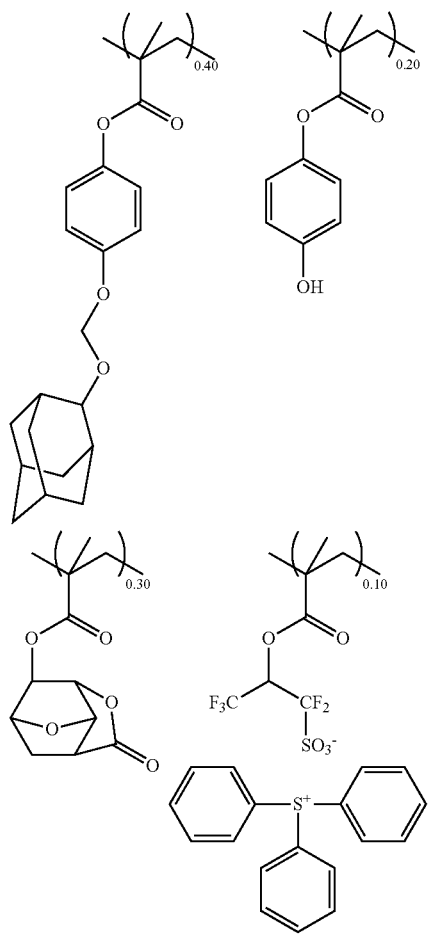

Polymer 32

Mw=7,600
Mw/Mn=1.59
This is designated Polymer 33.

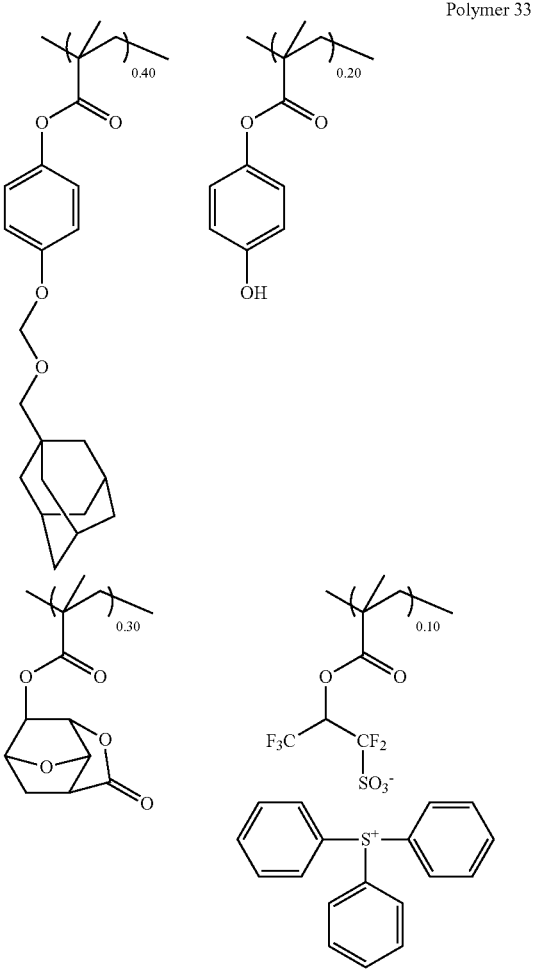

Polymer 33

Synthesis Example 33

A 2-L flask was charged with 14.2 g of Monomer 12, 3.6 g of 4-hydroxyphenyl methacrylate, 6.7 g of 3-oxo-2,7-dioxatricyclo[4.2.1.0$^{4,8}$]nonan-9-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^{1}$H-NMR, and GPC, with the analytical data shown below.
Copolymer Composition (Molar Ratio)
Monomer 12:4-hydroxyphenyl methacrylate: 3-oxo-2,7-dioxatricyclo[4.2.1.0$^{4,8}$]nonan-9-yl methacrylate:PAG monomer 3=0.40:0.20:0.30:0.10

Synthesis Example 34

A 2-L flask was charged with 11.5 g of Monomer 13, 3.6 g of 4-hydroxyphenyl methacrylate, 6.7 g of 3-oxo-2,7-dioxatricyclo[4.2.1.0$^{4,8}$]nonan-9-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^{1}$H-NMR, and GPC, with the analytical data shown below.
Copolymer Composition (Molar Ratio)
Monomer 13:4-hydroxyphenyl methacrylate: 3-oxo-2,7-dioxatricyclo[4.2.1.0$^{4,8}$]nonan-9-yl methacrylate:PAG monomer 3=0.40:0.20:0.30:0.10
Mw=7,700
Mw/Mn=1.65

This is designated Polymer 34.

This is designated Polymer 35.

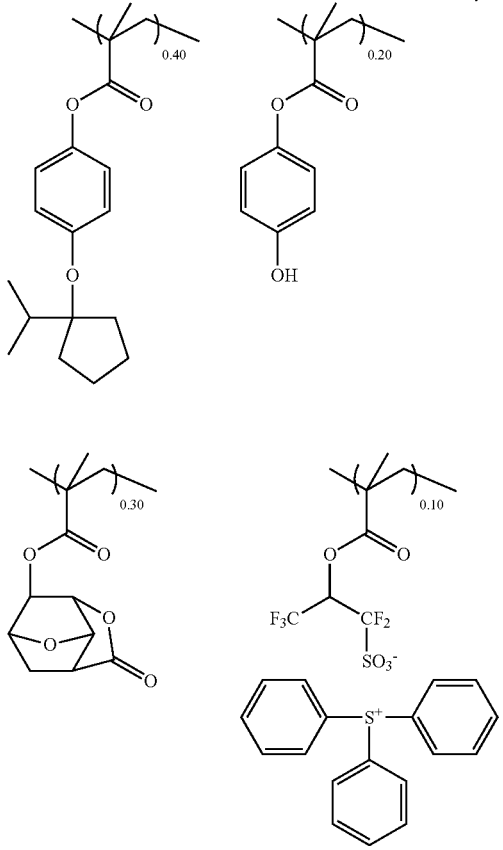

Polymer 34

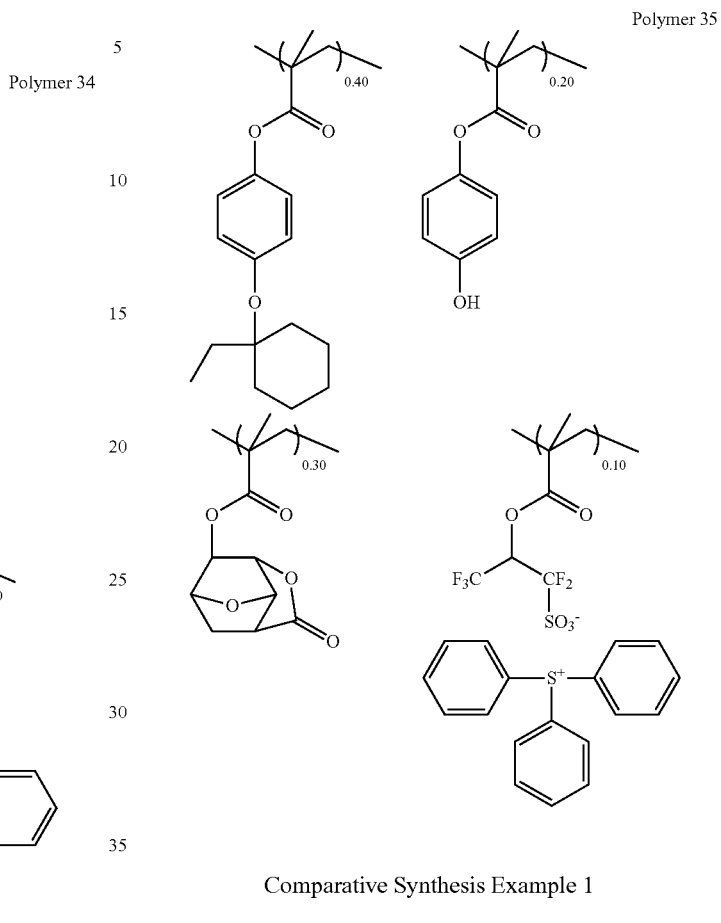

Polymer 35

Synthesis Example 35

A 2-L flask was charged with 11.5 g of Monomer 14, 3.6 g of 4-hydroxyphenyl methacrylate, 6.7 g of 3-oxo-2,7-dioxatricyclo[4.2.1.0$^{4,8}$]nonan-9-yl methacrylate, 5.6 g of PAG monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as a polymerization initiator. The reactor was heated at 60° C. and reaction run for 15 hours. The reaction solution was precipitated from 1 L of isopropyl alcohol. The white solid was collected by filtration and vacuum dried at 60° C., obtaining a white polymer.

The polymer was analyzed by $^{13}$C-NMR, $^{1}$H-NMR, and GPC, with the analytical data shown below.

Copolymer Composition (Molar Ratio)

Monomer 14:4-hydroxyphenyl methacrylate: 3-oxo-2,7-dioxatricyclo[4.2.1.0$^{4,8}$]nonan-9-yl methacrylate:PAG monomer 3=0.40:0.20:0.30:0.10

Mw=7,600

Mw/Mn=1.79

Comparative Synthesis Example 1

A polymer was synthesized by the same procedure as Synthesis Example 1 aside from using 1-ethylcyclopentyl methacrylate instead of Monomer 1. The polymer was analyzed by $^{13}$C-NMR, $^{1}$H-NMR, and GPC, with the analytical data shown below.

Copolymer Composition (Molar Ratio)

hydroxystyrene:1-ethylcyclopentyl methacrylate=0.70:0.30

Mw=9,300

Mw/Mn=1.86

This is designated Comparative Polymer 1.

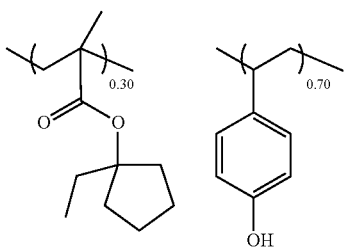

Comparative Polymer 1

Comparative Synthesis Example 2

A polymer was synthesized by the same procedure as Synthesis Example 1 aside from using 4-t-butoxystyrene instead of Monomer 1. The polymer was analyzed by $^{13}$C-NMR, $^1$H-NMR, and GPC, with the analytical data shown below.

Copolymer Composition (Molar Ratio)
4-t-butoxystyrene:hydroxystyrene=0.30:0.70
Mw=8,100
Mw/Mn=1.69

This is designated Comparative Polymer 2.

Comparative Polymer 2

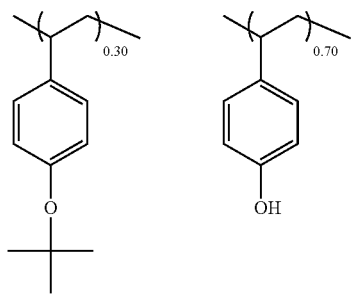

Comparative Synthesis Example 3

A polymer was synthesized by the same procedure as Synthesis Example 5 aside from using 1-ethylcyclopentyl methacrylate instead of Monomer 5. The polymer was analyzed by $^{13}$C-NMR, $^1$H-NMR, and GPC, with the analytical data shown below.

Copolymer Composition (Molar Ratio)
hydroxystyrene:1-ethylcyclopentyl methacrylate:indene=0.73:0.17:0.10
Mw=8,100
Mw/Mn=1.79

This is designated Comparative Polymer 3.

Comparative Polymer 3

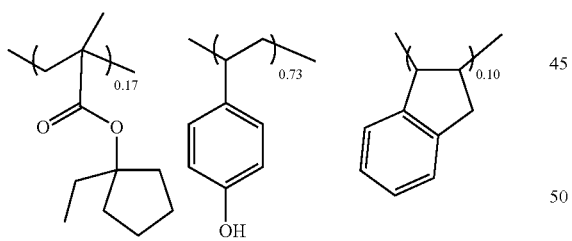

Comparative Synthesis Example 4

A polymer was synthesized by the same procedure as Synthesis Example 8 aside from using 1-ethylcyclopentyl methacrylate instead of Monomer 1. The polymer was analyzed by $^{13}$C-NMR, $^1$H-NMR, and GPC, with the analytical data shown below.

Copolymer Composition (Molar Ratio)
hydroxystyrene:1-ethylcyclopentyl methacrylate:acenaphthylene=0.75:0.15:0.10
Mw=7,200
Mw/Mn=1.79

This is designated Comparative Polymer 4.

Comparative Polymer 4

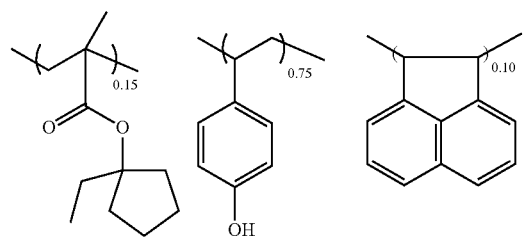

Comparative Synthesis Example 5

A polymer was synthesized by the same procedure as Synthesis Example 18 aside from using 1-ethylcyclopentyl methacrylate instead of Monomer 1. The polymer was analyzed by $^{13}$C-NMR, $^1$H-NMR, and GPC, with the analytical data shown below.

Copolymer Composition (Molar Ratio)
1-ethylcyclopentyl methacrylate:4-hydroxyphenyl methacrylate:3-oxo-2,7-dioxatricyclo[4.2.1.0$^{4,8}$]nonan-9-yl methacrylate:PAG monomer 3=0.30:0.30:0.30:0.10
Mw=7,800
Mw/Mn=1.93

This is designated Comparative Polymer 5.

Comparative Polymer 5

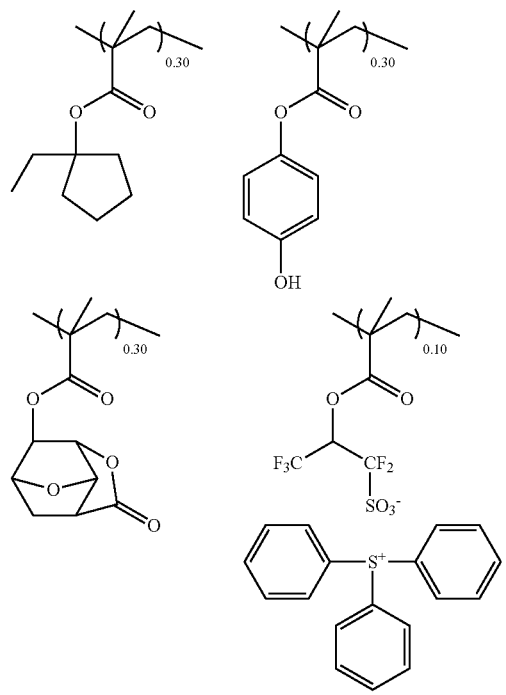

Comparative Synthesis Example 6

A polymer was synthesized as in Synthesis Example 1. The polymer was analyzed by $^1$C-NMR, $^1$H-NMR, and GPC, with the analytical data shown below.

Copolymer Composition (Molar Ratio)
  1-t-butoxy-4-naphthalene methacrylate: 1-ethylcyclopen-
    tyl methacrylate:hydroxystyrene=0.20:0.10:0.70
Mw=8,100
Mw/Mn=1.81
  This is designated Comparative Polymer 6.

Comparative Polymer 6

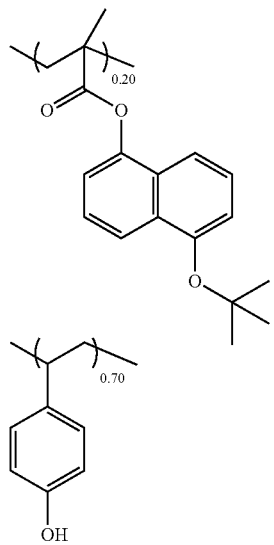
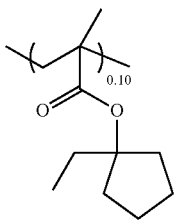
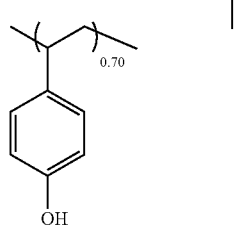

Examples and Comparative Examples

EB Writing Test

Positive resist compositions were prepared by dissolving each of the polymers synthesized above and selected components in a solvent in accordance with the recipe shown in Tables 1 and 2, and filtering through a filter having a pore size of 0.2 μm. The solution contained 100 ppm of a surfactant FC-4430 (3M Sumitomo Co., Ltd.).

The components in Tables 1 and 2 are as identified below.
Polymers 1 to 35: polymers synthesized in Synthesis Examples 1 to 35
Comparative Polymers 1 to 6:
  polymers synthesized in Comparative Synthesis Examples 1 to 6
Organic solvents: propylene glycol monomethyl ether acetate (PGMEA)
  cyclohexanone (CyH)
Acid generators: PAG1 and PAG2
Basic compounds: Amine 1, Amine 2, and Amine 3
Dissolution regulators: DRI1 and DRI2

The structural formulae of these components are shown below.

PAG 1

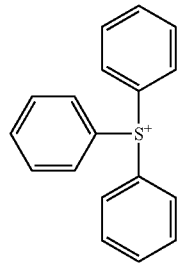
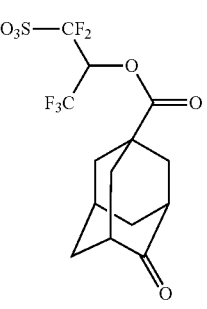

PAG 2

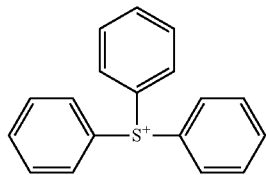
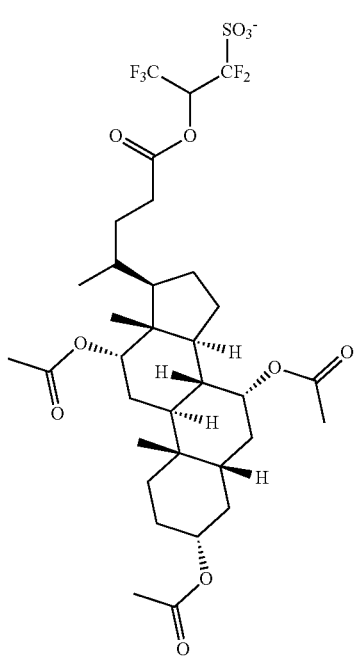

Amine 1

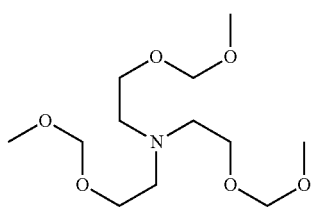

Amine 2

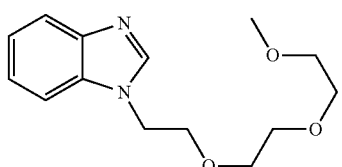

Amine 3

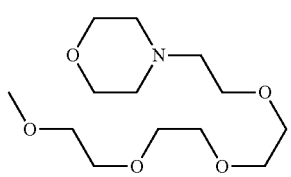

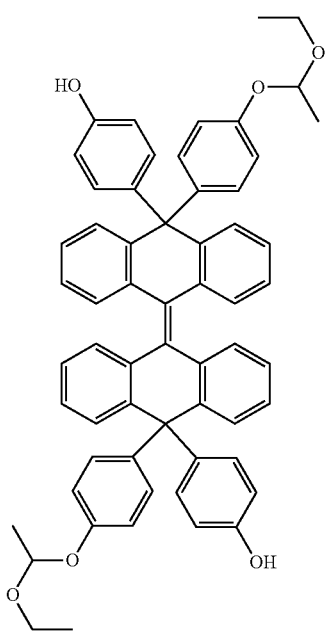

DRI 1

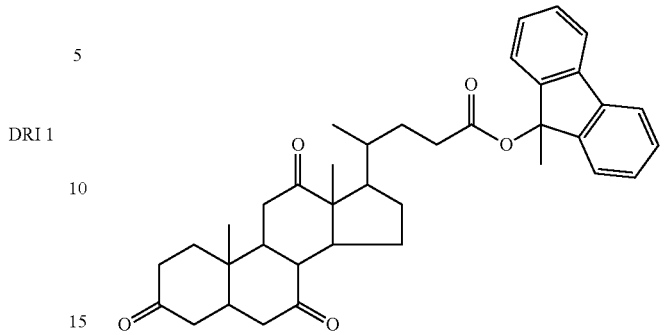

DRI 2

Using a coater/developer system Clean Track Mark 5 (Tokyo Electron Ltd.), the positive resist composition was spin coated onto a silicon substrate (diameter 6 inches) and prebaked on a hot plate at 110° C. for 60 seconds to form a resist film of 100 nm thick. Using a system HL-800D (Hitachi Ltd.) at a HV voltage of 50 kV, the resist film was exposed imagewise to EB in a vacuum chamber. Using Clean Track Mark 5, immediately after the imagewise exposure, the wafer was baked (PEB) on a hot plate for 60 seconds and puddle developed in a 2.38 wt % TMAH aqueous solution for 30 seconds to form a positive pattern.

Resolution is a minimum size at the exposure dose (sensitivity) that provides a 1:1 resolution of a 120-nm line-and-space pattern. The 120-nm line-and-space pattern was measured for line width roughness (LWR) under SEM.

The resist composition is shown in Tables 1 and 2 together with the sensitivity and resolution of EB lithography.

TABLE 1

| | | Polymer (pbw) | Acid generator (pbw) | Base (pbw) | Dissolution regulator (pbw) | Organic solvent (pbw) | PEB temp. (° C.) | Sensitivity ($\mu C/cm^2$) | Resolution (nm) | LWR (nm) |
|---|---|---|---|---|---|---|---|---|---|---|
| Example | 1 | Polymer 1 (100) | PAG 2 (10) | Amine 1 (0.4) | — | PGMEA (2,000) | 85 | 29 | 95 | 6.2 |
| | 2 | Polymer 2 (100) | PAG 2 (10) | Amine 1 (0.4) | — | PGMEA (2,000) | 95 | 33 | 90 | 6.5 |
| | 3 | Polymer 3 (100) | PAG 2 (10) | Amine 1 (0.4) | — | PGMEA (2,000) | 95 | 35 | 90 | 7.1 |
| | 4 | Polymer 4 (100) | PAG 2 (10) | Amine 1 (0.4) | — | PGMEA (2,000) | 95 | 42 | 85 | 7.0 |
| | 5 | Polymer 5 (100) | PAG 1 (10) | Amine 1 (0.4) | — | PGMEA (2,000) | 90 | 35 | 90 | 6.3 |
| | 6 | Polymer 6 (100) | PAG 1 (10) | Amine 1 (0.4) | — | PGMEA (2,000) | 85 | 36 | 90 | 6.2 |
| | 7 | Polymer 7 (100) | PAG 2 (10) | Amine 1 (0.4) | — | PGMEA (2,000) | 90 | 36 | 85 | 6.3 |
| | 8 | Polymer 8 (100) | PAG 1 (10) | Amine 1 (0.4) | — | PGMEA (2,000) | 90 | 30 | 85 | 7.1 |
| | 9 | Polymer 9 (100) | PAG 1 (10) | Amine 1 (0.4) | — | PGMEA (2,000) | 90 | 34 | 85 | 6.8 |
| | 10 | Polymer 10 (100) | PAG 1 (10) | Amine 1 (0.4) | — | PGMEA (2,000) | 90 | 35 | 85 | 6.4 |
| | 11 | Polymer 11 (100) | PAG 1 (10) | Amine 1 (0.4) | — | PGMEA (2,000) | 95 | 44 | 85 | 6.1 |
| | 12 | Polymer 12 (100) | PAG 1 (10) | Amine 1 (0.4) | — | PGMEA (2,000) | 90 | 32 | 90 | 7.2 |
| | 13 | Polymer 13 (100) | PAG 1 (10) | Amine 1 (0.4) | — | PGMEA (2,000) | 95 | 33 | 90 | 7.2 |
| | 14 | Polymer 14 (100) | PAG 2 (10) | Amine 1 (0.4) | — | PGMEA (2,000) | 90 | 45 | 80 | 5.8 |
| | 15 | Polymer 15 (100) | PAG 1 (10) | Amine 1 (0.4) | — | PGMEA (2,000) | 95 | 47 | 82 | 5.9 |
| | 16 | Polymer 16 (100) | — | Amine 1 (0.4) | — | PGMEA(800) CyH(1,200) | 95 | 42 | 65 | 4.9 |
| | 17 | Polymer 17 (100) | — | Amine 1 (0.4) | — | PGMEA(800) CyH(1,200) | 95 | 36 | 80 | 5.2 |

TABLE 1-continued

| | | Polymer (pbw) | Acid generator (pbw) | Base (pbw) | Dissolution regulator (pbw) | Organic solvent (pbw) | PEB temp. (° C.) | Sensitivity (μC/cm$^2$) | Resolution (nm) | LWR (nm) |
|---|---|---|---|---|---|---|---|---|---|---|
| | 18 | Polymer 18 (100) | — | Amine 1 (0.4) | — | PGMEA(800) CyH(1,200) | 95 | 40 | 65 | 5.3 |
| | 19 | Polymer 19 (100) | — | Amine 1 (0.4) | — | PGMEA(800) CyH(1,200) | 95 | 33 | 65 | 5.6 |
| | 20 | Polymer 20 (100) | — | Amine 1 (0.4) | — | PGMEA(800) CyH(1,200) | 95 | 47 | 70 | 4.8 |
| | 21 | Polymer 21 (100) | — | Amine 1 (0.4) | — | PGMEA(800) CyH(1,200) | 95 | 44 | 70 | 4.2 |
| | 22 | Polymer 22 (100) | — | Amine 1 (0.4) | — | PGMEA(800) CyH(1,200) | 90 | 44 | 70 | 4.1 |
| | 23 | Polymer 23 (100) | — | Amine 1 (0.4) | — | PGMEA(800) CyH(1,200) | 90 | 48 | 70 | 5.0 |
| | 24 | Polymer 24 (100) | — | Amine 1 (0.4) | — | PGMEA(800) CyH(1,200) | 90 | 41 | 70 | 4.7 |
| | 25 | Polymer 25 (100) | — | Amine 1 (0.4) | — | PGMEA(800) CyH(1,200) | 95 | 52 | 70 | 4.3 |
| | 26 | Polymer 26 (100) | — | Amine 1 (0.4) | — | PGMEA(800) CyH(1,200) | 95 | 42 | 65 | 5.0 |

TABLE 2

| | | Polymer (pbw) | Acid generator (pbw) | Base (pbw) | Dissolution regulator (pbw) | Organic solvent (pbw) | PEB temp. (° C.) | Sensitivity (μC/cm$^2$) | Resolution (nm) | LWR (nm) |
|---|---|---|---|---|---|---|---|---|---|---|
| Example | 27 | Polymer 27 (100) | — | Amine 1 (0.4) | — | PGMEA(800) CyH(1,200) | 95 | 40 | 65 | 4.7 |
| | 28 | Polymer 28 (100) | — | Amine 1 (0.4) | — | PGMEA(800) CyH(1,200) | 95 | 44 | 65 | 4.6 |
| | 29 | Polymer 29 (100) | — | Amine 1 (0.4) | — | PGMEA(800) CyH(1,200) | 95 | 46 | 65 | 4.2 |
| | 30 | Polymer 18 (100) | — | Amine 2 (0.4) | — | PGMEA(800) CyH(1,200) | 95 | 46 | 75 | 4.6 |
| | 31 | Polymer 18 (100) | — | Amine 3 (0.4) | — | PGMEA(800) CyH(1,200) | 95 | 46 | 75 | 4.3 |
| | 32 | Polymer 18 (100) | — | Amine 1 (0.4) | DRI 1 (10) | PGMEA(800) CyH(1.200) | 90 | 38 | 80 | 4.3 |
| | 33 | Polymer 18 (100) | — | Amine 1 (0.4) | DRI 2 (10) | PGMEA(800) CyH(1,200) | 90 | 36 | 80 | 4.4 |
| | 34 | Polymer 30 (100) | — | Amine 1 (0.4) | — | PGMEA(800) CyH(1,200) | 95 | 48 | 65 | 3.8 |
| | 35 | Polymer 31 (100) | — | Amine 1 (0.4) | — | PGMEA(800) CyH(1.200) | 95 | 39 | 65 | 4.2 |
| | 36 | Polymer 32 (100) | — | Amine 1 (0.4) | — | PGMEA(800) CyH(1,200) | 95 | 48 | 65 | 4.2 |
| | 37 | Polymer 33 (100) | — | Amine 1 (0.4) | — | PGMEA(800) CyH(1,200) | 95 | 49 | 65 | 4.2 |
| | 38 | Polymer 34 (100) | — | Amine 1 (0.4) | — | PGMEA(800) CyH(1,200) | 75 | 49 | 65 | 3.8 |
| | 39 | Polymer 35 (100) | — | Amine 1 (0.4) | — | PGMEA(800) CyH(1,200) | 85 | 46 | 65 | 4.0 |
| Comparative Example | 1 | Comparative Polymer 1 (100) | PAG 2 (10) | Amine 1 (0.4) | — | PGMEA (2,000) | 90 | 22 | 110 | 7.2 |
| | 2 | Comparative Polymer 2 (100) | PAG 2 (10) | Amine 1 (0.4) | — | PGMEA (2,000) | 95 | 28 | 120 | 7.3 |
| | 3 | Comparative Polymer 3 (100) | PAG 2 (10) | Amine 1 (0.4) | — | PGMEA (2,000) | 90 | 28 | 100 | 7.1 |
| | 4 | Comparative Polymer 4 (100) | PAG 2 (10) | Amine 1 (0.4) | — | PGMEA (2,000) | 90 | 32 | 95 | 7.8 |
| | 5 | Comparative Polymer 5 (100) | — | Amine 1 (0.4) | — | PGMEA(800) CyH(1,200) | 90 | 33 | 95 | 6.5 |
| | 6 | Comparative Polymer 6 (100) | PAG 2 (10) | Amine 1 (0.4) | — | PGMEA(800) CyH(1,200) | 100 | 45 | 120 | 8.9 |

Dry Etching Test

Each polymer, 2 g, was dissolved in 10 g of cyclohexanone and passed through a filter having a pore size of 0.2 μm, obtaining a polymer solution. The polymer solution was spin coated onto a silicon substrate and baked to form a polymer film of 300 nm thick. Using a dry etching instrument TE-8500P (Tokyo Electron Ltd.), the polymer film was etched with $CHF_3/CF_4$ gas under the following conditions.

| | |
|---|---|
| Chamber pressure | 40.0 Pa |
| RF power | 1000 W |
| Gap | 9 mm |
| $CHF_3$ gas flow rate | 30 ml/min |
| $CF_4$ gas flow rate | 30 ml/min |
| Ar gas flow rate | 100 ml/min |
| Time | 60 sec |

The difference in polymer film thickness before and after etching was determined, from which an etching rate per minute was computed. The results are shown in Table 3. A smaller value of film thickness difference, i.e., a lower etching rate indicates better etching resistance.

TABLE 3

| | | | $CHF_3/CF_4$ gas etching rate (nm/min) |
|---|---|---|---|
| Example | 40 | Polymer 1 | 98 |
| | 41 | Polymer 2 | 109 |
| | 42 | Polymer 3 | 107 |
| | 43 | Polymer 4 | 110 |
| | 44 | Polymer 5 | 93 |
| | 45 | Polymer 6 | 100 |
| | 46 | Polymer 7 | 105 |
| | 47 | Polymer 8 | 92 |
| | 48 | Polymer 9 | 93 |
| | 49 | Polymer 10 | 95 |
| | 50 | Polymer 11 | 102 |
| | 51 | Polymer 12 | 94 |
| | 52 | Polymer 13 | 96 |
| | 53 | Polymer 14 | 102 |
| | 54 | Polymer 15 | 95 |
| | 55 | Polymer 16 | 100 |
| | 56 | Polymer 17 | 97 |
| | 57 | Polymer 18 | 99 |
| | 58 | Polymer 19 | 98 |
| | 59 | Polymer 20 | 98 |
| | 60 | Polymer 21 | 97 |
| | 61 | Polymer 22 | 95 |
| | 62 | Polymer 23 | 96 |
| | 63 | Polymer 24 | 95 |
| | 64 | Polymer 25 | 98 |
| | 65 | Polymer 26 | 98 |
| | 66 | Polymer 27 | 101 |
| | 67 | Polymer 28 | 97 |
| | 68 | Polymer 29 | 93 |
| | 69 | Polymer 30 | 98 |
| | 70 | Polymer 31 | 96 |
| | 71 | Polymer 32 | 93 |
| | 72 | Polymer 33 | 94 |
| | 73 | Polymer 34 | 98 |
| | 74 | Polymer 35 | 97 |
| Comparative Example | 7 | Comparative Polymer 1 | 122 |
| | 8 | Comparative Polymer 2 | 106 |
| | 9 | Comparative Polymer 3 | 108 |
| | 10 | Comparative Polymer 4 | 102 |
| | 11 | Comparative Polymer 5 | 108 |
| | 12 | Comparative Polymer 6 | 98 |

EUV Exposure Test

A positive resist composition was prepared by dissolving each of the polymers synthesized above and selected components in a solvent in accordance with the recipe shown in Table 4, and filtering through a filter having a pore size of 0.2 μm. Notably, the composition further contained 100 ppm of a surfactant FC-4430 (3M Sumitomo Co., Ltd.). The resist composition was spin coated on a silicon substrate (diameter 4 inches, vapor primed with hexamethyldisilazane (HMDS)) and prebaked on a hot plate at 105° C. for 60 seconds to form a resist film of 50 nm thick. EUV exposure was performed by dipole illumination at NA 0.3. Immediately after the exposure, the substrate was baked (PEB) on a hot plate for 60 seconds and puddle developed with a 2.38 wt % TMAH aqueous solution for 30 seconds to form a positive pattern.

Resolution is a minimum size at the exposure dose (sensitivity) that provides a 1:1 resolution of a 35-nm line-and-space pattern. The 35-nm line-and-space pattern was measured for line width roughness (LWR) under SEM.

The resist composition is shown in Table 4 together with the sensitivity and resolution of EUV lithography.

TABLE 4

| | Polymer (pbw) | Acid generator (pbw) | Base (pbw) | Organic solvent (pbw) | PEB temp. (° C.) | Sensitivity (mJ/cm$^2$) | Resolution (nm) | LWR (nm) |
|---|---|---|---|---|---|---|---|---|
| Example 75 | Polymer 16 (100) | — | Amine 3 (0.8) | PGMEA(1,000) CyH(2,000) PGME(500) | 95 | 12 | 26 | 4.5 |
| Comparative Example 13 | Comparative Polymer 1 (100) | PAG 2 (10) | Amine 3 (0.8) | PGMEA(1,000) CyH(2,000) PGME(500) | 90 | 12 | 32 | 7.5 |
| Comparative Example 14 | Comparative Polymer 5 (100) | — | Amine 3 (0.8) | PGMEA(1,000) CyH(2,000) PGME(500) | 90 | 12 | 30 | 5.3 |

It is evident from Tables 1 and 2 that the resist compositions using the inventive polymers meet satisfactory resolution, sensitivity and edge roughness. They have good dry etching resistance as demonstrated by a smaller difference in film thickness before and after etching in Table 3. It is evident from Table 4 that the polymers prevent pattern collapse, thereby improving resolution and roughness.

Japanese Patent Application No. 2010-125889 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymer having a weight average molecular weight of 1,000 to 500,000, and comprising recurring units (a) having the general formula (2):

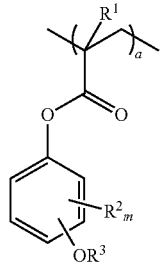

(2)

wherein $R^1$ is hydrogen or methyl, $R^2$ is hydrogen or $C_1$-$C_4$ alkyl, $R^3$ is an acid labile group, m is an integer of 1 to 4, and a is a positive number from more than 0 to 1.0, and recurring units (b) having an adhesive group selected from the group consisting of cyclic —O—C(=O)—S— and cyclic —O—C(=O)—NH— wherein fractions "a" and "b" of the respective units are numbers in the range: 0<a <1.0, 0<b <1.0, and 0.05≤a+b≤1.0.

2. A chemically amplified positive resist composition comprising the polymer of claim 1 and an organic solvent.

3. A pattern forming process comprising the steps of applying the positive resist composition of claim 2 onto a substrate to form a coating, heat treating and exposing the coating to high-energy radiation, and developing the exposed coating with a developer.

4. A polymer having a weight average molecular weight of 1,000 to 500,000, and comprising recurring units (a) having the general formula (2):

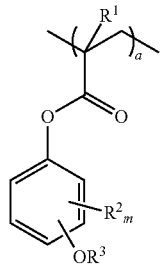

(2)

wherein $R^1$ is hydrogen or methyl, $R^2$ is hydrogen or $C_1$-$C_4$ alkyl, $R^3$ is an acid labile group, m is an integer of 1 to 4, and a is a positive number from more than 0 to less than 1.0, and recurring units (b4), (b7) or (b8) having the general formula (3):

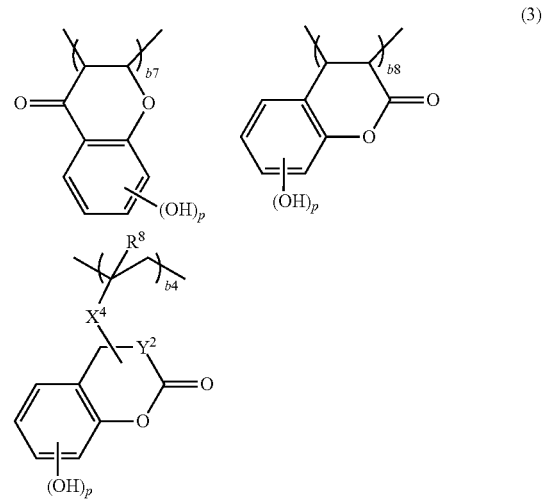

(3)

wherein $R^8$ is hydrogen or methyl, $X^4$ is a group —C(=O)—O—$R^9$—, $R^9$ is a single bond or $C_1$-$C_{10}$ straight, branched or cyclic alkylene, $Y^2$ is methylene or ethylene, p is 1 or 2, b4, b7 and b8 are positive numbers in the range: 0 ≤b4<1.0, 0≤b7<1.0, 0≤b8 <1.0, and 0<b4+b7+b8<1.0.

5. A chemically amplified positive resist composition comprising the polymer of claim 4 and an organic solvent.

6. A pattern forming process comprising the steps of applying the positive resist composition of claim 5 onto a substrate to form a coating, heat treating and exposing the coating to high-energy radiation, and developing the exposed coating with a developer.

7. A polymer having a weight average molecular weight of 1,000 to 500,000, and comprising recurring units (a) having the general formula (2):

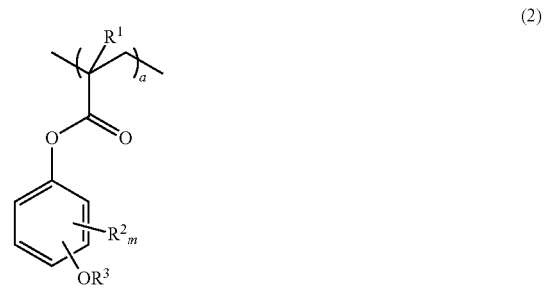

(2)

wherein $R^1$ is hydrogen or methyl, $R^2$ is hydrogen or $C_1$-$C_4$ alkyl, $R^3$ is an acid labile group, m is an integer of 1 to 4, and a is a positive number from more than 0 to less than 1.0, and recurring units (c) of at least one type selected from recurring units (c3) to (c5) of chromone, coumarin, and norbornadiene, or derivatives thereof, represented by the general formula (4):

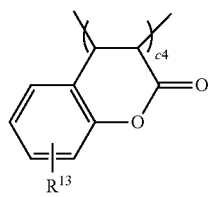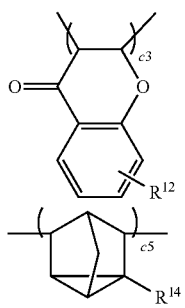

(4)

wherein $R^{12}$ to $R^{14}$ are each independently selected from the group consisting of hydrogen, $C_1$-$C_{30}$ alkyl, $C_1$-$C_{30}$ alkyl wherein some or all carbon-bonded hydrogen atoms are substituted by halogen atoms, $C_1$-$C_8$ alkoxy, $C_1$-$C_8$ alkanoyl, $C_2$-$C_8$ alkoxycarbonyl, $C_6$-$C_{10}$ aryl, halogen, and 1,1,1,3,3,3-hexafluoro-2-propanol group, c3 to c5 are positive numbers in the range: $0 \le c3 < 1.0$, $0 \le c4 < 1.0$, $0 \le c5 < 1.0$, and $0 < c3+c4+c5 < 1.0$.

8. A chemically amplified positive resist composition comprising the polymer of claim 7 and an organic solvent.

9. A pattern forming process comprising the steps of applying the positive resist composition of claim 8 onto a substrate to form a coating, heat treating and exposing the coating to high-energy radiation, and developing the exposed coating with a developer.

\* \* \* \* \*